(12) United States Patent
Zheng et al.

(10) Patent No.: US 12,392,773 B2
(45) Date of Patent: Aug. 19, 2025

(54) DEVICES, SYSTEMS, AND METHODS FOR ANALYTE SENSING WITH OPTOTHERMALLY GENERATED BUBBLES IN BIPHASIC LIQUID SAMPLES

(71) Applicant: BOARD OF REGENTS, THE UNIVERSITY OF TEXAS SYSTEM, Austin, TX (US)

(72) Inventors: Yuebing Zheng, Austin, TX (US); Youngsun Kim, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 443 days.

(21) Appl. No.: 18/015,808

(22) PCT Filed: Jul. 8, 2021

(86) PCT No.: PCT/US2021/040795
§ 371 (c)(1),
(2) Date: Jan. 12, 2023

(87) PCT Pub. No.: WO2022/015558
PCT Pub. Date: Jan. 20, 2022

(65) Prior Publication Data
US 2023/0258630 A1 Aug. 17, 2023

Related U.S. Application Data

(60) Provisional application No. 63/051,132, filed on Jul. 13, 2020.

(51) Int. Cl.
*G01N 33/543* (2006.01)
*G01N 21/552* (2014.01)
(Continued)

(52) U.S. Cl.
CPC ..... *G01N 33/54373* (2013.01); *G01N 21/554* (2013.01); *G01N 33/56983* (2013.01);
(Continued)

(58) Field of Classification Search
CPC .......... G01N 33/54373; G01N 21/554; G01N 33/56983; G01N 2201/06; G01N 2333/11;
(Continued)

(56) References Cited

U.S. PATENT DOCUMENTS 10,603,685 B2   3/2020   Zheng et al.
10,620,121 B2   4/2020   Zheng et al.
(Continued)

OTHER PUBLICATIONS

Angelsky et al. Low-temperature laser-stimulated controllable generation of micro-bubbles in a water suspension of absorptive colloid particles, Optics Express, 2018, 26(11), 13995.
(Continued)

*Primary Examiner* — Tarifur R Chowdhury
*Assistant Examiner* — Kaitlyn E Kidwell
(74) *Attorney, Agent, or Firm* — Meunier Carlin & Curfman LLC

(57) ABSTRACT

Disclosed herein are devices, systems, and methods for analyte sensing with optothermally generated bubbles in biphasic liquid samples. For example, disclosed herein are methods comprising: illuminating a first location of an optothermal substrate with electromagnetic radiation; wherein the optothermal substrate is in thermal contact with a biphasic liquid sample comprising an aqueous solution and a droplet comprising a water-immiscible liquid, the aqueous solution comprising water and a plurality of analytes; thereby: generating a bubble in the biphasic liquid sample proximate the first location of the optothermal substrate via optothermal effects, trapping at least a portion of the plu-
(Continued)

rality of analytes at the gas-liquid interface of the bubble and the aqueous solution, and depositing at least a portion of the trapped analytes onto the optothermal substrate.

20 Claims, 19 Drawing Sheets

(51) Int. Cl.
  *G01N 33/536* (2006.01)
  *G01N 33/569* (2006.01)
(52) U.S. Cl.
  CPC ....... *G01N 33/536* (2013.01); *G01N 2201/06* (2013.01); *G01N 2333/11* (2013.01); *G01N 2333/165* (2013.01)
(58) Field of Classification Search
  CPC ........... G01N 2333/165; G01N 33/536; G01N 21/553; G01N 21/658; G01N 33/54393; G01N 33/553; G02B 5/008; G02B 6/1226
  USPC ..................................................... 356/337, 38
  See application file for complete search history.

(56) References Cited

U.S. PATENT DOCUMENTS

| | | | |
|---|---|---|---|
| 11,060,976 | B2 | 7/2021 | Zheng et al. |
| 11,448,965 | B2 | 9/2022 | Zheng et al. |
| 11,519,857 | B2 | 12/2022 | Zheng et al. |
| 2008/0248591 | A1 | 10/2008 | Bauer |
| 2018/0348128 | A1 | 12/2018 | Zheng et al. |
| 2019/0113453 | A1* | 4/2019 | Zheng ................... G01N 15/14 |
| 2019/0195805 | A1* | 6/2019 | Zheng ................... G01N 21/64 |
| 2019/0264327 | A1 | 8/2019 | Zheng et al. |

OTHER PUBLICATIONS

Baffou et al. Super-Heating and Micro-Bubble Generation around Plasmonic Nanoparticles under cw Illumination, J Phys Chem C, 2014, 118, 4890-4898.
Barber EJ et al. Vapor Pressures of Perfluoropentanes. J. Phys. Chem. 1956, 60 (4), 504-505.
Blazquez-Castro. Optical Tweezers: Phototoxicity and Thermal Stress in Cells and Biomolecules, Micromachines, 2019, 10, 507.
Chernyshev VS et al. Surface Tension of Water in the Presence of Perfluorocarbon Vapors. Soft Matter 2014, 10 (12), 1937-1943.
Cosco D et al. Perfluorocarbon-Loaded Micro and Nanosystems for Medical Imaging: A State of the Art. J. Fluor. Chem. 2015, 171, 18-26. https://doi.org/10.1016/j.jfluchem.2014.10.013.
Detert et al. Plasmonic Bubble Nucleation in Binary Liquids, The Journal of Physical Chemistry C, 2020, 124, 2591-2597.
Díaz-López R et al. Liquid Perfluorocarbons as Contrast Agents for Ultrasonography and 19F-MRI. Pharm. Res. 2010, 27 (1), 1-16. https://doi.org/10.1007/s11095-009-0001-5.
Kang et al. Surface-enhanced Raman scattering via entrapment of colloidal plasmonic nanocrystals by laser generated microbubbles on random gold nano-islands, Nanoscale, 2016, 8, 10266.
Karim et al. Fabricate nanogap-rich plasmonic nanostructures through an optothermal surface bubble in a droplet, Optics Letters, 2018, 43(2), 334.
Karim F et al. Optothermal Microbubble Assisted Manufacturing of Nanogap-Rich Structures for Active Chemical Sensing. Nanoscale 2019, 11 (43), 20589-20597. https://doi.org/10.1039/C9NR05892C.
Kotnala A et al. Overcoming Diffusion-Limited Trapping in Nanoaperture Tweezers Using Opto-Thermal-Induced Flow. Nano Lett. 2020, 20 (1), 768-779. https://doi.org/10.1021/acs.nanolett.9b04876.
Lin CY et al. Ultrasound Sensitive Liposomes Containing Doxorubicin for Drug Targeting Therapy. Nanomedicine Nanotechnology, Biol. Med. 2014, 10 (1), 67-76. https://doi.org/10.1016/j.nano.2013.06.011.
Lin et al. Optothermal Manipulations of Colloidal Particles and Living Cells, Acc Chem Res, 2018, 51(6), 1465-1474.
Lin L et al. Bubble-Pen Lithography. Nano Lett. 2016, 16 (1), 701-708. https://doi.org/10.1021/acs.nanolett.5b04524.
Lin L et al. Opto-Thermoelectric Nanotweezers. Nat. Photonics 2018, 12 (4), 195-201. https://doi.org/10.1038/s41566-018-0134-3.
Moon et al. Biocompatible Direct Deposition of Functionalized Nanoparticles using Shrinking Surface Plasmonic Bubble, Advanced Materials Interfaces, 2020, 7(16), 200597.
Pang et al. Optical Trapping of Individual Human Immunodeficiency Viruses in Culture Fluid Reveals Heterogeneity with Single-Molecule Resolution, Nat Nanotechnol, 2014, 9(8), 624-630.
Rajeeva BB et al. Accumulation-Driven Unified Spatiotemporal Synthesis and Structuring of Immiscible Metallic Nanoalloys. Matter 2019, 1 (6), 1606-1617. https://doi.org/10.1016/j.matt.2019.10.017.
Rajeeva et al. Regioselective Localization and Tracking of Biomolecules on Single Gold Nanoparticles, Adv. Sci. 2015, 2, 1500232.
Rapoport N et al. Ultrasound-Mediated Tumor Imaging and Nanotherapy Using Drug Loaded, Block Copolymer Stabilized Perfluorocarbon Nanoemulsions. J. Control. Release 2011, 153 (1), 4-15. https://doi.org/10.1016/j.jconrel.2011.01.022.
Riess JG. Understanding the Fundamentals of Perfluorocarbons and Perfluorocarbon Emulsions Relevant to In Vivo Oxygen Delivery. Artif. Cells, Blood Substitutes, Biotechnol. 2005, 33 (1), 47-63. https://doi.org/10.1081/BIO-200046659.
Sarabia-Alonso et al. Optothermal generation, trapping, and manipulation of microbubbles, Optics Express, 2020, 28(12), 17672.
Schutt EG et al. Injectable Microbubbles as Contrast Agents for Diagnostic Ultrasound Imaging: The Key Role of Perfluorochemicals. Angew. Chemie—Int. Ed. 2003, 42 (28), 3218-3235. https://doi.org/10.1002/anie.200200550.
Tantussi F et al. Long-Range Capture and Delivery of Water-Dispersed Nano-Objects by Microbubbles Generated on 3D Plasmonic Surfaces. ACS Nano 2018, 12 (5), 4116-4122. https://doi.org/10.1021/acsnano.7b07893.
Tokel et al. Advances in Plasmonic Technologies for Point of Care Applications, Chemical Reviews, 2014, 114, 5728-5752.
Tokonami S et al. Light-Induced Assembly of Living Bacteria with Honeycomb Substrate. Sci. Adv. 2020, 6 (9). https://doi.org/10.1126/sciadv.aaz5757.
Wang Y et al. Vapor and Gas-Bubble Growth Dynamics around Laser-Irradiated, Water-Immersed Plasmonic Nanoparticles. ACS Nano 2017, 11 (2), 2045-2051. https://doi.org/10.1021/acsnano.6b08229.
Ward CA et al. Conditions for Stability of Bubble Nuclei in Solid Surfaces Contacting a Liquid-gas Solution. J. Appl. Phys. 1984, 56 (2), 491-500. https://doi.org/10.1063/1.333937.
Ward CA et al. Stability of Bubbles in a Closed Volume of Liquid-gas Solution. J. Appl. Phys. 1982, 53 (9), 6076-6084. https://doi.org/10.1063/1.331559.
Xie et al. An optothermally generated surface bubble and its applications, Nanoscale, 2017, 9, 6622.
Xie et al. Optoacoustic tweezers: a programmable, localized cell concentrator based on opto-thermally generated, acoustically activated, surface bubbles, Lab Chip, 2013, 13(9), 1772-1779.
Yang P et al. Stimuli-Responsive Biodegradable Poly(Methacrylic Acid) Based Nanocapsules for Ultrasound Traced and Triggered Drug Delivery System. Biomaterials 2014, 35 (6), 2079-2088. https://doi.org/10.1016/j.biomaterials.2013.11.057.
Zaytsev ME et al. Plasmonic Bubbles in N-Alkanes. J. Phys. Chem. C 2018, 122 (49), 28375-28381. https://doi.org/10.1021/acs.jpcc.8b09617.
Zhao et al. Theory and experiment on particle trapping and manipulation via optothermally generated bubbles, Lab on a Chip, 2014, 14, 384.
International Search Report and Written Opinion received in PCT/US2021/040795, mailed Oct. 18, 2021, 14 pages.
Boyd et al., "Chemical Separations by Bubble-Assisted Interface Mass-Transfer." Anal. Chem. 2008, 80, 2452-2456 [online] Apr. 1, 2008 {Apr. 1, 2008), entire document [online] <URL: https://pubs.acs.org/doi/abs/10.1021/ac702174t> <DOI: 10.1021/ac702174t>.

(56) References Cited

OTHER PUBLICATIONS

Kim, HD, et al. Enhanced Surface Capture and Sensing of Proteins with Low-Power X,P Optothermal Bubbles In a Biphasic Liquid. Nano. Lett. 2020, 20, 10, 7020-7027 [online] Jul. 15, 2020 {Jul. 15, 2020), entire document [online] <URL: https://pubs.acs.org/doi/abs/10.1021/acs.nanolett.0c01969> <DOI: 10.1021/acs.nanolett.0c01969>.

\* cited by examiner

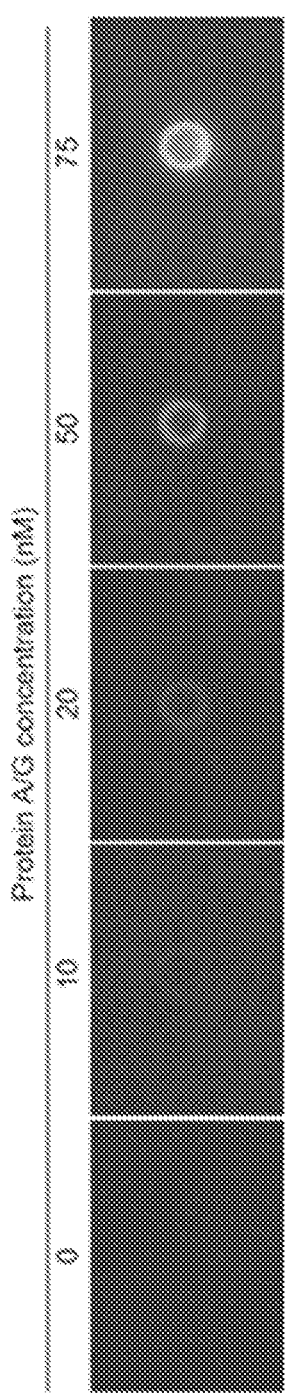
*Figure 23*
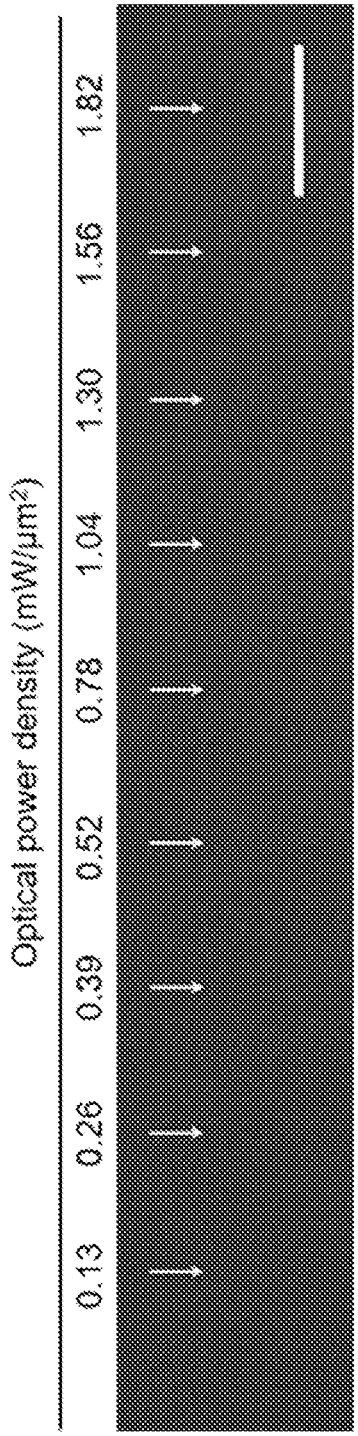
*Figure 24*
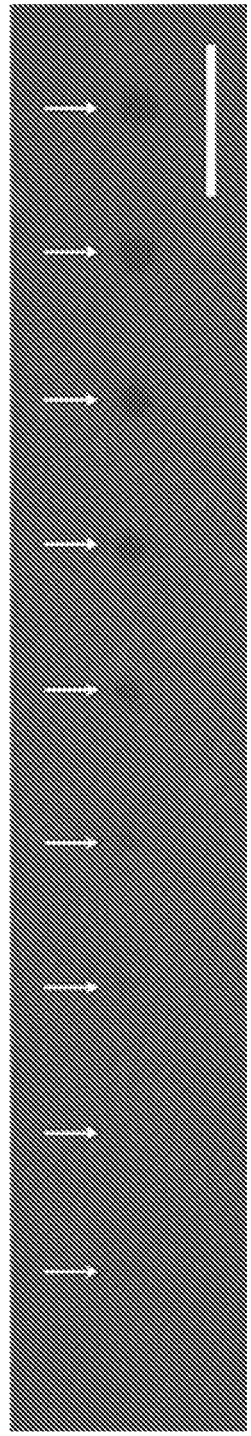

DEVICES, SYSTEMS, AND METHODS FOR ANALYTE SENSING WITH OPTOTHERMALLY GENERATED BUBBLES IN BIPHASIC LIQUID SAMPLES

CROSS-REFERENCE TO RELATED APPLICATIONS

This application is a U.S. National Stage application filed under 35 U.S.C. § 371 of PCT/US2021/040795 filed Jul. 8, 2021, which claims the benefit of priority to U.S. Provisional Application No. 63/051,132 filed Jul. 13, 2020, each of which is hereby incorporated herein by reference in its entirety.

STATEMENT OF GOVERNMENT SUPPORT

This invention was made with government support under Grant No. GM128446 awarded by the National Institutes of Health, Grant No. CMMI1761743 awarded by the National Science Foundation, and Grant No. 80NSSC17K0520 awarded by the National Aeronautics and Space Administration. The government has certain rights in the invention.

BACKGROUND

Biomolecular binding and reaction in conventional sensing systems is governed by passive diffusional transport of interacting molecules. For example, in typical sandwich-type enzyme-linked immunosorbent assay (ELISA), each surface binding step takes 30 minutes to an hour, indicating the diffusion-driven incubation process as a time-limiting step. In a gene amplification scheme for nucleic acid detection of viral infectious diseases, the low concentration of viral nucleic acid in clinical samples especially from patients at incubation period or early onset of symptoms contributes to large number of false negatives and thus community-acquired infection. Overcoming the diffusion limit in conventional platforms is critical for high-throughput and sensitive disease diagnosis. There have been preconcentration approaches including thermophoresis, electrophoresis and microbubble concentration, but the type of target analytes and applications is restricted by working conditions.

An optothermally generated surface microbubble in fluid that can quickly drive the accumulation of solutes at the bubble-surface interface due to high-velocity fluid flows has a potential as a concentrator in biosensing to overcome the diffusion limit. However, the incorporation of bubble generation into biomolecule detection is limited by fixed, high temperature required in aqueous media (>100° C.).

The devices, systems, and methods discussed herein address these and other needs.

SUMMARY

In accordance with the purposes of the disclosed devices, systems, and methods as embodied and broadly described herein, the disclosed subject matter relates to devices, systems, and methods for analyte sensing with optothermally generated bubbles in biphasic liquid samples.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The details of one or more embodiments of the invention are set forth in the accompanying drawings and description below. Other features, object, and advantages of the invention will be apparent from the description and drawings, and from the claims.

BRIEF DESCRIPTION OF THE FIGURES

The accompanying figures, which are incorporated in and constitute a part of this specification, illustrate several aspects of the disclosure, and together with the description, serve to explain the principles of the disclosure.

(FIG. 10) Schematic illustration of the bubble-generating perfluoropentane-in-water system and (FIG. 11) bubble-mediated concentration of target proteins near the bubble/substrate interface. Arrows in (FIG. 10) indicate the expansion of the perfluoropentane (PFP) droplet into the bubble.

FIG. 23. Fluorescence images of substrates after the bubble concentration of FITC-protein A/G at varying concentration (i.e., 0, 10, 20, 50, and 75 nM, from left to right).

FIG. 24. Immunobinding affinity of Immunoglobulin G coated on god nanoislands after exposure to 532 nm laser for 1 min at different optical power densities. Fluorescence images were obtained before (top panel) and after (bottom pane;) incubation with FITC-anti Immunoglobulin G (10 µg/mL) for 30 min followed by phosphate buffer saline washing. Scale bar: 10 µm. Dark regions in the bottom panel indicate less binding between Immunoglobulin G on the substrate and FITC-anti Immunoglobulin G in the solution. With increased optical power, the dark region emerges and gets larger, indicating the thermal effect on binding affinity. The laser beam diameter is around 1 µm with a gaussian distribution and does not change with respect to optical power.

(FIG. 30) 2D cross-sectional geometry of a bubble surrounded by water matrix used in the simulation and (FIG. 31) simulated temperature distribution at the bubble-liquid-substrate interface.

DETAILED DESCRIPTION

Figure 1:
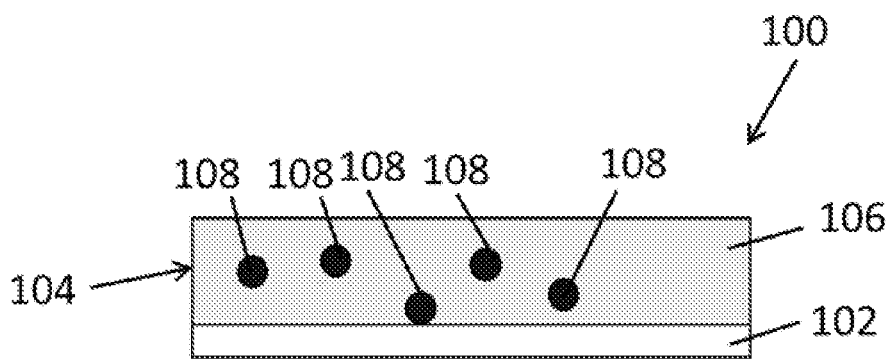
FIG. 1 is a schematic illustration of an example device as disclosed herein comprising an optothermal substrate and a biphasic liquid sample.

The devices, systems, and methods described herein may be understood more readily by reference to the following detailed description of specific aspects of the disclosed subject matter and the Examples included therein.

Before the present devices, systems, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an." and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such components, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human. Thus, the subject can be a human or veterinary patient. The term "patient" refers to a subject under the treatment of a clinician, e.g., physician.

The term "inhibit" refers to a decrease in an activity, response, condition, disease, or other biological parameter. This can include but is not limited to the complete ablation of the activity, response, condition, or disease. This can also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example. "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed. For example, the terms "prevent" or "suppress" can refer to a treatment that forestalls or slows the onset of a disease or condition or reduced the severity of the disease or condition. Thus, if a treatment can treat a disease in a subject having symptoms of the disease, it can also prevent or suppress that disease in a subject who has yet to suffer some or all of the symptoms.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder: and supportive treatment, that is, treatment employed to supplement another specific therapy directed toward the improvement of the associated disease, pathological condition, or disorder.

Methods Disclosed herein are methods comprising illuminating a first location of an optothermal substrate with electromagnetic radiation. As used herein, "a first location" and "the first location" are meant to include any number of locations in any arrangement on the optothermal substrate. Thus, for example "a first location" includes one or more first locations. In some embodiments, the first location can comprise a plurality of locations.

The electromagnetic radiation can, for example, have a power density of 0.1 mW/$\mu m^2$ or more (e.g., 0.15 mW/$\mu m^2$ or more, 0.2 mW/$\mu m^2$ or more, 0.25 mW/$\mu m^2$ or more, 0.3 mW/$\mu m^2$ or more, 0.35 mW/$\mu m^2$ or more, 0.4 mW/$\mu m^2$ or more, 0.45 mW/$\mu m^2$ or more, 0.5 mW/$\mu m^2$ or more, 0.55 mW/$\mu m^2$ or more, 0.6 mW/$\mu m^2$ or more, 0.65 mW/$\mu m^2$ or more, 0.7 mW/$\mu m^2$ or more, 0.75 mW/$\mu m^2$ or more, 0.8 mW/$\mu m^2$ or more, 0.85 mW/$\mu m^2$ or more, or 0.9 mW/$\mu m^2$ or more). In some examples, the electromagnetic radiation can have a power density of 1 mW/$\mu m^2$ or less (e.g., 0.95 mW/$\mu m^2$ or less, 0.9 mW/$\mu m^2$ or less, 0.85 mW/$\mu m^2$ or less, 0.8 mW/$\mu m^2$ or less, 0.75 mW/$\mu m^2$ or less, 0.7 mW/$\mu m^2$ or less, 0.65 mW/$\mu m^2$ or less, 0.6 mW/$\mu m^2$ or less, 0.55 mW/$\mu m^2$ or less, 0.5 mW/$\mu m^2$ or less, 0.45 mW/$\mu m^2$ or less, 0.4 mW/$\mu m^2$ or less, 0.35 mW/$\mu m^2$ or less, 0.3 mW/$\mu m^2$ or less, 0.25 mW/$\mu m^2$ or less, or 0.2 mW/$\mu m^2$ or less). The power density of the electromagnetic radiation can range from any of the minimum values described above to any of the maximum values described above. For example, the electromagnetic radiation can have a power density of from 0.1 mW/$\mu m^2$ to 1 mW/$\mu m^2$ (e.g., from 0.1 mW/$\mu m^2$ to 0.55 mW/$\mu m^2$, from 0.55 mW/$\mu m^2$ to 1 mW/$\mu m^2$, from 0.1 mW/$\mu m^2$ to 0.4 mW/$\mu m^2$, from 0.4 mW/$\mu m^2$ to 0.7 mW/$\mu m^2$, from 0.7 mW/$\mu m^2$ to 1 mW/$\mu m^2$, from 0.1 mW/$\mu m^2$ to 0.9 mW/$\mu m^2$, from 0.2 mW/$\mu m^2$ to 1 mW/$\mu m^2$, from 0.2 mW/$\mu m^2$ to 0.9 mW/$\mu m^2$, from 0.1 mW/$\mu m^2$ to 0.5 mW/$\mu m^2$, or from 0.2 mW/$\mu m^2$ to 0.3 mW/$\mu m^2$).

The electromagnetic radiation can, for example, be provided by a light source. The light source can be any type of light source. Examples of suitable light sources include natural light sources (e.g., sunlight) and artificial light sources (e.g., incandescent light bulbs, light emitting diodes, gas discharge lamps, arc lamps, lasers etc.). In some examples, the light source is a laser, such as a continuous wave laser.

In some examples, the light source is configured to illuminate a mirror, the mirror being configured to reflect the electromagnetic radiation from the light source to illuminate the first location of the optothermal substrate. In some examples, the mirror can comprise a plurality of mirrors, such as an array of micromirrors (e.g., a digital micromirror device).

As used herein, an optothermal substrate is any substrate that can convert at least a portion of the electromagnetic radiation into thermal energy. For example, the optothermal substrate can comprise a material with a high absorption efficiency at one or more wavelengths that overlaps with at least a portion of the electromagnetic radiation.

In some examples, the optothermal substrate can comprise an optothermal material disposed on substrate, such as a transparent substrate. As used herein, a "transparent substrate" is meant to include any substrate that is transparent at the wavelength or wavelength region of interest. Examples of substrates include, but are not limited to, glass, quartz, parylene, silicon dioxide, mica, poly(methyl methacrylate), polyamide, polycarbonate, polyester, polypropylene, polytetrafluoroethylene, poly dimethylsiloxane (PDMS), hafnium oxide, hafnium silicate, tantalum pentoxide, zirconium dioxide, zirconium silicate, and combinations thereof. The substrate can, for example, comprise glass, quartz, silicon dioxide, silicon nitride, a polymer, or a combination thereof.

In some examples, the optothermal substrate can comprise a carbon material. Examples of carbon materials include, but are not limited to, graphitic carbon and graphites, including pyrolytic graphite (e.g., highly ordered pyrolytic graphite (HOPG)) and isotropic graphite, amorphous carbon, carbon black, single- or multi-walled carbon nanotubes, graphene, glassy carbon, diamond-like carbon (DLC) or doped DLC, such as boron-doped diamond, pyrolyzed photoresist films, and others known in the art. In some examples, the optothermal substrate can include an organic dye, such as indocyanine green.

The optothermal substrate can, for example, comprise a plasmonic substrate, a metal film, or a combination thereof. In some examples, the optothermal substrate comprises a plasmonic substrate and the electromagnetic radiation comprises a wavelength that overlaps with at least a portion of the plasmon resonance energy of the substrate.

The plasmonic substrate can, for example, comprise a plasmonic material. Examples of plasmonic materials include, but are not limited to, plasmonic metals, plasmonic semiconductors (e.g., silicon carbide), doped semiconductors (e.g., aluminum-doped zinc oxide), transparent conducting oxides, perovskites, metal nitrides, metal oxides, silicides, germanides, two-dimensional plasmonic materials (e.g., graphene), and combinations thereof.

The plasmonic substrate can, in some examples, comprise a plurality of plasmonic particles. In some examples, the plurality of plasmonic particles can comprise a plurality of metal particles. The plurality of metal particles can, for example, comprise a metal selected from the group consisting of Au, Ag, Pd, Cu. Cr, Al, and combinations thereof. In some examples, the plurality of plasmonic particles can comprise a plurality of gold particles.

The plurality of plasmonic particles can have an average particle size. "Average particle size" and "mean particle size" are used interchangeably herein, and generally refer to the statistical mean particle size of the particles in a population of particles. For example, the average particle size for a plurality of particles with a substantially spherical shape can comprise the average diameter of the plurality of particles. For a particle with a substantially spherical shape, the diameter of a particle can refer, for example, to the hydrodynamic diameter. As used herein, the hydrodynamic diameter of a particle can refer to the largest linear distance between two points on the surface of the particle. Mean particle size can be measured using methods known in the art, such as evaluation by scanning electron microscopy, transmission electron microscopy, and/or dynamic light scattering.

The plurality of plasmonic particles have, for example, an average particle size of 2 nm or more (e.g., 3 nm or more, 4 nm or more, 5 nm or more, 6 nm or more, 7 nm or more, 8 nm or more, 9 nm or more, 10 nm or more, 15 nm or more, 20 nm or more, 25 nm or more, 30 nm or more, 35 nm or more, 40 nm or more, 45 nm or more, 50 nm or more, 55 nm or more, 60 nm or more, 65 nm or more, 70 nm or more, 75 nm or more, 80 nm or more, 85 nm or more, 90 nm or more, 95 nm or more, 100 nm or more, 110 nm or more, 120 nm or more, 130 nm or more, 140 nm or more, 150 nm or more, 160 nm or more, 170 nm or more, 180 nm or more, 190 nm or more, 200 nm or more, 210 nm or more, 220 nm or more, 230 nm or more, 240 nm or more, 250 nm or more, 260 nm or more, 270 nm or more, 280 nm or more, or 290 nm or more). In some examples, the plurality of plasmonic particles can have an average particle size of 300 nm or less (e.g., 290 nm or less, 280 nm or less, 270 nm or less, 260 nm or less, 250 nm or less, 240 nm or less, 230 nm or less, 220 nm or less, 210 nm or less, 200 nm or less, 190 nm or less, 180 nm or less, 170 nm or less, 160 nm or less, 150 nm or less, 140 nm or less, 130 nm or less, 120 nm or less, 110 nm or less, 100 nm or less, 95 nm or less, 90 nm or less, 85 nm or less, 80 nm or less, 75 nm or less, 70 nm or less, 65 nm or less, 60 nm or less, 55 nm or less, 50 nm or less, 45 nm or less, 40 nm or less, 35 nm or less, 30 nm or less, 25 nm or less, 20 nm or less, 15 nm or less, 10 nm or less, 9 nm or less, 8 nm or less, 7 nm or less, 6 nm or less, or 5 nm or less). The average particle size of the plurality of plasmonic particles can range from any of the minimum values described above to any of the maximum values described above. For example, the plurality of plasmonic particles can have an average particle size of from 2 nm to 300 nm (e.g., from 2 nm to 150 nm, from 150 nm to 300 nm, from 2 nm to 100 nm, from 100 nm to 200 nm, from 200 nm to 300 nm, or from 2 nm to 200 nm).

In some examples, the plurality of plasmonic particles can be substantially monodisperse. "Monodisperse" and "homogeneous size distribution." as used herein, and generally describe a population of particles where all of the particles are the same or nearly the same size. As used herein, a monodisperse distribution refers to particle distributions in which 80% of the distribution (e.g., 85% of the distribution, 90% of the distribution, or 95% of the distribution) lies within 25% of the median particle size (e.g., within 20% of the median particle size, within 15% of the median particle size, within 10% of the median particle size, or within 5% of the median particle size).

The plurality of plasmonic particles can comprise particles of any shape (e.g., a sphere, a rod, a quadrilateral, an ellipse, a triangle, a polygon, etc.). In some examples, the plurality of plasmonic particles can have a regular shape, an irregular shape, an isotropic shape, an anisotropic shape, or a combination thereof. In some examples, the plurality of plasmonic particles are substantially spherical.

In some examples, each plasmonic particle within the plurality of plasmonic particles on the substrate can be separated from its neighboring plasmonic particles by an average distance of 1 nm or more (e.g., 2 nm or more, 3 nm or more, 4 nm or more, 5 nm or more, 6 nm or more, 7 nm or more, 8 nm or more, 9 nm or more, 10 nm or more, 11 nm or more, 12 nm or more, 13 nm or more, 14 nm or more, 15 nm or more, 16 nm or more, 17 nm or more, 18 nm or more, 19 nm or more, 20 nm or more, 25 nm or more, 30 nm or more, 35 nm or more, 40 nm or more, 45 nm or more, 50 nm or more, 55 nm or more, 60 nm or more, 65 nm or more, 70 nm or more, 75 nm or more, 80 nm or more, 85 nm or more, 90 nm or more, or 95 nm or more). In some examples, each plasmonic particle within the plurality of plasmonic particles on the substrate can be separated from its neighboring plasmonic particles by an average distance of 100 nm or less (e.g., 95 nm or less, 90 nm or less, 85 nm or less, 80 nm or less, 75 nm or less, 70 nm or less, 65 nm or less, 60 nm or less, 55 nm or less, 50 nm or less, 45 nm or less, 40 nm or less, 35 nm or less, 30 nm or less, 25 nm or less, 20 nm or less, 19 nm or less, 18 nm or less, 17 nm or less, 16 nm or less, 15 nm or less, 14 nm or less, 13 nm or less, 12 nm or less, 11 nm or less, 10 nm or less, 9 nm or less, 8 nm or less, 7 nm or less, 6 nm or less, or 5 nm or less). The average distance that each plasmonic particle within the plurality of plasmonic particles on the substrate is separated from its neighboring plasmonic particles can range from any of the minimum values described above to any of the maximum values described above. For example, each plasmonic particle within the plurality of plasmonic particles on the substrate is separated from its neighboring plasmonic particles by an average distance of from 1 nm to 100 nm (e.g., from 1 nm to 50 nm, from 50 nm to 100 nm, from 1 nm to 20 nm, from 20 nm to 40 nm, from 40 nm to 60 nm, from 60 nm to 80 nm, from 80 nm to 100 nm, from 1 nm to 40 nm, from 1 nm to 30 nm, or from 1 nm to 20 nm).

In some examples, the density of the plurality of plasmonic particles on the plasmonic substrate can be $10^{10}$ particles/cm$^2$ or more (e.g., $1.25 \times 10^{10}$ particles/cm$^2$ or more, $1.5 \times 10^{10}$ particles/cm$^2$ or more, $1.75 \times 10^{10}$ particles/cm$^2$ or more, $2 \times 10^{10}$ particles/cm$^2$ or more, $2.25 \times 10^{10}$ particles/cm$^2$ or more, $2.5 \times 10^{10}$ particles/cm$^2$ or more, $2.75 \times 10^{10}$ particles/cm$^2$ or more, $3 \times 10^{10}$ particles/cm$^2$ or more, $3.25 \times 10^{10}$ particles/cm$^2$ or more, $3.5 \times 10^{10}$ particles/cm$^2$ or more, $3.75 \times 10^{10}$ particles/cm$^2$ or more, $4 \times 10^{10}$ particles/cm$^2$ or more, $4.25 \times 10^{10}$ particles/cm$^2$ or more, $4.5 \times 10^{10}$ particles/cm$^2$ or more, $4.75 \times 10^{10}$ particles/cm$^2$ or more, $5 \times 10^{10}$ particles/cm$^2$ or more, $5.25 \times 10^{10}$ particles/cm$^2$ or more, $5.5 \times 10^{10}$ particles/cm$^2$ or more, $5.75 \times 10^{10}$ particles/cm$^2$ or more, $6 \times 10^{10}$ particles/cm$^2$ or more, $6.25 \times 10^{10}$ particles/cm$^2$ or more, $6.5 \times 10^{10}$ particles/cm$^2$ or more, $6.75 \times 10^{10}$ particles/cm$^2$ or more, $7 \times 10^{10}$ particles/cm$^2$ or more, $7.25 \times 10^{10}$ particles/cm$^2$ or more, $7.5 \times 10^{10}$ particles/cm$^2$ or more, $7.75 \times 10^{10}$ particles/cm$^2$ or more, $8 \times 10^{10}$ particles/cm$^2$ or more, $8.25 \times 10^{10}$ particles/cm$^2$ or more, $8.5 \times 10^{10}$ particles/cm$^2$ or more, $8.75 \times 10^{10}$ particles/cm$^2$ or more, $9 \times 10^{10}$ particles/cm$^2$ or more, $9.25 \times 10^{10}$ particles/cm$^2$ or more, $9.5 \times 10^{10}$ particles/cm$^2$ or more, or $9.75 \times 10^{10}$ particles/cm$^2$ or more). In some examples, the density of the plurality of plasmonic particles on the plasmonic substrate can be $10^{11}$ particles/cm$^2$ or less (e.g., $9.75 \times 10^{10}$ particles/cm$^2$ or less, $9.5 \times 10^{10}$ particles/cm$^2$ or less, $9.25 \times 10^{10}$ particles/cm$^2$ or less, $9 \times 10^{10}$ particles/cm$^2$ or less, $8.75 \times 10^{10}$ particles/cm$^2$ or less, $8.5 \times 10^{10}$ particles/cm$^2$ or less, $8.25 \times 10^{10}$ particles/cm$^2$ or less, $8 \times 10^{10}$ particles/cm$^2$ or less, $7.75 \times 10^{10}$ particles/cm$^2$ or less, $7.5 \times 10^{10}$ particles/cm$^2$ or less, $7.25 \times 10^{10}$ particles/cm$^2$ or less, $7 \times 10^{10}$ particles/cm$^2$ or less, $6.75 \times 10^{10}$ particles/cm$^2$ or less, $6.5 \times 10^{10}$ particles/cm$^2$ or less, $6.25 \times 10^{10}$ particles/cm$^2$ or less, $6 \times 10^{10}$ particles/cm$^2$ or less, $5.75 \times 10^{10}$ particles/cm$^2$ or less, $5.5 \times 10^{10}$ particles/cm$^2$ or less, $5.25 \times 10^{10}$ particles/cm$^2$ or less, $5 \times 10^{10}$ particles/cm$^2$ or less, $4.75 \times 10^{10}$ particles/cm$^2$ or less, $4.5 \times 10^{10}$ particles/cm$^2$ or less, $4.25 \times 10^{10}$ particles/cm$^2$ or less, $4 \times 10^{10}$ particles/cm$^2$ or less, $3.75 \times 10^{10}$ particles/cm$^2$ or less, $3.5 \times 10^{10}$ particles/cm$^2$ or less, $3.25 \times 10^{10}$ particles/cm$^2$ or less, $3 \times 10^{10}$ particles/cm$^2$ or less, $2.75 \times 10^{10}$ particles/cm$^2$ or less, $2.5 \times 10^{10}$ particles/cm$^2$ or less, $2.25 \times 10^{10}$ particles/cm$^2$ or less, $2 \times 10^{10}$ particles/cm$^2$ or less, $1.75 \times 10^{10}$ particles/cm$^2$ or less, $1.5 \times 10^{10}$ particles/cm$^2$ or less, or $1.25 \times 10^{10}$ particles/cm$^2$ or less). The density of the plurality of plasmonic particles on the plasmonic substrate can range from any of the minimum values described above to any of the maximum values described above. For example, the density of the plurality of plasmonic particles on the plasmonic substrate can be from $10^{10}$ particles/cm$^2$ to $10^{11}$ particles/cm$^2$ (e.g., from $1 \times 10^{10}$ particles/cm$^2$ to $5 \times 10^{10}$ particles/cm$^2$, from $5 \times 10^{10}$ particles/cm$^2$ to $1 \times 10^{11}$ particles/cm$^2$, from $1 \times 10^{10}$ particles/cm$^2$ to $2.5 \times 10^{10}$ particles/cm$^2$, from $2.5 \times 10^{10}$ particles/cm$^2$ to $5 \times 10^{10}$ particles/cm$^2$, from $5 \times 10^{10}$ particles/cm$^2$ to $7.5 \times 10^{10}$ particles/cm$^2$, from $7.5 \times 10^{10}$ particles/cm$^2$ to $1 \times 10^{11}$ particles/cm$^2$, or from $2 \times 10^{10}$ particles/cm$^2$ to $9 \times 10^{10}$ particles/cm$^2$).

The size, shape, and/or composition of the plurality of plasmonic particles; the separation between each particle within the plurality of plasmonic particles; the density of the plasmonic particles on the substrate; or combinations thereof can be selected in view of a variety of factors. In some examples, the size, shape, and/or composition of the plurality of plasmonic particles can be selected to maximize the electromagnetic field enhancement. For example, the size, shape, and/or composition of the plurality of plasmonic particles; the separation between each particle within the plurality of plasmonic particles; the density of the plasmonic particles on the substrate; or combinations thereof can be selected such that the intensity of an incident electromagnetic field is enhanced by a factor of 5 or more by the plurality of plasmonic particles (e.g., 10 or more, 20 or more, 30 or more, 40 or more, 50 or more, 60 or more 70 or more, 80 or more, 90 or more, or 100 or more). In some examples, the size, shape, and/or composition of the plurality of plasmonic particles; the separation between each particle within the plurality of plasmonic particles: the density of the plasmonic particles on the substrate: or combinations thereof can be selected such that the plasmon resonance energy of the plasmonic substrate overlaps with at least a portion of the electromagnetic radiation used to illuminate the plasmonic substrate.

The methods can further comprise, for example, making the plasmonic substrate by depositing the plurality of plasmonic particles on a substrate. Depositing the plurality of plasmonic particles can comprise, for example, printing, lithographic deposition, electron beam deposition, thermal deposition, spin coating, drop-casting, zone casting, dip coating, blade coating, spraying, vacuum filtration, or combinations thereof.

The methods can further comprise, for example, making the plasmonic substrate by thermally annealing a film of a plasmonic metal deposited on a substrate, thereby forming the plurality of plasmonic particles on the substrate. In some examples, the methods can further comprise depositing the film of the plasmonic metal on the substrate. The film of plasmonic metal can be deposited on the substrate, for example, by thin film processing techniques, such as sputtering, pulsed layer deposition, molecular beam epitaxy, evaporation, atomic layer deposition, or combinations thereof. In some examples, the film of the plasmonic metal can have an average thickness of 2 nm or more (e.g., 2.5 nm or more, 3 nm or more, 3.5 nm or more, 4 nm or more, 4.5 nm or more, 5 nm or more, 5.5 nm or more, 6 nm or more, 6.5 nm or more, 7 nm or more, 7.5 nm or more, 8 nm or more, 8.5 nm or more, 9 nm or more, 9.5 nm or more, 10 nm or more, II nm or more, 12 nm or more, 13 nm or more, 14 nm or more, 15 nm or more, 20 nm or more, 25 nm or more, 30 nm or more, 35 nm or more, 40 nm or more, 45 nm or more, 50 nm or more, 60 nm or more, 70 nm or more, 80 nm or more, or 90 nm or more). In some examples, the film of the plasmonic metal can have an average thickness of 100 nm or less (e.g., 90 nm or less, 80 nm or less, 70 nm or less, 60 nm or less, 50 nm or less, 45 nm or less, 40 nm or less, 35 nm or less, 30 nm or less, 25 nm or less, 20 nm or less, 15 nm or less, 14 nm or less, 13 nm or less, 12 nm or less, 11 nm or less, 10 nm or less, 9.5 nm or less, 9 nm or less, 8.5 nm or less, 8 nm or less, 7.5 nm or less, 7 nm or less, 6.5 nm or less, 6 nm or less, 5.5 nm or less, 5 nm or less, 4.5 nm or less, 4 nm or less, 3.5 nm or less, 3 nm or less, or 2.5 nm or less). The average thickness of the film of the plasmonic metal can range from any of the minimum values described above to any of the maximum values described above. For example, the film of the plasmonic metal can have an average thickness of from 2 nm to 100 nm (e.g., from 2 nm to 50 nm, from 50 nm to 100 nm, from 2 nm to 20 nm, from 20 nm to 40 nm, from 40 nm to 60 nm, from 60 nm to 80 nm, from 2 nm to 90 nm, from 5 nm to 100 nm, from 5 nm to 90 nm, from 2 nm to 80 nm, from 2 nm to 60 nm, from 2 nm to 40 nm, or from 2 nm to 15 nm.

Thermally annealing the film can, for example, comprise heating the film at a temperature of 300° C. or more (e.g., 310° C. or more, 320° C. or more, 330° C. or more, 340° C. or more, 350° C. or more, 360° C. or more, 370° C. or more, 380° C. or more, 390° C. or more, 400° C. or more, 410° C. or more, 420° C. or more, 430° C. or more, 440° C. or more, 450° C. or more, 460° C. or more, 470° C. or more, 480° C. or more, 490° C. or more, 500° C. or more, 510° C. or more, 520° C. or more, 530° C. or more, 540° C. or more, 550° C. or more, 560° C. or more, 570° C. or more, 580° C. or more, or 590° C. or more). In some examples, thermally annealing the film can comprise heating the film at a temperature of 600° C. or less (e.g., 590° C. or less, 580° C. or less, 570° C. or less, 560° C. or less, 550° C. or less, 540° C. or less, 530° C. or less, 520° C. or less, 510° C. or less, 500° C. or less, 490° C. or less, 480° C. or less, 470° C. or less, 460° C. or less, 450° C. or less, 440° C. or less, 430° C. or less, 420° C. or less, 410° C. or less, 400° C. or less, 390° C. or less, 380° C. or less, 370° C. or less, 360° C. or less, 350° C. or less, 340° C. or less, 330° C. or less, 320° C. or less, or 310° C. or less). The temperature at which the film is heated during thermal annealing can range from any of the minimum values described above to any of the maximum values described above. For example, thermally annealing the film can comprise heating the film at a temperature of from 300° C. to 600° C. (e.g., from 300° C. to 450° C., from 450° C. to 600° C., from 300° C. to 400° C., from 400° C. to 500° C., from 500° C. to 600° C., from 400° C. to 600° C., from 450° C. to 600° C. or from 530° C. to 570° C.). In some examples, thermally annealing the film can comprise heating the film at a temperature of 550° C.

In some examples, the film can be thermally annealed for 1 hour or more (e.g., 1.5 hours or more, 2 hours or more, 2.5 hours or more, 3 hours or more, 3.5 hours or more, 4 hours or more, 4.5 hours or more, 5 hours or more, 5.5 hours or more, 6 hours or more, 6.5 hours or more, 7 hours or more, 7.5 hours or more, 8 hours or more, 8.5 hours or more, 9 hours or more, 9.5 hours or more, 10 hours or more, 10.5 hours or more, 11 hours or more, or 11.5 hours or more). In some examples, the film can be thermally annealed for 12 hours or less (e.g., 11.5 hours or less, 11 hours or less, 10.5 hours or less, 10 hours or less, 9.5 hours or less, 9 hours or less, 8.5 hours or less, 8 hours or less, 7.5 hours or less, 7 hours or less, 6.5 hours or less, 6 hours or less, 5.5 hours or less, 5 hours or less, 4.5 hours or less, 4 hours or less, 3.5 hours or less, 3 hours or less, 2.5 hours or less, 2 hours or less, or 1.5 hours or less). The time for which the film can be thermally annealed can range from any of the minimum values described above to any of the maximum values described above. For example, the film can be thermally annealed for from 1 hour to 12 hours (e.g., from 1 hour to 6 hours, from 6 hours to 12 hours, from 1 hour to 4 hours, from 4 hours to 8 hours, from 8 hours to 12 hours, from 1 hour to 10 hours, or from 1 hour to 3 hours). In some examples, the film can be thermally annealed for 2 hours.

In some examples, the optothermal substrate can comprise a metal film, such as a metal film deposited on a substrate. The metal film can, for example, comprise a metal selected from the group consisting of Be, Mg, Al, Ca, Sc, Ti, V, Cr, Mn, Fe, Co, Ni, Cu, Zn, Ga, Sr, Y, Zr, Nb, Mo, Tc, Ru, Rh, Pd, Ag, Cd, In, Sn, Ba, Hf, Ta, W, Re, Os, Ir, Pt, Au, Hg, Tl, Pb, Bi, La, Ce, Pr, Nd, Pm, Sm, Eu, Gd, Tb, Dy, Ho, Er, Tm, Yb, and combinations thereof. In some examples, the metal film can comprise a metal selected from the group consisting of Al, Ti, Cr, Mn, Fe, Co, Ni, Cu, Mo, Pd, Ag, Cd, Pt, Au, and combinations thereof. In some examples, the methods can further comprise making the optothermal substrate by depositing the metal film on a substrate. The metal film can be deposited on the substrate, for example, by thin film processing techniques, such as sputtering, pulsed layer deposition, molecular beam epitaxy, evaporation, thermal deposition, atomic layer deposition, or combinations thereof.

The metal film can, for example, have an average thickness of 2 nm or more (e.g., 3 nm or more, 4 nm or more, 5 nm or more, 6 nm or more, 7 nm or more, 8 nm or more, 9 nm or more, 10 nm or more, 15 nm or more, 20 nm or more, 25 nm or more, 30 nm or more, 35 nm or more, 40 nm or more, 45 nm or more, 50 nm or more, 60 nm or more, 70 nm or more, 80 nm or more, 90 nm or more, 100 nm or more, 125 nm or more, 150 nm or more, or 175 nm or more). In some examples, the metal film can have an average thickness of 200 nm or less (e.g., 175 nm or less, 150 nm or less, 125 nm or less, 100 nm or less, 90 nm or less, 80 nm or less, 70 nm or less, 60 nm or less, 50 nm or less, 45 nm or less, 40 nm or less, 35 nm or less, 30 nm or less, 25 nm or less, 20 nm or less, 15 nm or less, 10 nm or less, 9 nm or less, 8 nm or less, 7 nm or less, 6 nm or less, 5 nm or less, 4 nm or less, or 3 nm or less). The average thickness of the metal film can range from any of the minimum values described above to any of the maximum values described above. For example, the metal film can have an average thickness of from 2 nm to 200 nm (e.g., from 2 nm to 100 nm, from 100 nm to 200 nm, from 2 nm to 50 nm, from 50 nm to 100 nm, from 100 nm to 150 nm, from 150 nm to 200 nm, from 10 nm to 150 nm, or from 2 nm to 10 nm).

In some examples, the optothermal substrate can further comprise an antifouling layer. For example, the antifouling layer can comprise a zwitterionic compound, a PEGylated compound, or a combination thereof. Examples of zwitterionic compounds include, but are not limited to, phosphatidylcholine, zwitterionic polymers, and combinations thereof. In some examples, the antifouling layer is not damaged during the method.

The optothermal substrate is in thermal contact with a biphasic liquid sample comprising an aqueous solution and one or more droplets comprising a water-immiscible liquid dispersed in the aqueous solution. The aqueous solution comprises water and a plurality of analytes. In some examples, the aqueous solution can further comprise an additional solvent, such as comprise tetrahydrofuran (THF), N-methyl-2-pyrrolidone (NMP), dimethylformamide (DMF), N-methylformamide, formamide, ethylene glycol, polyethylene glycol, glycerol, alkane diol, ethanol, methanol, propanol, isopropanol, acetonitrile, acetone, tetraglyme, propylene carbonate, diglyme, dimethyl sulfoxide (DMSO), dimethoxyethane, dimethylacetamide, or combinations thereof.

The aqueous solution can comprise any aqueous solution of interest. In some examples, the aqueous solution can comprise a phosphate buffer saline solution. In some examples, the aqueous solution can comprise a bodily fluid. "Bodily fluid", as used herein, refers to a fluid composition obtained from or located within a human or animal subject. Bodily fluids include, but are not limited to, urine, whole blood, blood plasma, serum, tears, semen, saliva, sputum, exhaled breath, nasal secretions, pharyngeal exudates, bronchoalveolar lavage, tracheal aspirations, interstitial fluid, lymph fluid, meningeal fluid, amniotic fluid, glandular fluid, feces, perspiration, mucous, vaginal or urethral secretion, cerebrospinal fluid, and transdermal exudate. Bodily fluid also includes experimentally separated fractions of all of the preceding solutions, as well as mixtures containing homogenized solid material, such as feces, tissues, and biopsy samples. In some examples, the bodily fluid comprises urine, plasma, blood, or a combination thereof.

The plurality of analytes can comprise any analyte of interest. The plurality of analytes can, for example, comprise a biomolecule, a macromolecule, a pathogen (e.g., bacteria, virus, fungi, or protozoa), a drug, or a combination thereof. As used herein, a biomolecule can comprise, for example, a nucleotide, an enzyme, an amino acid, a protein (e.g., a glycoprotein, a lipoprotein, or a recombinant protein), a polysaccharide, a lipid, a nucleic acid, a vitamin, a hormone, a prohormone, a peptide (natural, modified, or chemically synthesized), a polypeptide, polynucleotide (e.g., DNA or RNA, an oligonucleotide, an aptamer, or a DNAzyme), or a combination thereof. In some examples, the plurality of analytes can comprise a macromolecule, such as a cyclodextrins, calixarenes, cucurbiturils, crown ethers, cyclophanes, cryptands, nanotubes, fullerenes, and dendrimers. In some examples, the plurality of analytes can comprise a biomarker (i.e., a molecular indicator associated with a particular pathological or physiological state). Examples of biomarkers include proteins, peptides, polypeptides, hormones, prohormones, lipids, glycoproteins, carbohydrates, DNA, RNA, and combinations thereof.

In some examples, the plurality of analytes can comprise an enzyme, a protein, or a combination thereof. In some examples, the plurality of analytes can comprise a pathogen (e.g., bacteria, virus, fungi, parasite, or protozoa), a biomarker indicative of a pathogen, or a combination thereof. In some examples, the plurality of analytes can comprise a pathogen, an antibody, or a combination thereof. In some examples, the plurality of analytes can comprise a virus, an antibody for a virus, or a combination thereof.

Viruses that are suitable for the methods and uses described herein can include both DNA viruses and RNA viruses. Exemplary viruses can belong to the following non-exclusive list of families Adenoviridae, Arenaviridae, Astroviridae, Baculoviridae, Barnaviridae, Betaherpesvirinae, Bimaviridae, Bromoviridae, Bunyaviridae, Caliciviridae, Chordopoxvirinae, Circoviridae, Comoviridae, Coronaviridae, Cystoviridae, Corticoviridae, Entomopoxvirinae, Filoviridae, Flaviviridae, Fuselloviridae, Geminiviridae, Hepadnaviridae, Herpesviridae, Gammaherpesvirinae, Inoviridae, Iridoviridae, Leviviridae, Lipothrixviridae, Microviridae, Myoviridae, Nodaviridae, Orthomyxoviridae, Papovaviridae, Paramyxoviridae, Paramyxovirinae, Partitiviridae, Parvoviridae, Phycodnaviridae, Picomaviridae, Plasmaviridae, Pneumovirinae, Podoviridae, Polydnaviridae, Potyviridae, Poxviridae, Reoviridae, Retroviridae, Rhabdoviridae, Sequiviridae, Siphoviridae, Tectiviridae, Tetraviridae, Togaviridae, Tombusviridae, and Totiviridae.

Specific examples of viruses include, but are not limited to, Mastadenovirus, Adenovirus. Human adenovirus 2, Aviadenovirus, African swine fever virus, arenavirus. Lymphocytic choriomeningitis virus, Ippy virus, Lassa virus, Arterivirus, Human astrovirus 1, Nucleopolyhedrovirus, *Autographa californica* nucleopolyhedrovirus, Granulovirus, Plodia interpunctella granulovirus, Badnavirus, *Commelina* yellow mottle virus, Rice tungro bacilliform, Bamavirus, Mushroom bacilliform virus, Aquabimavirus, Infectious pancreatic necrosis virus, Avibimavirus, Infectious bursal disease virus, Entomobimavirus, *Drosophila* X virus, Alfamovirus, Alfalfa mosaic virus, Ilarvirus, Ilarvirus Subgroups 1-10, Tobacco streak virus, Bromovirus, Brome mosaic virus, Cucumovirus. Cucumber mosaic virus, Bhanja virus Group, Kaisodi virus, Mapputta virus, Okola virus, Resistencia virus, Upolu virus, Yogue virus. Bunyaavirus, *Anopheles* A virus, *Anopheles* B virus, Bakau virus, Bunyamwera virus, Bwamba virus, C virus, California encephalitis virus, Capim virus, Gamboa virus, Guama virus, Koongol virus, Minatitlan virus, Nyando virus, Olifantsvlei virus, Patois virus, Simbu virus, Tete virus. Turlock virus, Hantavirus, Hantaan virus, Nairovirus, Crimean-Congo hemorrhagic fever virus, Dera Ghazi Khan virus, Hughes virus, Nairobi sheep disease virus, Qalyub virus, Sakhalin virus, Thiafora virus, Crimean-congo hemorrhagic fever virus, Phlebovirus, Sandfly fever virus, Bujaru complex, Candiru complex. Chilibre complex, Frijoles complex, Punta Toro complex, Rift Valley fever complex, Salehabad complex, Sandfly fever Sicilian virus, Uukuniemi virus, Uukuniemi virus, Tospovirus, Tomato spotted wilt virus, Calicivirus, Vesicular exanthema of swine virus, Capillovirus, Apple stem grooving virus. Carlavirus, Carnation latent virus, Caulimovirus, Cauliflower mosaic virus, Circovirus, Chicken anemia virus, Closterovirus, Beet yellows virus, Comovirus, Cowpea mosaic virus, Fabavirus, Broad bean wilt virus 1, Nepovirus, Tobacco ringspot virus, Coronavirus, Avian infectious bronchitis virus, Bovine coronavirus, Canine coronavirus, Feline infectious peritonitis virus, Human coronavirus 299E, Human coronavirus OC43. Murine hepatitis virus, Porcine epidemic diarrhea virus, Porcine hemagglutinating encephalomyelitis virus, Porcine transmissible gastroenteritis virus, Rat coronavirus. Turkey coronavirus. Rabbit coronavirus, Torovirus, Berne virus, Breda virus, Corticovirus, *Alteromonas* phage PM2, *Pseudomonas* Phage phi6, Deltavirus. Hepatitis delta virus, Hepatitis D virus, Hepatitis E virus, Dianthovirus, Carnation ringspot virus, Red clover necrotic mosaic virus, Sweet clover necrotic mosaic virus, Enamovirus, Pea enation mosaic virus, Filovirus, Marburg virus, Ebola virus, Ebola virus Zaire. Flavivirus, Yellow fever virus, Tick-borne encephalitis virus, Rio Bravo Group, Japanese encephalitis, Tyuleniy Group, Ntaya Group, Uganda S Group, Dengue Group, Modoc Group, Pestivirus, Bovine diarrhea virus, Hepatitis C virus. Furovirus, Soil-borne wheat mosaic virus, Beet necrotic yellow vein virus, Fusellovirus, Sulfobolus virus 1, Subgroup I, II, and III geminivirus, Maize streak virus, Beet curly top virus, Bean golden mosaic virus, Orthohepadnavirus, Hepatitis B virus, Avihepadnavirus, Alphaherpesvirinae, Simplexvirus, Human herpesvirus 1, Herpes Simplex virus-1, Herpes Simplex virus-2, Varicellovirus, Varicella-Zoster virus, Epstein-Barr virus. Human herpesvirus 3, Cytomegalovirus, Human herpesvirus 5, Muromegalovirus, Mouse cytomegalovirus 1, Roseolovirus, Human herpesvirus 6, Lymphocryptovirus, Human herpesvirus 4, Rhadinovirus, Ateline herpesvirus 2, Hordeivirus, Barley stripe mosaic virus, Hypoviridae, Hypovirus, *Cryphonectria* hypovirus 1-EP713, Idaeovirus, Raspberry bushy dwarf virus, Inovirus, Coliphage fd, Plectrovirus, Acholeplasma phage L51, Iridovirus, *Chilo* iridescent virus, Chloriridovirus, Mosquito iridescent virus, Ranavirus, Frog virus 3, Lymphocystivirus. Lymphocystis disease virus flounder isolate, Goldfish virus 1, Levivirus, Enterobacteria phage MS2, Allolevirus, Enterobacteria phage Qbeta, Lipothrixvirus, Thermoproteus virus 1, Luteovirus, Barley yellow dwarf virus, Machlomovirus, Maize chlorotic mottle virus, Marafivirus. Maize rayado fino virus, Microvirus, Coliphage phiX174, Spiromicrovirus, Spiroplasma phage 4, Bdellomicrovirus, Bdellovibrio phage MAC 1, Chlamydia-microvirus, *Chlamydia* phage 1, T4-like phages, coliphage T4, Necrovirus, Tobacco necrosis virus, Nodavirus, Nodamura virus, Influenzavirus A. B and C. Thogoto virus, Polyomavirus, Murine polyomavirus, Papillomavirus, Rabbit (Shope) Papillomavirus, Paramyxovirus, Human parainfluenza virus 1, Morbillivirus. Measles virus, Rubulavirus, Mumps virus, Pneumovirus, Human respiratory syncytial virus, Partitivirus, *Gaeumannomyces graminis* virus 019/6-A, Chrysovirus, *Penicillium chrysogenum* virus, Alphacryptovirus, White clover cryptic viruses 1 and 2, Betacryptovirus, Parvovirinae, Parvovirus, Minute mice virus, Erythrovirus, B19 virus, Dependovirus, Adeno-associated virus 1, Densovirinae, Densovirus, *Junonia coenia* densovirus, Iteravirus, *Bombyx mori* virus, Contravirus, *Aedes aegypti* densovirus, Phycodnavirus, 1-*Paramecium bursaria Chlorella* NC64A virus group, *Paramecium bursaria chlorella* virus 1, 2-*Paramecium bursaria Chlorella* Pbi virus, 3-Hydra *viridis Chlorella* virus, Enterovirus, Poliovirus, Human poliovirus 1, Rhinovirus, Human rhinovirus 1A, Hepatovirus, Human hepatitis A virus, Cardiovirus, Encephalomyocarditis virus, Aphthovirus, Foot-and-mouth disease virus, Plasmavirus, Acholeplasma phage L2, Podovirus, Coliphage T7, Ichnovirus, *Campoletis sonorensis* virus, Bracovirus, *Cotesia melanoscela* virus, Potexvirus, Potato virus X, Potyvirus, Potato virus Y, Rymovirus, *Ryegrass mosaic* virus, Bymovirus, Barley yellow mosaic virus, Orthopoxvirus, Vaccinia virus, Parapoxvirus, Orf virus, Avipoxvirus, Fowlpox virus, Capripoxvirus, Sheep pox virus, Leporipoxvirus, Myxoma virus, Suipoxvirus, Swinepox virus, Molluscipoxvirus, *Molluscum contagiosum* virus, Yatapoxvirus, Yaba monkey tumor virus, Entomopoxviruses A, B, and C, *Melolontha melolontha* entomopoxvirus, *Amsacta moorei* entomopoxvirus, *Chironomus luridus* entomopoxvirus, Orthoreovirus, Mammalian orthoreoviruses, reovirus 3, Avian orthoreoviruses, Orbivirus, African horse sickness viruses 1, Bluetongue viruses 1, Changuinola virus, Corriparta virus, Epizootic hemarrhogic disease virus 1, Equine encephalosis virus, Eubenangee virus group, Lebombo virus, Orungo virus, Palyam virus, Umatilla virus, Wallal virus, Warrego virus, Kemerovo virus, Rotavirus, Groups A-F rotaviruses, Simian rotavirus SA11, Coltivirus, Colorado tick fever virus, Aquareovirus, Groups A-E aquareoviruses, Golden shiner virus, Cypovirus, Cypovirus types 1-12, *Bombyx mori* cypovirus 1, Fijivirus, Fijivirus groups 1-3, Fiji disease virus, Fijivirus groups 2-3, Phytoreovirus, Wound tumor virus, Oryzavirus, Rice ragged stunt, Mammalian type B retroviruses, Mouse mammary tumor virus. Mammalian type C retroviruses, Murine Leukemia Virus, Reptilian type C oncovirus, Viper retrovirus. Reticuloendotheliosis virus, Avian type C retroviruses, Avian leukosis virus, Type D Retroviruses, Mason-Pfizer monkey virus, BLV-HTLV retroviruses, Bovine leukemia virus, Lentivirus, Bovine lentivirus, Bovine immunodeficiency virus. Equine lentivirus, Equine infectious anemia virus, Feline lentivirus, Feline immunodeficiency virus, Canine immunodeficiency virus Ovine/caprine lentivirus, Caprine arthritis encephalitis virus, Visna/maedi virus, Primate lentivirus group, Human immunodeficiency virus 1, Human immunodeficiency virus 2, Human immunodeficiency virus 3. Simian immunodeficiency virus, Spumavirus, Human spuma virus, Vesiculovirus, Vesicular stomatitis virus, Vesicular stomatitis Indiana virus, Lyssavirus, Rabies virus, Ephemerovirus. Bovine ephemeral fever virus, Cytorhabdovirus, Lettuce necrotic yellows virus, Nucleorhabdovirus, Potato yellow dwarf virus, Rhizidiovirus, Rhizidiomyces virus, Sequivirus. Parsnip yellow fleck virus, Waikavirus, Rice tungro spherical virus, Lambda-like phages, Coliphage lambda, Sobemovirus, Southern bean mosaic virus, Tectivirus, Enterobacteria phage PRD1, Tenuivirus, Rice stripe virus, *Nudaurelia capensis* beta-like viruses. *Nudaurelia* beta virus, *Nudaurelia capensis* omega-like viruses, *Nudaurelia* omega virus, Tobamovirus, Tobacco mosaic virus (*vulgare* strain; ssp. NC82 strain), Tobravirus, Tobacco rattle virus, Alphavirus, Sindbis virus, Rubivirus, Rubella virus, Tombusvirus, Tomato bushy stunt, virus, Carmovirus, Carnation mottle virus, Turnip crinkle virus, Totivirus, *Saccharomyces cerevisiae* virus, Giardiavirus, *Giardia lamblia* virus, Leishmaniavirus, *Leishmania brasiliensis* virus 1-1, Trichovirus, Apple chlorotic leaf spot virus, Tymovirus, Turnip yellow mosaic virus, Umbravirus, Carrot mottle virus, Variola virus, Coxsackie virus, Dengue virus, Rous sarcoma virus, Zika virus, Lassa fever virus, Eastern Equine Encephalitis virus, Venezuelan equine encephalitis virus, Western equine encephalitis virus, St. Louis Encephalitis virus, Murray Valley fever virus, West Nile virus, Human T-cell Leukemia virus type-1, echovirus, norovirus, and feline caliciviris (FCV).

In some examples, the virus can comprise an influenza virus, a coronavirus, or a combination thereof. Examples of influenza viruses include, but are not limited to, Influenzavirus A (including the H1N1, H2N2, H3N2, H5N1, H7N7, H1N2, H9N2, H7N2, H7N3, H10N7, H7N9, and H6N1 serotypes), Influenzavirus B, Influenzavirus C, and Influenzavirus D. Examples of coronaviruses include, but are not limited to, avian coronavirus (IBV), porcine epidemic diarrhea virus (PEDV), porcine respiratory coronavirus (PRCV), transmissible gastroenteritis virus (TGEV), feline coronavirus (FCoV), feline infectious peritonitis virus (FIPV), feline enteric coronavirus (FECV), canine coronavirus (CCoV), rabbit coronavirus (RaCoV), mouse hepatitis virus (MHV), rat coronavirus (RCoV), sialodacryadenitis virus of rats (SDAV), bovine coronavirus (BCoV), bovine enterovirus (BEV), porcine coronavirus HKU15 (PorCoV HKU15), Porcine epidemic diarrhea virus (PEDV), porcine hemagglutinating encephalomyelitis virus (HEV), turkey bluecomb coronavirus (TCoV), human coronavirus (HCoV)-229E, HCoV-OC43, HCoV-HKU1, HCoV-NL63, Severe Acute Respiratory Syndrome (SARS)-Coronavirus (CoV)(SARS-CoV), Severe Acute Respiratory Syndrome (SARS)-Coronavirus (CoV)-2 (SARS-CoV-2), and middle east respiratory syndrome (MERS) coronavirus (CoV) (MERS-CoV). In some examples, the virus can comprise Severe Acute Respiratory Syndrome (SARS)-Coronavirus (CoV)-2 (SARS-CoV-2).

Specific examples of bacteria include, but are not limited to, *Mycobacterium tuberculosis, Mycobacterium bovis, Mycobacterium bovis* strain BCG, BCG substrains, *Mycobacterium avium, Mycobacterium intracellular, Mycobacterium africanum, Mycobacterium kansasii, Mycobacterium marinum, Mycobacterium ulcerans, Mycobacterium avium* subspecies paratuberculosis, *Nocardia asteroides*, other *Nocardia* species, *Legionella pneumophila*, other *Legionella* species, *Acetinobacter baumanii. Salmonella typhi, Salmonella enterica, Salmonella Typhimurium*, other *Salmonella* species, *Shigella boydii, Shigella dysenteriae, Shigella sonnei, Shigella flexneri*, other *Shigella* species, *Yersinia pestis, Pasteurella haemolytica, Pasteurella multocida*, other *Pasteurella* species, *Actinobacillus pleuropneumoniae, Listeria monoxytogenes, Listeria ivanovii, Brucella abortus, Brucella suis, Brucella melitensis*, other *Brucella* species, *Cowdria ruminantium, Borrelia burgdorferi, Bordetella avium, Bordetella pertussis, Bordetella bronchiseptica, Bordetella trematum. Bordetella hinzii, Bordetella pteri, Bordetella parapertussis, Bordetella ansorpti*, other *Bordetella* species,

*Burkholderia mallei, Burkholderia psuedomallei, Burkholderia cepacian, Chlamydia pneumoniae, Chlamydia trachomatis, Chlamydia psittaci, Coxiella burneti, Rickettsia rickettsia, Rickettsia prowazekii, rickettsia typhi*, other Rickettsial species, *Ehrlichia* species, *Staphylococcus aureus, Staphylococcus epidermidis, Streptococcus pneumoniae, Streptococcus pyogenes, Streptococcus agalactiae, Streptococcus uberis, Escherichia coli, Vibrio cholerae, Vibrio parahaemolyticus, Campylobacter* species, *Neiserria meningitidis, Neiserria gonorrhea, Pseudomonas aeruginosa*, other *Pseudomonas* species, *Haemophilus influenzae, Haemophilus ducreyi*, other *Hemophilus* species, *Clostridium tetani, Clostridium difficile, Clostridium botulinum, Clostridium perfringens*, other *Clostridium* species, *Yersinia enterolitica, Yersinia pestis*, other *Yersinia* species, *Mycoplasma* species, *Bacillus anthracis, Bacillus abortus*, other *Bacillus* species, *Corynebacterium diptheriae, Corynebacterium bovis, Francisella tularensis, Chlamydophila psittaci, Campylocavter jejuni, Enterobacter aerogenes, Klebsiella pnewnoniae, Klebsiella oxvtoca, Proteus* spp., *Serratia marcescens, Trueperella pyogenes*, and *Vibria vulnificus*.

Specific examples of fungi include, but are not limited to, *Candida albicans, Cryptococcus neoformans, Histoplama capsulatum, Aspergillus niger, Aspergillus oryzae, Aspergillus fumigatus, Coccidioles immitis, Paracoccidioides brasiliensis, Blastoniyces dermitidis, Pneumocystis carinii, Penicillium marneffi, Alternaria alternate, Coccidioides immitits, Fusarium oxysporum, Geotrichum candidum*, and *Histoplasma capsulatum*.

Specific examples of parasites include, but are not limited to, *Toxoplasma gondii, Plasmodium falciparum, Plasmodium vivax, Plasmodium malariae*, other *Plasmodiun* species, *Entamoeba histolytica, Naegleria jowleri, Rhinosporidium seeberi, Giardia lambia, Enterobius vermicularis, Enterobius gregorii, Ascaris lumbricoides, Ancylostoma duodenale, Necator americanus, Cryptosporidiun* spp., *Trypanosoma brucei, Trypanosoma cruzi, Leishmania major*, other *Leishmania* species, *Diphyllobothrium latum, Hymenolepis nana, Hymenolepis diminuta, Echinococcus granulosus, Echinococcus multilocularis, Echinococcus vogeli, Echinococcus oligarthrus, Diphyllobothrium latum, Clonorchis sinensis; Clonorchis viverrini, Fasciola hepatica, Fasciola gigantica, Dicrocoelium dendriticum, Fasciolopsis buski, Metagonimus yokogawai, Opisthorchis viverrini, Opisthorchis felineus, Clonorchis sinensis, Trichomonas vaginalis, Acanthamoeba* species, *Schistosoma intercalatum, Schistosoma haematobium, Schistosoma japonicum, Schistosoma mansoni*, other *Schistosoma* species, *Trichobilharzia regenti, Trchinella spiralis, Trichinella britovi, Trichinella nelsoni, Trichinella nativa*, and *Entamoeba histolytica*.

The plurality of analytes can, for example, have a concentration of 0.01 femtomolar (fM) or more in the aqueous solution (e.g., 0.05 fM or more, 0.1 fM or more, 0.5 fM or more, 1 fM or more, 5 fM or more, 10 fM or more, 50 fM or more, 100 fM or more, 500 fM or more, 1 picomolar (pM) or more, 5 pM or more, 10 pM or more, 50 pM or more, 100 pM or more, 500 pM or more, 1 nanomolar (nM) or more, 5 nM or more, 10 nM or more, 15 nM or more, 20 nM or more, 25 nM or more, 30 nM or more, 35 nM or more, 40 nM or more, 45 nM or more, 50 nM or more, 55 nM or more, 60 nM or more, 65 nM or more, 70 nM or more, 75 nM or more, 80 nM or more, 85 nM or more, 90 nM or more, 95 nM or more, 100 nM or more, 500 nM or more, 1 micromolar (μM) or more, 5 μM or more, 10 μM or more, or 50 μM or more). In some examples, the plurality of analytes can have a concentration of 100 μM or less in the aqueous solution (e.g., 50 μM or less, 10 μM or less, 5 μM or less, 1 μM or less, 500 nM or less, 100 nM or less, 95 nM or less, 90 nM or less, 85 nM or less, 80 nM or less, 75 nM or less, 70 nM or less, 65 nM or less, 60 nM or less, 55 nM or less, 50 nM or less, 45 nM or less, 40 nM or less, 35 nM or less, 30 nM or less, 25 nM or less, 20 nM or less, 15 nM or less, 10 nM or less, 5 nM or less, 1 nM or less, 500 pM or less, 100 pM or less, 50 pM or less, 10 pM or less, 5 pM or less, 1 pM or less, 500 fM or less, 100 fM or less, 50 fM or less, 10 fM or less, 5 fM or less, 1 fM or less, 0.5 fM or less, or 0.1 fM or less). The concentration of the plurality of analytes in the aqueous solution can range from any of the minimum values described above to any of the maximum values described above. For example, the plurality of analytes can have a concentration of from 0.01 fM to 100 pM in the aqueous solution (e.g., from 0.01 fM to 1 pM, from 1 pM to 1 nM, from 1 nM to 100 μM, from 0.01 fM to 1 μM, from 0.01 fM to 100 nM, or from 1 nM to 100 nM).

The biphasic liquid sample comprises one or more droplets comprising a water-immiscible liquid dispersed in the aqueous solution. The water-immiscible liquid can, for example, comprise a biocompatible liquid. In some examples, the water-immiscible liquid comprises a fluorinated solvent, such as a perfluorocarbon, a hydrofluoroether, or a combination thereof. In some examples, the water-immiscible liquid comprises perfluoropentane ($C_5F_{12}$), perfluorohexane ($C_6F_{14}$), or a combination thereof.

The biphasic liquid sample can, for example, have a volume of 1 nanoliter (nL) or more (e.g., 5 nL or more, 10 nL or more, 25 nL or more, 50 nL or more, 75 nL or more, 100 nL or more, 250 nL or more, 500 nL or more, 750 nL or more, 1 microliter (μL) or more, 5 μL or more, 10 μL or more, 25 μL or more, 50 μL or more, 75 μL or more, 100 μL or more, 250 μL or more, 500 μL or more, or 750 μL or more). In some examples, the biphasic liquid sample can have a volume of 1 milliliter (mL) or less (e.g., 750 μL or less, 500 μL or less, 250 μL or less, 100 μL or less, 75 μL or less, 50 μL or less, 25 μL or less, 10 μL or less, 5 μL or less, 1 μL or less, 750 nL or less, 500 nL or less, 250 nL or less, 100 nL or less, 75 nL or less, 50 nL or less, 25 nL or less, 10 nL or less, or 5 nL or less). The volume of the biphasic liquid sample can range from any of the minimum values described above to any of the maximum values described above. For examples, the biphasic liquid sample can have a volume of from 1 nL to 1 mL (e.g., from 1 nL to 1 μL, from 1 μL to 1 mL, from 1 nL to 500 nL, from 500 nL to 1 μL, from 1 μL to 500 μL, from 500 μL to 1 mL, from 1 nL to 750 μL, from 50 nL to 1 mL, or from 50 nL to 750 μL).

In some examples, the methods further comprise depositing the biphasic liquid sample on the optothermal substrate. Depositing the biphasic liquid sample can, for example, comprise spin-coating, drop casting, dip coating, or a combination thereof.

In some examples, the methods further comprise forming the biphasic liquid sample by dispersing the one or more droplets comprising the water-immiscible liquid in the aqueous solution. Dispersing the one or more droplets comprising the water-immiscible liquid in the aqueous solution can be accomplished by mechanical agitation, for example, mechanical stirring, shaking, vortexing, sonication (e.g., bath sonication, probe sonication, ultrasonication), and the like, or combinations thereof. For example, forming the biphasic liquid sample can comprise combining the water-immiscible liquid and the aqueous solution to form a mixture, and agitating (e.g., stirring, shaking, vortexing, sonicating, etc.) the mixture to disperse the one or more droplets comprising the water-immiscible liquid in the aqueous solution. In some examples, the methods can further comprise collecting the aqueous solution (e.g., wherein the aqueous solution comprises a bodily fluid). In some examples, the methods can further comprise purifying the aqueous solution before forming the biphasic liquid sample. Purifying the aqueous solution can, for example, comprise filtering, centrifuging, electrophoresis, or a combination thereof.

At least one of the droplets comprising the water-immiscible liquid is disposed on the optothermal substrate proximate the first location, the at least one droplet comprising the water-immiscible liquid disposed on the optothermal substrate being a surface droplet. The surface droplet can, for example, have an average droplet size (e.g., average diameter of the droplet on the substrate) of 100 nanometers (nm) or more (e.g., 150 nm or more, 200 nm or more, 250 nm or more, 300 nm or more, 350 nm or more, 400 nm or more, 450 nm or more, 500 nm or more, 600 nm or more, 700 nm or more, 800 nm or more, 900 nm or more, 1 micrometer (μm, micron) or more, 1.5 μm or more, 2 μm or more, 2.5 μm or more, 3 μm or more, 3.5 μm or more, 4 μm or more, 4.5 μm or more, 5 μm or more, 6 μm or more, 7 μm or more, 8 μm or more, 9 μm or more, 10 μm or more, 15 μm or more, 20 μm or more, 25 μm or more, 30 μm or more, 35 μm or more, 40 μm or more, 45 μm or more, 50 μm or more, 60 μm or more, 70 μm or more, 80 μm or more, or 90 μm or more). In some examples the surface droplet can have an average droplet size of 100 μm or less (e.g., 90 μm or less, 80 μm or less, 70 μm or less, 60 μm or less, 50 μm or less, 45 μm or less, 40 μm or less, 35 μm or less, 30 μm or less, 25 μm or less, 20 μm or less, 15 μm or less, 10 μm or less, 9 μm or less, 8 μm or less, 7 μm or less, 6 μm or less, 5 μm or less, 4.5 μm or less, 4 μm or less, 3.5 μm or less, 3 μm or less, 2.5 μm or less, 2 μm or less, 1.5 μm or less, 1 μm or less, 900 nm or less, 800 nm or less, 700 nm or less, 600 nm or less, 500 nm or less, 450 nm or less, 400 nm or less, 350 nm or less, 300 nm or less, 250 nm or less, or 200 nm or less). The average droplet size of the surface droplet can range from any of the minimum values described above to any of the maximum values described above. For example, the surface droplet can have an average droplet size of from 100 nm to 100 μm (e.g., from 100 nm to 1 μm, from 1 μm to 100 μm, from 100 nm to 500 nm, from 500 nm to 1 μm, from 1 μm to 50 μm, from 50 μm to 100 μm, from 100 nm to 50 μm, from 500 nm to 100 μm, from 500 nm to 50 μm, or from 500 nm to 10 μm). In some examples, the surface droplet has an average droplet size of from 2 micrometers (μm) to 3 μm.

The methods described herein comprise illuminating the first location of the optothermal substrate with electromagnetic radiation; wherein the optothermal substrate converts at least a portion of the electromagnetic radiation into thermal energy; wherein the optothermal substrate is in thermal contact with the biphasic liquid sample comprising an aqueous solution and one or more droplets comprising a water-immiscible liquid dispersed in the aqueous solution, and wherein the aqueous solution comprises water and a plurality of analytes; wherein the aqueous solution has a boiling point and the water-immiscible liquid has a boiling point, and the boiling point of the water-immiscible liquid is less than the boiling point of the aqueous solution; wherein before illumination, the biphasic liquid sample has a first temperature (e.g., an initial or in-situ temperature) and the first temperature is less than the boiling point of the water-immiscible liquid; wherein at least one of the droplets comprising the water-immiscible liquid is disposed on the optothermal substrate proximate the first location, the at least one droplet comprising the water-immiscible liquid disposed on the optothermal substrate being a surface droplet; and wherein the thermal energy provided by the optothermal substrate increases the temperature of the biphasic liquid sample proximate the first location to a second temperature, wherein the second temperature is greater than or equal to the boiling point of the water-immiscible liquid and less than the boiling point of the aqueous solution.

The first temperature can, for example, be 273 Kelvin (K) or more (e.g., 275 K or more, 280 K or more, 285 K or more, 286 K or more, 287 K or more, 288 K or more, 289 K or more, 290 K or more, 291 K or more, 292 K or more, 293 K or more, 294 K or more, 295 K or more, 296 K or more, 297 K or more, 298 K or more, 299 K or more, 300 K or more, 305 K or more, 310 K or more, 315 K or more, 320 K or more, 325 K or more, 330 K or more, 335 K or more, 340 K or more, 345 K or more, 350 K or more, 355 K or more, 360 K or more, or 365 K or more). In some examples, the first temperature can be 372 K or less (e.g., 370 K or less, 365 K or less, 360 K or less, 355 K or less, 350 K or less, 345 K or less, 340 K or less, 335 K or less, 330 K or less, 325 K or less, 320 K or less, 315 K or less, 310 K or less, 305 K or less, 300 K or less, 299 K or less, 298 K or less, 297 K or less, 296 K or less, 295 K or less, 294 K or less, 293 K or less, 292 K or less, 291 K or less, 290 K or less, 289 K or less, 288 K or less, 287 K or less, 286 K or less, 285 K or less, 280 K or less, or 275 K or less). The first temperature can range from any of the minimum values described above to any of the maximum values described above. For example, the first temperature can be from 273 K to 372 K (e.g., from 273 K to 320 K, from 320 K to 372 K, from 273 K to 290 K, from 290 K to 305 K, from 305 K to 320 K, from 320 K to 335 K, from 335 K to 350 K, from 350 K to 372 K, from 280 K to 372 K, from 273 K to 350 K, from 280 K to 350 K. or from 280 K to 320 K).

The second temperature can, for example, be 276 Kelvin (K) or more (e.g., 280 K or more, 285 K or more, 286 K or more, 287 K or more, 288 K or more, 289 K or more, 290 K or more, 291 K or more, 292 K or more, 293 K or more, 294 K or more, 295 K or more, 296 K or more, 297 K or more, 298 K or more, 299 K or more, 300 K or more, 305 K or more, 310 K or more, 315 K or more, 320 K or more, 325 K or more, 330 K or more, 335 K or more, 340 K or more, 345 K or more, 350 K or more, 355 K or more, 360 K or more, or 365 K or more). In some examples, the second temperature can be 372 K or less (e.g., 370 K or less, 365 K or less, 360 K or less, 355 K or less, 350 K or less, 345 K or less, 340 K or less, 335 K or less, 330 K or less, 325 K or less, 320 K or less, 315 K or less, 310 K or less, 305 K or less, 300 K or less, 299 K or less, 298 K or less, 297 K or less, 296 K or less, 295 K or less, 294 K or less, 293 K or less, 292 K or less, 291 K or less, 290 K or less, 289 K or less, 288 K or less, 287 K or less, 286 K or less, 285 K or less, or 280 K or less). The second temperature can range from any of the minimum values described above to any of the maximum values described above. For example, the second temperature can be from 276 K to 372 K (e.g., from 276 K to 320 K, from 320 K to 372 K, from 276 K to 290 K, from 290 K to 305 K, from 305 K to 320 K, from 320 K to 335 K, from 335 K to 350 K, from 350 K to 372 K, from 280 K to 372 K, from 276 K to 350 K, from 280 K to 350 K, from 280 K to 320 K, or from 300 K to 320 K).

The second temperature can, for example, be greater than the first temperature by 3 K or more (e.g., 5 K or more, 10 K or more, 15 K or more, 20 K or more, 25 K or more, 30 K or more, 35 K or more, 40 K or more, 45 K or more, 50 K or more, 55 K or more, 60 K or more, 65 K or more, 70 K or more, 75 K or more, 80 K or more, 85 K or more, or 90 K or more). In some examples, the second temperature can be greater than the first temperature by 100 K or less (e.g., 95 K or less, 90 K or less, 85 K or less, 80 K or less, 75 K or less, 70 K or less, 65 K or less, 60 K or less, 55 K or less, 50 K or less, 45 K or less, 40 K or less, 35 K or less, 30 K or less, 25 K or less, 20 K or less, 15 K or less, or 10 K or less). The difference between the first temperature and the second temperature can range from any of the minimum values described above to any of the maximum values described above. For example, the second temperature can be greater than the first temperature by from 3 K to 100 K (e.g., from 3 K to 50 K, from 50 K to 100 K, from 3 K to 20 K, from 20 K to 40 K, form 40 K to 60 K, from 60 K to 80 K, from 80 K to 100 K, or from 5 K to 90 K).

The methods described herein further comprise generating a bubble at a location in the biphasic liquid sample proximate to the first location of the optothermal substrate via vaporization of the surface droplet via optothermal effects, the bubble having a gas-liquid interface with the aqueous solution and a gas-solid interface with the optothermal substrate. In some examples, the optothermal substrate comprises a plasmonic substrate and the electromagnetic radiation comprises a wavelength that overlaps with at least a portion of the plasmon resonance energy of the plasmonic substrate, and the bubble can be generated by plasmon-enhanced photothermal effects.

The bubble can, for example, have a diameter of 100 nm or more (e.g., 125 nm or more, 150 nm or more, 175 nm or more, 200 nm or more, 225 nm or more, 250 nm or more, 300 nm or more, 350 nm or more, 400 nm or more, 450 nm or more, 500 nm or more, 600 nm or more, 700 nm or more, 800 nm or more, 900 nm or more, 1 µm or more, 1.5 µm or more, 2 µm or more, 2.5 µm or more, 3 µm or more, 3.5 µm or more, 4 µm or more, 4.5 µm or more, 5 µm or more, 6 µm or more, 7 µm or more, 8 µm or more, 9 µm or more, 10 µm or more, 15 µm or more, 20 µm or more, 25 µm or more, 30 µm or more, 35 µm or more, 40 µm or more, 45 µm or more, 50 µm or more, 60 µm or more, 70 µm or more, 80 µm or more, 90 µm or more, 100 µm or more, 125 µm or more, 150 µm or more, 175 µm or more, 200 µm or more, 225 µm or more, 250 µm or more, 300 µm or more, 350 µm or more, or 400 µm or more). In some examples, the bubble can have a diameter of 500 µm or less (e.g., 450 µm or less, 400 µm or less, 350 µm or less, 300 µm or less, 250 µm or less, 225 µm or less, 200 µm or less, 175 µm or less, 150 µm or less, 125 µm or less, 100 µm or less, 90 µm or less, 80 µm or less, 70 µm or less, 60 µm or less, 50 µm or less, 45 µm or less, 40 µm or less, 35 µm or less, 30 µm or less, 25 µm or less, 20 µm or less, 15 µm or less, 10 µm or less, 9 µm or less, 8 µm or less, 7 µm or less, 6 µm or less, 5 µm or less, 4.5 µm or less, 4 µm or less, 3.5 µm or less, 3 µm or less, 2.5 µm or less, 2 µm or less, 1.5 µm or less, 1 µm or less, 900 nm or less, 800 nm or less, 700 nm or less, 600 nm or less, 500 nm or less, 450 nm or less, 400 nm or less, 350 nm or less, 300 nm or less, 250 nm or less, 225 nm or less, 200 nm or less, 175 nm or less, or 150 nm or less). The diameter of the bubble can range from any of the minimum values described above to any of the maximum values described above. For example, the bubble can have a diameter of from 100 nm to 500 µm (e.g., from 100 nm to 1 µm, from 1 µm to 500 µm, from 100 nm to 500 nm, from 500 nm to 1 µm, from 1 µm to 250 µm, from 250 µm to 500 µm, from 100 nm to 400 µm, from 200 nm to 500 µm, from 200 nm to 400 µm, from 500 nm to 300 µm, or from 1 µm to 100 µm).

The methods further comprise trapping at least a portion of the plurality of analytes at the gas-liquid interface of the bubble and the aqueous solution, said portion of the plurality of analytes trapped at the gas-liquid interface being a trapped portion of the plurality of analytes. In some examples, the trapped portion of the plurality of analytes are not damaged during the trapping. In some examples, the trapped portion of the plurality of analytes are trapped by convection, surface tension, gas pressure, substrate adhesion, an electrostatic force, a thermophoretic force, van der Waals force, or combinations thereof. In some examples, the trapped portion of the plurality of analytes are trapped by convection (e.g., natural convection and/or Marangoni convection).

The methods further comprise depositing at least a portion of the trapped portion of the plurality of analytes on the optothermal substrate proximate to the gas-solid interface of the bubble and the optothermal substrate, said portion of the trapped portion of the plurality of analytes deposited on the optothermal substrate being a deposited portion of the plurality of analytes. In some examples, the deposited portion of the plurality of analytes are not damaged during the deposition. The bubble can, for example, be used to overcome the diffusion limit and concentrate at least a portion of the plurality of analytes at or near the optothermal substrate.

The deposited portion of the plurality of analytes can, for example, be deposited in an amount of time of 1 millisecond (ms) or more (e.g., 2 milliseconds or more, 3 milliseconds or more, 4 milliseconds or more, 5 milliseconds or more, 10 milliseconds or more, 15 milliseconds or more, 20 milliseconds or more, 25 milliseconds or more, 30 milliseconds or more, 35 milliseconds or more, 40 milliseconds or more, 45 milliseconds or more, 50 milliseconds or more, 60 milliseconds or more, 70 milliseconds or more, 80 milliseconds or more, 90 milliseconds or more, 100 milliseconds or more, 125 milliseconds or more, 150 milliseconds or more, 175 milliseconds or more, 200 milliseconds or more, 225 milliseconds or more, 250 milliseconds or more, 300 milliseconds or more, 350 milliseconds or more, 400 milliseconds or more, 450 milliseconds or more, 500 milliseconds or more, 600 milliseconds or more, 700 milliseconds or more, 800 milliseconds or more, 900 milliseconds or more, 1 second or more, 2 seconds or more, 3 seconds or more, 4 seconds or more, 5 seconds or more, 10 seconds or more, 15 seconds or more, 20 seconds or more, 25 seconds or more, 30 seconds or more, 35 seconds or more, 40 seconds or more, 45 seconds or more, 50 seconds or more, 55 seconds or more, 1 minute or more, 2 minutes or more, 3 minutes or more, 4 minutes or more, 5 minutes or more, 6 minutes or more, 7 minutes or more, 8 minutes or more, 9 minutes or more, 10 minutes or more, 15 minutes or more, 20 minutes or more, 25 minutes or more, 30 minutes or more, 35 minutes or more, 40 minutes or more, 45 minutes or more, 50 minutes or more, 55 minutes or more, 1 hour or more, 2 hours or more, 3 hours or more, 4 hours or more, or 5 hours or more).

In some examples, the deposited portion of the plurality of analytes can be deposited in an amount of time of 6 hours or less (e.g., 5 hours or less, 4 hours or less, 3 hours or less, 2 hours or less, 1 hour or less, 55 minutes or less, 50 minutes or less, 45 minutes or less, 40 minutes or less, 35 minutes or less, 30 minutes or less, 25 minutes or less, 20 minutes or less, 15 minutes or less, 10 minutes or less, 9 minutes or less, 8 minutes or less, 7 minutes or less, 6 minutes or less, 5 minutes or less, 4 minutes or less, 3 minutes or less, 2 minutes or less, 1 minutes or less, 55 seconds or less, 50 seconds or less, 45 seconds or less, 40 seconds or less, 35 seconds or less, 30 seconds or less, 25 seconds or less, 20 seconds or less, 15 seconds or less, 10 seconds or less, 5 seconds or less, 4 seconds or less, 3 seconds or less, 2 seconds or less, 1 second or less, 900 milliseconds or less, 800 milliseconds or less, 700 milliseconds or less, 600 milliseconds or less, 500 milliseconds or less, 450 milliseconds or less, 400 milliseconds or less, 350 milliseconds or less, 300 milliseconds or less, 250 milliseconds or less, 225 milliseconds or less, 200 milliseconds or less, 175 milliseconds or less, 150 milliseconds or less, 125 milliseconds or less, 100 milliseconds or less, 90 milliseconds or less, 80 milliseconds or less, 70 milliseconds or less, 60 milliseconds or less, 50 milliseconds or less, 45 milliseconds or less, 40 milliseconds or less, 35 milliseconds or less, 30 milliseconds or less, 25 milliseconds or less, 20 milliseconds or less, 15 milliseconds or less, 10 milliseconds or less, or 5 milliseconds or less).

The amount of time in which the deposited portion of the plurality of analytes is deposited can range from any of the minimum values described above to any of the maximum values described above. For example, the deposited portion of the plurality of analytes can be deposited in an amount of time from 1 millisecond to 6 hours (e.g., from 1 millisecond to 1 second, from 1 second to 1 minute, from 1 minute to 6 hours, from 1 millisecond to 1 hour, from 500 milliseconds to 6 hours, from 500 milliseconds to 1 hour, or from 1 millisecond (ms) to 10 minutes). For example, the deposited portion of the plurality of analytes can be deposited in an amount of time of 1 minute or less.

In some examples, the deposited portion of the plurality of analytes are immobilized on the optothermal substrate by surface adhesion. In some examples, the optothermal substrate further comprises a ligand and the deposited portion of the plurality of analytes are immobilized on the optothermal substrate by electrostatic attraction and/or chemical recognition with the ligand. In some examples, the ligand is not damaged during the method.

In some examples, the methods can further comprise capturing an electromagnetic signal from at least a portion of the deposited portion of the plurality of analytes, at least a portion of the optothermal substrate proximate the first location, or a combination thereof. In some examples, the methods can further comprise processing the electromagnetic signal to determine a property of the biphasic liquid sample. The property of the biphasic liquid sample can, for example, comprise the presence of the surface droplet, the presence of the bubble, the presence of the deposited portion of the plurality of analytes, or a combination thereof.

In some examples, the plurality of analytes comprise a pathogen, a biomarker, or a combination thereof, the property of the biphasic liquid sample comprises the presence of the deposited portion of the plurality of analytes, and the method further comprises diagnosing and/or monitoring a disease in a subject based thereon. Examples of diseases include, but are not limited to, neurodegenerative diseases, infectious diseases, rheumatologic diseases, genetic diseases, acute and chronic respiratory diseases, gastrointestinal and liver diseases, dermatologic diseases, and combinations thereof. In some examples, the disease can comprise a respiratory infection. In some examples, the disease can comprise a viral infection, such as with an influenza virus, a coronavirus, or a combination thereof. In some examples, the disease can comprise an infection with SARS coronavirus, SARS coronavirus 2, or a combination thereof. In some examples, the methods can further comprise selecting a course of therapy for the subject based on the property of the biphasic liquid sample.

The time elapsed from illuminating the first location of the optothermal substrate to determining the property of the biphasic liquid sample can, for example, be 1 millisecond (ms) or more (e.g., 2 milliseconds or more, 3 milliseconds or more, 4 milliseconds or more, 5 milliseconds or more, 10 milliseconds or more, 15 milliseconds or more, 20 milliseconds or more, 25 milliseconds or more, 30 milliseconds or more, 35 milliseconds or more, 40 milliseconds or more, 45 milliseconds or more, 50 milliseconds or more, 60 milliseconds or more, 70 milliseconds or more, 80 milliseconds or more, 90 milliseconds or more, 100 milliseconds or more, 125 milliseconds or more, 150 milliseconds or more, 175 milliseconds or more, 200 milliseconds or more, 225 milliseconds or more, 250 milliseconds or more, 300 milliseconds or more, 350 milliseconds or more, 400 milliseconds or more, 450 milliseconds or more, 500 milliseconds or more, 600 milliseconds or more, 700 milliseconds or more, 800 milliseconds or more, 900 milliseconds or more, 1 second or more, 2 seconds or more, 3 seconds or more, 4 seconds or more, 5 seconds or more, 10 seconds or more, 15 seconds or more, 20 seconds or more, 25 seconds or more, 30 seconds or more, 35 seconds or more, 40 seconds or more, 45 seconds or more, 50 seconds or more, 55 seconds or more, 1 minute or more, 2 minutes or more, 3 minutes or more, 4 minutes or more, 5 minutes or more, 6 minutes or more, 7 minutes or more, 8 minutes or more, 9 minutes or more, 10 minutes or more, 15 minutes or more, 20 minutes or more, 25 minutes or more, 30 minutes or more, 35 minutes or more, 40 minutes or more, 45 minutes or more, 50 minutes or more, 55 minutes or more, 1 hour or more, 2 hours or more, 3 hours or more, 4 hours or more, or 5 hours or more).

In some examples, the time elapsed from illuminating the first location of the optothermal substrate to determining the property of the biphasic liquid sample can be 6 hours or less (e.g., 5 hours or less, 4 hours or less, 3 hours or less, 2 hours or less, 1 hour or less, 55 minutes or less, 50 minutes or less, 45 minutes or less, 40 minutes or less, 35 minutes or less, 30 minutes or less, 25 minutes or less, 20 minutes or less, 15 minutes or less, 10 minutes or less, 9 minutes or less, 8 minutes or less, 7 minutes or less, 6 minutes or less, 5 minutes or less, 4 minutes or less, 3 minutes or less, 2 minutes or less, 1 minutes or less, 55 seconds or less, 50 seconds or less, 45 seconds or less, 40 seconds or less, 35 seconds or less, 30 seconds or less, 25 seconds or less, 20 seconds or less, 15 seconds or less, 10 seconds or less, 5 seconds or less, 4 seconds or less, 3 seconds or less, 2 seconds or less, 1 second or less, 900 milliseconds or less, 800 milliseconds or less, 700 milliseconds or less, 600 milliseconds or less, 500 milliseconds or less, 450 milliseconds or less, 400 milliseconds or less, 350 milliseconds or less, 300 milliseconds or less, 250 milliseconds or less, 225 milliseconds or less, 200 milliseconds or less, 175 milliseconds or less, 150 milliseconds or less, 125 milliseconds or less, 100 milliseconds or less, 90 milliseconds or less, 80 milliseconds or less, 70 milliseconds or less, 60 milliseconds or less, 50 milliseconds or less, 45 milliseconds or less, 40 milliseconds or less, 35 milliseconds or less, 30 milliseconds or less, 25 milliseconds or less, 20 milliseconds or less, 15 milliseconds or less, 10 milliseconds or less, or 5 milliseconds or less).

The amount of time elapsed from illuminating the first location of the optothermal substrate to determining the property of the biphasic liquid sample can range from any of the minimum values described above to any of the maximum values described above. For example, the time elapsed from illuminating the first location of the optothermal substrate to determining the property of the biphasic liquid sample can be from 1 millisecond to 6 hours (e.g., from 1 millisecond to 1 second, from 1 second to 1 minute, from 1 minute to 6 hours, from 1 millisecond to 1 hour, from 500 milliseconds to 6 hours, from 500 milliseconds to 1 hour, from 1 millisecond to 30 minutes, or from 1 millisecond to 10 minutes). In some examples, the time elapsed from illuminating the first location of the optothermal substrate to determining the property of the biphasic liquid sample can be 10 minutes or less, 5 minutes or less, or 1 minute or less.

In some examples, the methods can further comprise illuminating a second location of the optothermal substrate with the electromagnetic radiation; wherein a second droplet comprising the water-immiscible liquid is disposed on the optothermal substrate proximate the second location, the second droplet comprising the water-immiscible liquid disposed on the optothermal substrate being a second surface droplet; wherein the optothermal substrate converts at least a portion of the electromagnetic radiation into thermal energy, and the thermal energy increases the temperature of the biphasic liquid sample proximate the second location to a third temperature, wherein the third temperature is greater than or equal to the boiling point of the water-immiscible liquid; thereby: generating a second bubble at a location in the biphasic liquid sample proximate to the second location of the optothermal substrate via vaporization of the second surface droplet via optothermal effects, the second bubble having a gas-liquid interface with the aqueous solution and a gas-solid interface with the optothermal substrate; trapping at least a second portion of the plurality of analytes at the gas-liquid interface of the second bubble and the aqueous solution, said portion of the plurality of analytes trapped at the gas-liquid interface of the second bubble and the aqueous solution being a second trapped portion of the plurality of analytes; and depositing at least a portion of the second trapped portion of the plurality of analytes on the optothermal substrate proximate to the gas-solid interface of the second bubble and the optothermal substrate, said portion of the second trapped portion of the plurality of analytes deposited on the optothermal substrate being a second deposited portion of the plurality of analytes. As used herein, "a second location" and "the second location" are meant to include any number of locations in any arrangement on the plasmonic substrate. Thus, for example "a second location" includes one or more second locations. In some embodiments, the second location can comprise a plurality of locations.

In some examples, the optothermal substrate is translocated to illuminate the second location. As used herein translocating refers to any type of movement about any axis (e.g., rotation, translation, etc.) In other words, as used herein, translocation refers to a change in position and/or orientation. In some examples, the electromagnetic radiation is provided by a light source, and the light source is translocated to illuminate the second location. In some examples, the electromagnetic radiation is provided by a light source, the light source being configured to illuminate a mirror and the mirror is configured to reflect the electromagnetic radiation from the artificial light source to illuminate the optothermal substrate, and the mirror is translocated to illuminate the second location.

The second surface droplet can, for example, have an average droplet size of from 100 nm to 100 μm. In some examples, the second surface droplet has an average droplet size of from 1 μm to 100 μm. In some examples, the second surface droplet has an average droplet size of from 2 micrometers (μm) to 3 μm.

The second bubble can, for example, have a diameter of from 100 nm to 500 μm.

The third temperature can, for example, be 276 Kelvin (K) or more (e.g., 280 K or more, 285 K or more, 286 K or more, 287 K or more, 288 K or more, 289 K or more, 290 K or more, 291 K or more, 292 K or more, 293 K or more, 294 K or more, 295 K or more, 296 K or more, 297 K or more, 298 K or more, 299 K or more, 300 K or more, 305 K or more, 310 K or more, 315 K or more, 320 K or more, 325 K or more, 330 K or more, 335 K or more, 340 K or more, 345 K or more, 350 K or more, 355 K or more, 360 K or more, or 365 K or more). In some examples, the third temperature can be 372 K or less (e.g., 370 K or less, 365 K or less, 360 K or less, 355 K or less, 350 K or less, 345 K or less, 340 K or less, 335 K or less, 330 K or less, 325 K or less, 320 K or less, 315 K or less, 310 K or less, 305 K or less, 300 K or less, 299 K or less, 298 K or less, 297 K or less, 296 K or less, 295 K or less, 294 K or less, 293 K or less, 292 K or less, 291 K or less, 290 K or less, 289 K or less, 288 K or less, 287 K or less, 286 K or less, 285 K or less, or 280 K or less). The third temperature can range from any of the minimum values described above to any of the maximum values described above. For example, the third temperature can be from 276 K to 372 K (e.g., from 276 K to 320 K, from 320 K to 372 K, from 276 K to 290 K, from 290 K to 305 K, from 305 K to 320 K, from 320 K to 335 K, from 335 K to 350 K, from 350 K to 372 K, from 280 K to 372 K, from 276 K to 350 K, from 280 K to 350 K, from 280 K to 320 K, or from 300 K to 320 K).

The third temperature can, for example, be greater than the first temperature by 3 K or more (e.g., 5 K or more, 10 K or more, 15 K or more, 20 K or more, 25 K or more, 30 K or more, 35 K or more, 40 K or more, 45 K or more, 50 K or more, 55 K or more, 60 K or more, 65 K or more, 70 K or more, 75 K or more, 80 K or more, 85 K or more, or 90 K or more). In some examples, the third temperature can be greater than the first temperature by 100 K or less (e.g., 95 K or less, 90 K or less, 85 K or less, 80 K or less, 75 K or less, 70 K or less, 65 K or less, 60 K or less, 55 K or less, 50 K or less, 45 K or less, 40 K or less, 35 K or less, 30 K or less, 25 K or less, 20 K or less, 15 K or less, or 10 K or less). The difference between the first temperature and the third temperature can range from any of the minimum values described above to any of the maximum values described above. For example, the third temperature can be greater than the first temperature by from 3 K to 100 K (e.g., from 3 K to 50 K, from 50 K to 100 K, from 3 K to 20 K, from 20 K to 40 K, form 40 K to 60 K, from 60 K to 80 K, from 80 K to 100 K, or from 5 K to 90 K).

In some examples, the methods can further comprise capturing a second electromagnetic signal from at least a portion of the second deposited portion of the plurality of analytes, at least a portion of the optothermal substrate proximate the second location, or a combination thereof.

In some examples, the methods can further comprise processing the second electromagnetic signal to determine a second property of the biphasic liquid sample. The second property of the biphasic liquid sample can, for example, comprise the presence of the second surface droplet, the presence of the second bubble, the presence of the second deposited portion of the plurality of analytes, or a combination thereof.

In some examples, the methods can further comprise washing the optothermal substrate (e.g., with a solvent) to substantially remove the deposited portion of the plurality of analytes and, if present, the second deposited portion of the plurality of analytes. In some examples, the methods can further comprise using the washed optothermal substrate in any of the methods described herein.

Devices

Also disclosed herein are devices comprise any of the optothermal substrates and biphasic liquid samples described herein.

Referring now to FIG. 1, for example, also disclosed herein are devices 100 comprising an optothermal substrate 102 in thermal contact with a biphasic liquid sample 104 comprising an aqueous solution 106 and one or more droplets comprising a water-immiscible liquid 108 dispersed in the aqueous solution, wherein the aqueous solution comprises water and a plurality of analytes. The water-immiscible liquid has a boiling point and when the device, for example, is assembled together with a light source: the biphasic liquid sample is in thermal contact with the optothermal substrate; the light source is configured to illuminate a first location of the optothermal substrate with electromagnetic radiation: wherein the optothermal substrate converts at least a portion of the electromagnetic radiation into thermal energy; wherein before illumination, the biphasic liquid sample has a first temperature and the first temperature is less than the boiling point of the water-immiscible liquid; wherein at least one of the droplets comprising the water-immiscible liquid is disposed on the optothermal substrate proximate the first location, the at least one droplet comprising the water-immiscible liquid disposed on the optothermal substrate being a surface droplet; wherein the thermal energy provided by the optothermal substrate increases the temperature of the biphasic liquid sample proximate the first location to a second temperature, wherein the second temperature is greater than or equal to the boiling point of the water-immiscible liquid; thereby: generating a bubble at a location in the biphasic liquid sample proximate to the first location of the optothermal substrate via vaporization of the surface droplet via optothermal effects, the bubble having a gas-liquid interface with the aqueous solution and a gas-solid interface with the optothermal substrate; trapping at least a portion of the plurality of analytes at the gas-liquid interface of the bubble and the aqueous solution, said portion of the plurality of analytes trapped at the gas-liquid interface being a trapped portion of the plurality of analytes; and depositing at least a portion of the trapped portion of the plurality of analytes on the optothermal substrate proximate to the gas-solid interface of the bubble and the optothermal substrate, said portion of the trapped portion of the plurality of analytes deposited on the optothermal substrate being a deposited portion of the plurality of analytes.

Systems

Also disclosed herein are systems for performing the methods described herein. For example, the systems can comprise any of the devices described herein and a light source.

Figure 2:
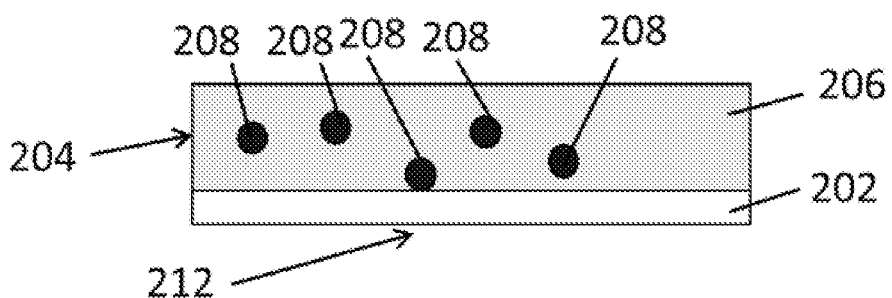
FIG. 2 is a schematic illustration of an example system as disclosed herein for analyte sensing with optothermally generated bubbles in biphasic liquid samples.
Figure 2:
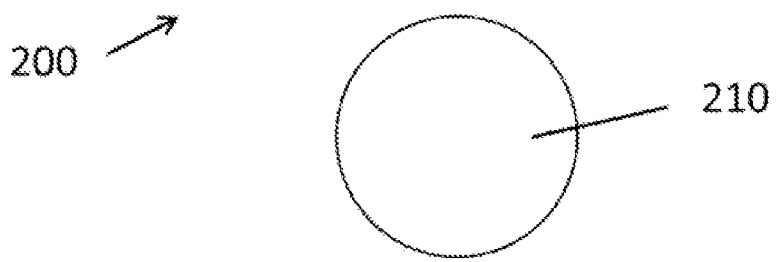

Referring now to FIG. 2, the systems 200 can comprise an optothermal substrate 202 in thermal contact with a biphasic liquid sample 204 comprising an aqueous solution 206 and one or more droplets comprising a water-immiscible liquid 208 dispersed in the aqueous solution 206, wherein the aqueous solution 206 comprises water and a plurality of analytes, and a light source 210 configured to illuminate a first location 212 of the optothermal substrate 202 with electromagnetic radiation. In some examples, the systems 200 can include a single light source 210. In other examples, more than one light source 210 can be included in the systems 200. The light source(s) 210 can, for example comprise(s) an artificial light source, such as a laser.

In some examples, the systems 200 can further comprise a means for translocating the optothermal substrate 202 and/or the light source 210.

The optothermal substrate 202 converts at least a portion of the electromagnetic radiation into thermal energy; wherein the aqueous solution 206 has a boiling point and the water-immiscible liquid 208 has a boiling point, and the boiling point of the water-immiscible liquid 208 is less than the boiling point of the aqueous solution 206; wherein before illumination, the biphasic liquid sample 204 has a first temperature and the first temperature is less than the boiling point of the water-immiscible liquid 208; wherein at least one of the droplets comprising the water-immiscible liquid 208 is disposed on the optothermal substrate 202 proximate the first location 212, the at least one droplet comprising the water-immiscible liquid 208 disposed on the optothermal substrate 202 being a surface droplet; wherein the thermal energy provided by the optothermal substrate 202 increases the temperature of the biphasic liquid sample 204 proximate the first location 212 to a second temperature, wherein the second temperature is greater than or equal to the boiling point of the water-immiscible liquid 208; thereby: generating a bubble at a location in the biphasic liquid sample 204 proximate to the first location 212 of the optothermal substrate 202 via vaporization of the surface droplet via optothermal effects, the bubble having a gas-liquid interface with the aqueous solution 206 and a gas-solid interface with the optothermal substrate 202; trapping at least a portion of the plurality of analytes at the gas-liquid interface of the bubble and the aqueous solution 206, said portion of the plurality of analytes trapped at the gas-liquid interface being a trapped portion of the plurality of analytes; and depositing at least a portion of the trapped portion of the plurality of analytes on the optothermal substrate 202 proximate to the gas-solid interface of the bubble and the optothermal substrate 202, said portion of the trapped portion of the plurality of analytes deposited on the optothermal substrate being a deposited portion of the plurality of analytes.

Figure 3:
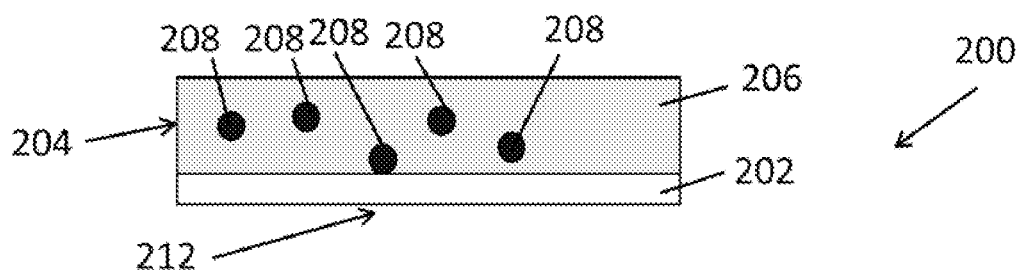
FIG. 3 is a schematic illustration of an example system as disclosed herein for analyte sensing with optothermally generated bubbles in biphasic liquid samples.

Referring now to FIG. 3, the systems 200 can, in some examples, further comprise a mirror 214, wherein the light source 210 is configured to illuminate the mirror 214 and the mirror 214 is configured to reflect the electromagnetic radiation from the light source 210 to illuminate the first location 212 of the optothermal substrate 202. In some examples, the mirror can comprise a plurality of mirrors (e.g., a digital micromirror device). In some examples, the systems 200 can further comprise a means for translocating the mirror 214.

In some examples, the systems 200 can further comprise a lens (e.g., one or more lenses). The lens can be any type of lens, such as a simple lens, a compound lens, a spherical lens, a toric lens, a biconvex lens, a plano-convex lens, a plano-concave lens, a negative meniscus lens, a positive meniscus lens, a biconcave lens, a converging lens, a diverging lens, a cylindrical lens, a Fresnel lens, a lenticular lens, or a gradient index lens.

Figure 4:
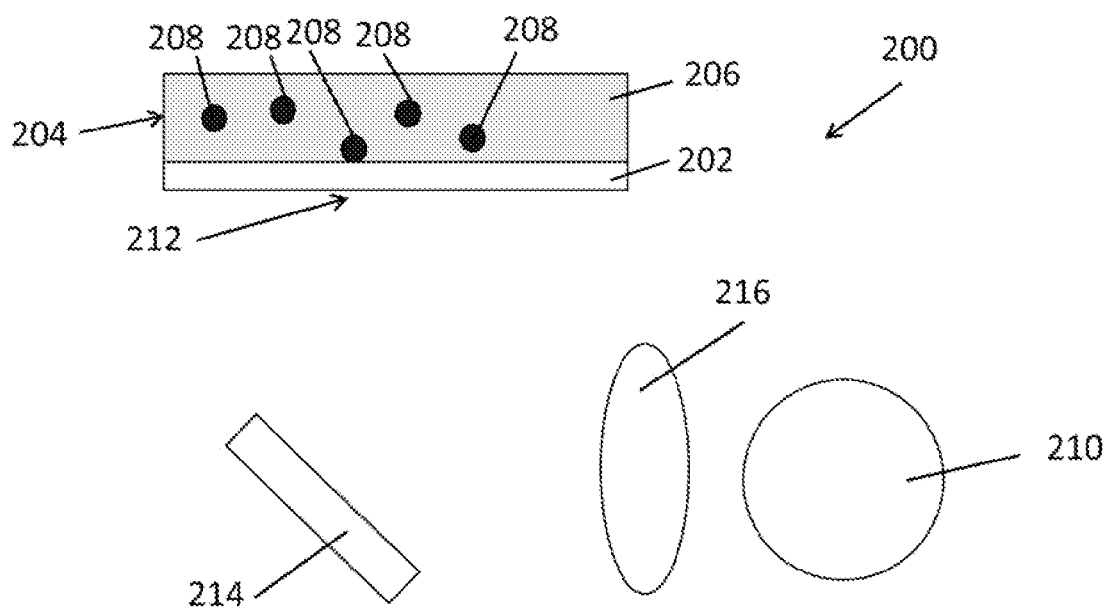
FIG. 4 is a schematic illustration of an example system as disclosed herein for analyte sensing with optothermally generated bubbles in biphasic liquid samples.

Referring now to FIG. 4, in some examples the systems 200 can further comprise a first lens comprising a beam expander 216 configured to expand the illumination from the light source 210 before illuminating the first location 212 of the optothermal substrate 202 and/or before illuminating the mirror 214.

Figure 5:
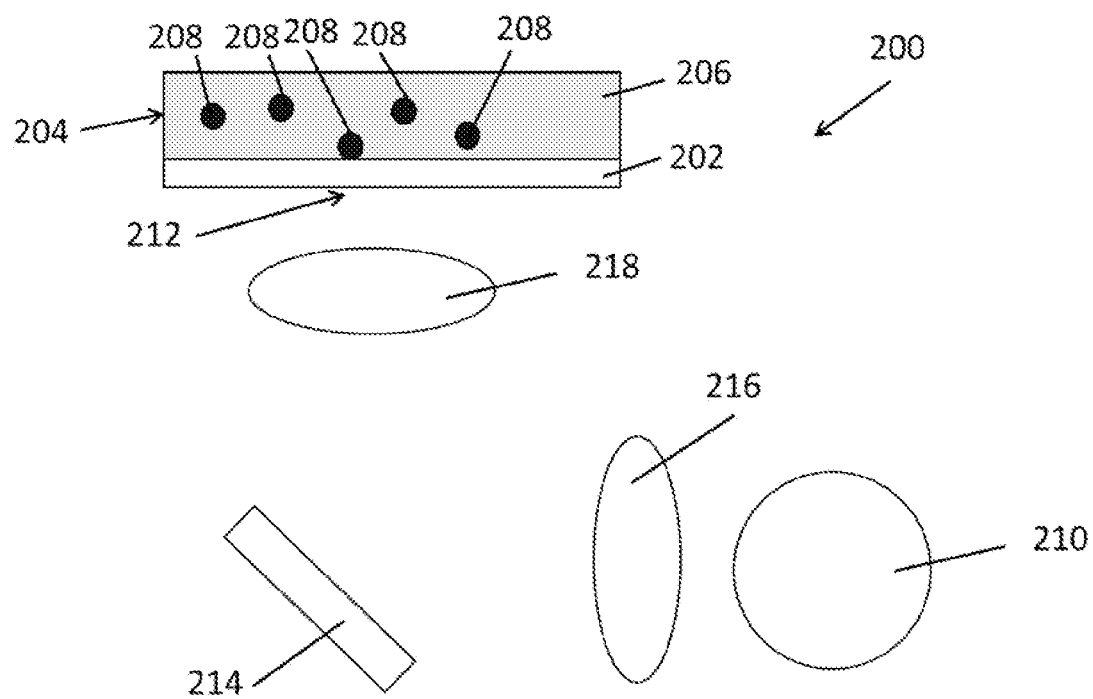
FIG. 5 is a schematic illustration of an example system as disclosed herein for analyte sensing with optothermally generated bubbles in biphasic liquid samples.

Referring now to FIG. 5, in some examples the systems 200 can further comprise a second lens comprising a microscope objective 218 configured to focus the electromagnetic radiation from the light source 210 and/or the mirror 214 to the first location 212.

Figure 6:
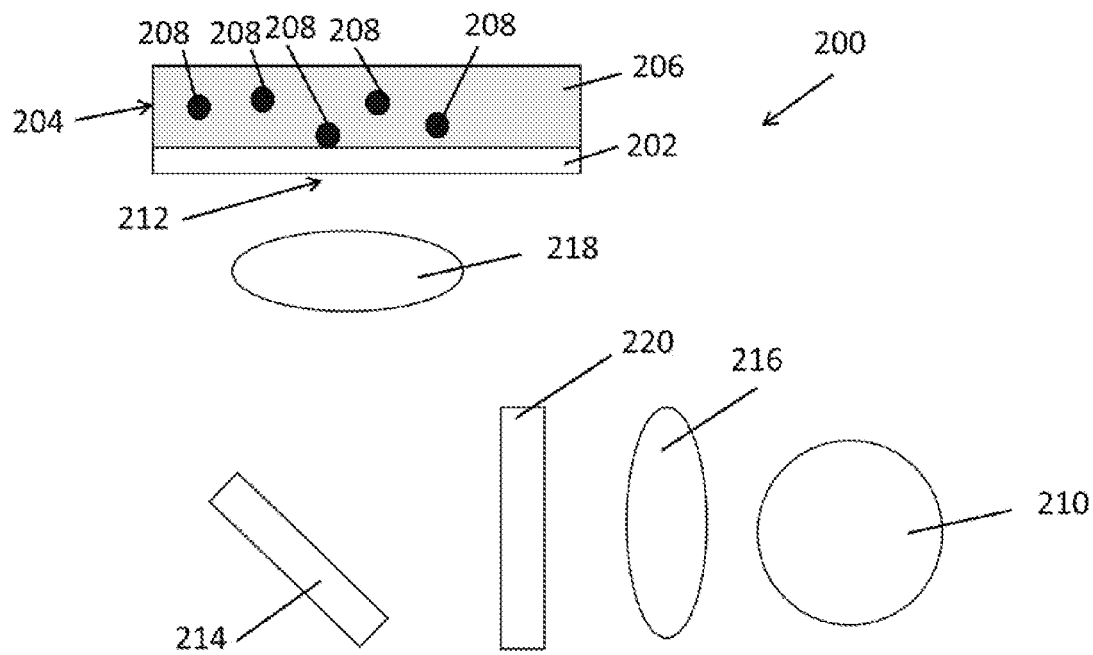
FIG. 6 is a schematic illustration of an example system as disclosed herein for analyte sensing with optothermally generated bubbles in biphasic liquid samples.

In some examples the systems 200 can further comprise a shutter 220. The shutter 220 can, for example, have an open state and a closed state. Referring now to FIG. 6, in some examples, the system 200 is aligned such that the closed state of the shutter interrupts the illumination of the optothermal substrate 202 at the first location 212 by the light source 210.

Figure 7:
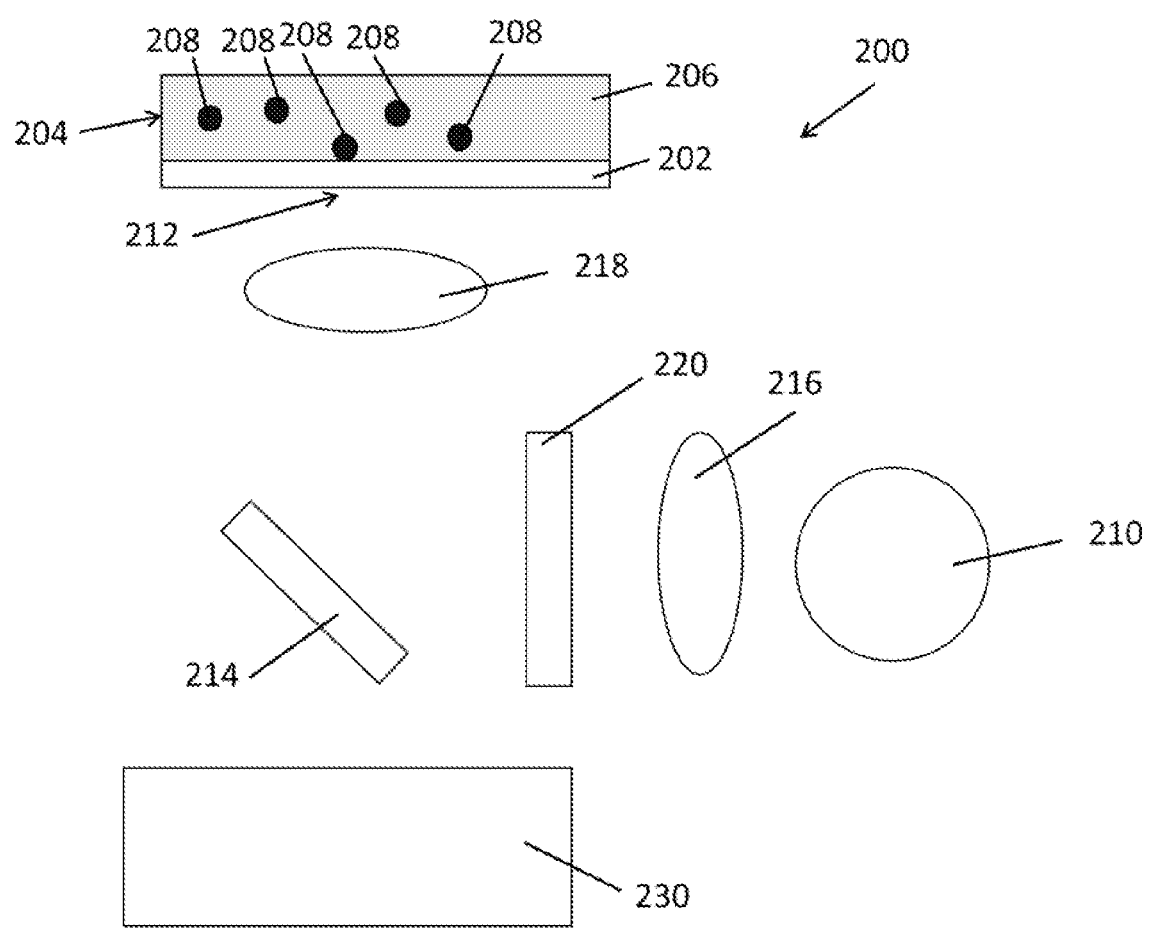
FIG. 7 is a schematic illustration of an example system as disclosed herein for analyte sensing with optothermally generated bubbles in biphasic liquid samples.

Referring now to FIG. 7, in some examples the systems 200 can further comprise an instrument 230 configured to capture an electromagnetic signal from at least a portion of the deposited portion of the plurality of analytes, at least a portion of the optothermal substrate 202 proximate the first location 212, or a combination thereof. The instrument 230 can comprise, for example, a camera, an optical microscope, an electron microscope, a spectrometer, or combinations thereof. Examples of spectrometers include, but are not limited to, Raman spectrometers, UV-vis absorption spectrometers, IR absorption spectrometers, fluorescence spectrometers, and combinations thereof.

Figure 8:
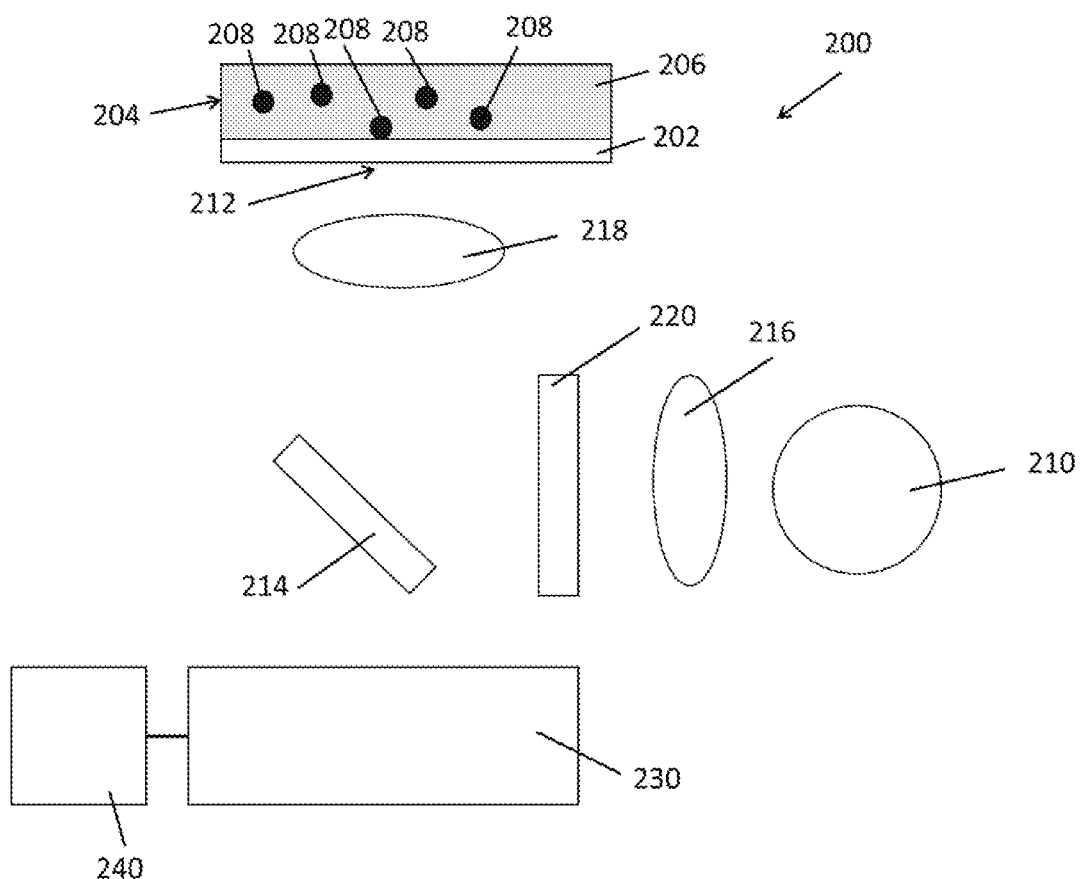
FIG. 8 is a schematic illustration of an example system as disclosed herein for analyte sensing with optothermally generated bubbles in biphasic liquid samples.

In some examples, the systems 200 can further comprise a computing device 240 configured to receive and process the electromagnetic signal from the instrument 230, such as shown in FIG. 8.

Figure 9:
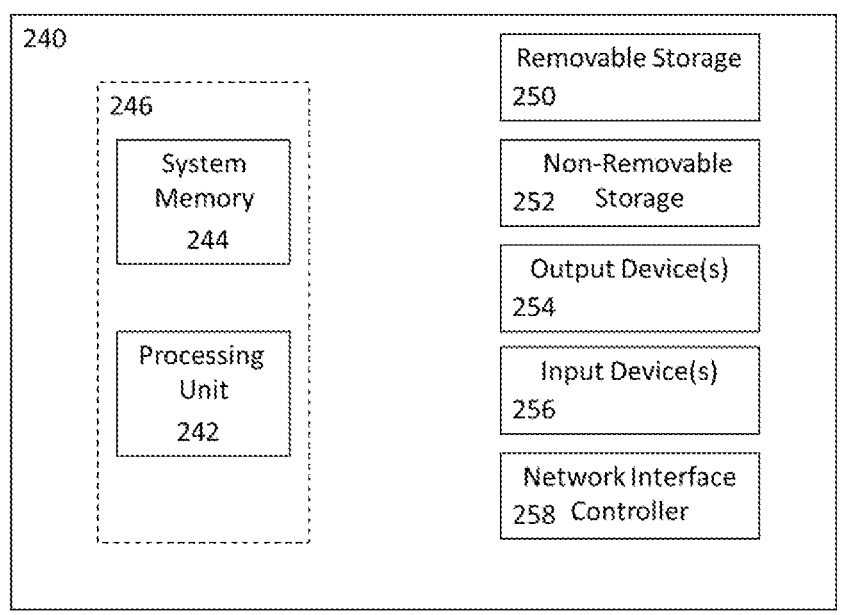
FIG. 9 is a schematic illustration of an example computing device.

FIG. 9 illustrates an example computing device 240 upon which examples disclosed herein may be implemented. The computing device 240 can include a bus or other communication mechanism for communicating information among various components of the computing device 240. In its most basic configuration, computing device 240 typically includes at least one processing unit 242 (a processor) and system memory 244. Depending on the exact configuration and type of computing device, system memory 244 may be volatile (such as random access memory (RAM)), non-volatile (such as read-only memory (ROM), flash memory, etc.), or some combination of the two. This most basic configuration is illustrated in FIG. 9 by a dashed line 246. The processing unit 242 may be a standard programmable processor that performs arithmetic and logic operations necessary for operation of the computing device 240.

The computing device 240 can have additional features/ functionality. For example, computing device 240 may include additional storage such as removable storage 250 and non-removable storage 252 including, but not limited to, magnetic or optical disks or tapes. The computing device 240 can also contain network connection(s) 258 that allow the device to communicate with other devices. The computing device 240 can also have input device(s) 256 such as a keyboard, mouse, touch screen, antenna or other systems configured to communicate with the camera in the system described above, etc. Output device(s) 254 such as a display, speakers, printer, etc. may also be included. The additional devices can be connected to the bus in order to facilitate communication of data among the components of the computing device 240.

The processing unit 242 can be configured to execute program code encoded in tangible, computer-readable media. Computer-readable media refers to any media that is capable of providing data that causes the computing device 240 (i.e., a machine) to operate in a particular fashion. Various computer-readable media can be utilized to provide instructions to the processing unit 242 for execution. Common forms of computer-readable media include, for example, magnetic media, optical media, physical media, memory chips or cartridges, a carrier wave, or any other medium from which a computer can read. Example computer-readable media can include, but is not limited to, volatile media, non-volatile media and transmission media.

Volatile and non-volatile media can be implemented in any method or technology for storage of information such as computer readable instructions, data structures, program modules or other data and common forms are discussed in detail below. Transmission media can include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 242 can execute program code stored in the system memory 244. For example, the bus can carry data to the system memory 244, from which the processing unit 242 receives and executes instructions. The data received by the system memory 244 can optionally be stored on the removable storage 250 or the non-removable storage 252 before or after execution by the processing unit 242.

The computing device 240 typically includes a variety of computer-readable media. Computer-readable media can be any available media that can be accessed by device 240 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 244, removable storage 250, and non-removable storage 252 are all examples of computer storage media.

Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 240. Any such computer storage media can be part of computing device 240.

It should be understood that the various techniques described herein can be implemented in connection with hardware or software or, where appropriate, with a combination thereof. Thus, the methods, systems, and associated signal processing of the presently disclosed subject matter, or certain aspects or portions thereof, can take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs can implement or utilize the processes described in connection with the presently disclosed subject matter, e.g., through the use of an application programming interface (API), reusable controls, or the like. Such programs can be implemented in a high level procedural or object-oriented programming language to communicate with a computer system. However, the program(s) can be implemented in assembly or machine language, if desired. In any case, the language can be a compiled or interpreted language and it may be combined with hardware implementations.

In certain examples, the system 200 comprises a computing device 240 comprising a processor 242 and a memory 244 operably coupled to the processor 242, the memory 244 having further computer-executable instructions stored thereon that, when executed by the processor 242, cause the processor 242 to: receive the electromagnetic signal captured by the instrument 230: process the electromagnetic signal to determine a property of the biphasic liquid sample 204; and output the property of the biphasic liquid sample 204.

The analysis of signals captured by the instrument can be carried out in whole or in part on one or more computing device. For example, the system may comprise one or more additional computing device.

In some examples, the electromagnetic signal received by the processor from the instrument 230 can comprise an image, a spectrum (e.g., Raman, UV-vis, IR, fluorescence), a micrograph, or combinations thereof. The property of the biphasic liquid sample 204 can, for example, comprise the presence of the surface droplet, the presence of the bubble, the presence of the deposited portion of the plurality of analytes, or a combination thereof.

Methods of Use

Also disclosed herein are methods of use of the devices and/or systems described herein.

The systems, methods, and devices described herein are efficient (e.g., use low biphasic liquid sample volumes), rapid (e.g., completion of analysis in minutes), accurate, and flexible (e.g., a variety of aqueous solutions such as a variety of bodily fluids can be used). As such, the systems, methods, and devices described herein are well suited for use in numerous sensing applications and/or in point-of-care (POC) applications.

For example, also described herein are methods of use of any of the devices described herein and/or any of the systems described herein to diagnose and/or monitor a disease in a subject by determining the property of the biphasic liquid sample. In some examples, the plurality of analytes comprise a pathogen, a biomarker, or a combination thereof, the property of the biphasic liquid sample comprises the presence of the deposited portion of the plurality of analytes. Examples of diseases include, but are not limited to, neurodegenerative diseases, infectious diseases, rheumatologic diseases, genetic diseases, acute and chronic respiratory diseases, gastrointestinal and liver diseases, dermatologic diseases, and combinations thereof. In some examples, the disease can comprise a respiratory infection. In some examples, the disease can comprise a viral infection, such as with an influenza virus, a coronavirus, or a combination thereof. In some examples, the disease can comprise an infection with SARS coronavirus, SARS coronavirus 2, or a combination thereof. In some examples, the methods can further comprise selecting a course of therapy for the subject based on the property of the biphasic liquid sample.

A number of embodiments of the invention have been described. Nevertheless, it will be understood that various modifications may be made without departing from the spirit and scope of the invention. Accordingly, other embodiments are within the scope of the following claims.

The examples below are intended to further illustrate certain aspects of the systems and methods described herein, and are not intended to limit the scope of the claims.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of measurement conditions, e.g., component concentrations, temperatures, pressures and other measurement ranges and conditions that can be used to optimize the described process.

Example 1—Enhancing Surface Capture and Sensing of Proteins with Low-Power Optothermal Bubbles in a Biphasic Liquid ABSTRACT. Molecular binding events in surface-based biosensing are inherently governed by passive diffusional transport of molecules in solution to surface-immobilized counterparts. An optothermally generated surface microbubble in fluid can quickly drive the accumulation of solutes at the bubble-surface interface due to high-velocity fluid flows. Despite its potential as a concentrating component, however, the incorporation of bubble generation into protein-based sensing is limited by high power and temperature required in aqueous media. Herein, a perfluoropentane (PFP)-in-water biphasic system is reported, which is capable of generating microbubbles at low optical power, thus enhancing the surface concentration and capture of proteins. By formulating perfluoropentane as a volatile, water-immiscible liquid component in the aqueous host, the threshold optical power for bubble formation was effectively reduced to the extent that the immunobinding affinity of proteins was maintained. Zwitterionic surface modification was further exploited to prevent unwanted printing of proteins during bubble generation. In a single protein-protein interaction model, surface binding of dispersed proteins to capture proteins was enhanced by one order of magnitude within one minute in the bubble-concentrated system, compared to that obtained from uncontrolled incubation for 30 min. This proof-of-concept study exploiting fluid formulation and optothermal add-on paves an effective way towards improving the performances of sensors and spectroscopies.

INTRODUCTION. Surface-based biosensing has been regarded as a reliable platform for the facile separation of analytes and/or probes from solution to solid surface through which surface-confined readout is enabled. Besides optimal pairing of binding species (e.g., surface capture and probe molecules) with molecular/surface designs (Nakatsuka N et al. *ACS Appl. Maier. Interfaces* 2018, 10 (28), 23490-23500; Vaish A et al. *ACS Chem. Neurosci.* 2010, 1 (7), 495-504), there have been multifaceted approaches to further improve sensing performance in terms of throughput and sensitivity. Signal amplification strategies in which signal from a single molecular binding event is amplified by enzymes became a gold standard of immunoassays. Nanocatalysts (Loynachan C N et al. *ACS Nano* 2018, 12 (1), 279-288), atom transfer radical polymerization (Liu Y et al. *Anal. Chem.* 2012, 84 (7), 3179-3186; Yuan L et al. *Anal. Chem.* 2012, 84 (24), 10737-10744), and multiple probe-loaded carriers (Chikkaveeraiah B V et al. *Biosens. Bioelectron.* 2011, 26 (11), 4477-4483) were exploited in efforts of replacing enzymes or further amplification. On the other hand, color change by growth of plasmonic nanocrystals was shown to be an alternative, sensitive signal-transducing mode for visual detection (Rodriguez-Lorenzo L et al. *Nat. Mater.* 2012, 11 (7), 64-607; De La Rica R et al. *Nat. Nanotechnol.* 2012, 7 (12), 821-824).

Apart from these approaches at the signal transduction side, physical concepts have also been utilized at the surface capture/binding step. Binding events in surface-based platforms are governed by passive diffusional transport of suspending molecules (i.e., analytes and/or probes) in the bulk solution toward surface-immobilized capture counterparts in addition to the binding affinity of interacting molecules. In a typical sandwich-type enzyme-linked immunosorbent assay (ELISA), each surface binding step takes 30 minutes to an hour, indicating the diffusion-driven incubation process as a time-limiting step. In this context, sensing performance can be improved if the solution is continuously mixed during incubation or the concentration of solutes is conditionally enhanced near the surface. Such diffusion-breaking conditions have been demonstrated with several concepts: evaporation of solution on a superhydrophobic surface (De Angelis F et al. *Nat. Photonics* 2011, 5 (11), 682-687), acoustic streaming (Maturos T et al. *Lab Chip* 2012, 12 (1), 133-138), cavitation microstreaming (Liu R H et al. *Anal. Chem.* 2003, 75 (8), 1911-1917), AC electrokinetics in microfluidic systems (Liu X et al. *Sensors Actuators A Phys.* 2011, 171 (2), 406-413), and artificial microswimmers (Morales-Narvádez E et al. *Small* 2014, 10 (13), 2542-2548), as well as thermo- and electrophoresis-based approaches in a nanopore setting (Nicoli F et al. *Nano Lett.* 2014, 14(12), 6917-6925; Crick C R et al. *ACS Photonics* 2017, 4 (11), 2835-2842; Shi X et al. *Nano Lett.* 2018, 18 (12), 8003-8010).

The capability of photothermally generated microbubbles to accumulate and print colloidal particles at the bubble-substrate interface through Marangoni convection has been demonstrated previously (Lin L et al. *Nano Lett.* 2016, 16 (1), 701-708). The concentration by bubble generation can even induce supersaturation of ions high enough to enable the crystallization of immiscible metallic nanoalloys (Rajeeva B B et al. *Matter* 2019, 1 (6), 1606-1617). Owing to its fast buildup of strong convective flow based on surface tension gradient and subsequent accumulation of solutes near the substrate, a microbubble is a fascinating candidate as an advanced sensor component for improvements both in time and sensitivity. Biological studies based on the photothermal bubble concentration have been reported for sensing of small molecules (Karim F et al. *Nanoscale* 2019, 11 (43), 20589-20597) and deposition of bacteria (Tokonami S et al. *Sci. Adv.* 2020, 6(9), eaaz5757). However, the application of a bubble-generating scheme to protein-based sensing imposes a major challenge stemming from the high temperatures (>100° C.) needed to generate a bubble in an aqueous system.

Direct exposure of proteins to such a high temperature, which is inevitable in a typical surface-immobilized sensing scenario, affects the structure of proteins, leading to the loss of their immunobinding properties (Wang J et al. *Biomacromolecules* 2012, 13 (2), 559-564; Wang W et al. *J. Pharm. Sci.* 2007, 96 (1), 1-26) (See FIG. 24 for the optothermal effect on the immunobinding property of surface-coated immunoglobulin G). Due to the thermal degradation of proteins, the target analytes of sensors exploiting thermal concentration would have been limited to small molecules and bacteria.

Figure 10:
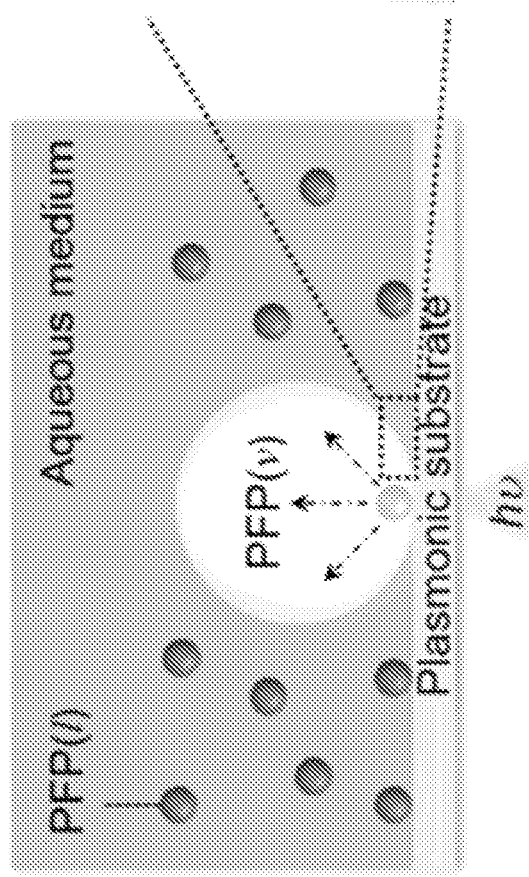
FIG. 10-FIG. 11. Scheme of bubble-enhanced surface capture of proteins and description of biphasic fluid.
Figure 11:
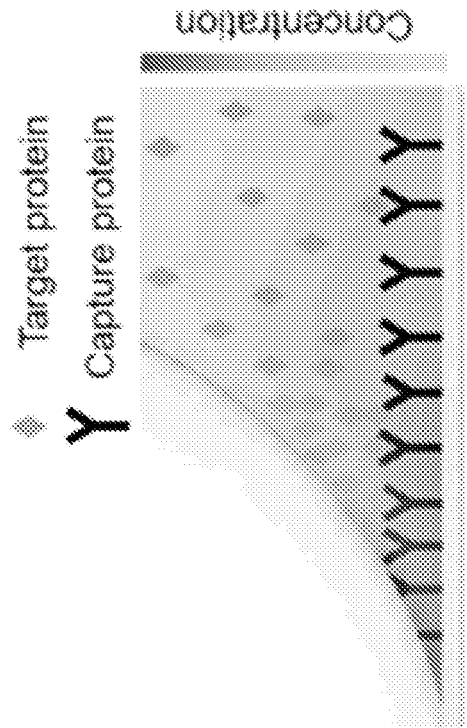

To overcome this limitation, it was hypothesized that a bubble could be optothermally generated at a lower optical power and temperature if volatile liquid droplets suspended in an aqueous medium are present on a plasmonic substrate. Accordingly, criteria for selection of such liquids include low boiling point, minimal water miscibility, and inertness toward proteins. Among a wide variety of candidates available, attention was given to a material category, called perfluorocarbons (PFCs). Perfluorocarbons have been considered in the biomedical field as a candidate material for ultrasonography, blood substitute, and liquid breathing due to their bio-inertness, high gas solubility, hydro-/lipophobicity, and/or low boiling point (Lin C Y et al. *Nanomedicine Nanotechnology. Biol. Med.* 2014, 10 (1), 67-76; Yang P et al. *Biomaterials* 2014, 35 (6), 2079-2088: Diaz-López R et al. *Pharm. Res.* 2010, 27 (1), 1-16; Riess J G. *Arlif. Cells, Blood Substitutes. Biotechnol.* 2005, 33 (1), 47-63; Rapoport N et al. *J. Control. Release* 2011, 153 (1), 4-15; Cosco D et al. *J. Fluor. Chem.* 2015, 171, 18-26). Spurred by these unique material properties along with photothermal control over flow dynamics, a biphasic fluid system where perfluorocarbon droplets are emulsified in an aqueous medium is reported herein for low-power bubble generation and enhancement of protein-protein binding at the substrate driven by bubble-mediated local concentration (FIG. 10, FIG. 11). Perfluoropentane (CsF, PFP) was chosen for its low boiling temperature (~30° C.) as a bubble-generating component. Threshold optical power for bubble generation was reduced to 33% of that in a pure aqueous medium. The generated bubble was able to induce Marangoni flow due to surface tension gradient, which was large enough to accumulate proteins from the bulk solution near the bubble/substrate interface. For the further demonstration of bubble-enhanced protein binding, a plasmonic substrate with a strong optothermal conversion efficiency was modified with zwitterionic molecules in order to address a printing issue (i.e., analytes were unintentionally adsorbed on the substrate) witnessed during the bubble-induced concentration of analytes. One-order-of-magnitude enhancement in surface capture efficiency was observed within one minute in a single protein-protein binding model, compared to diffusion-limited incubation for 30 minutes.

Results and Discussion

Figure 12:
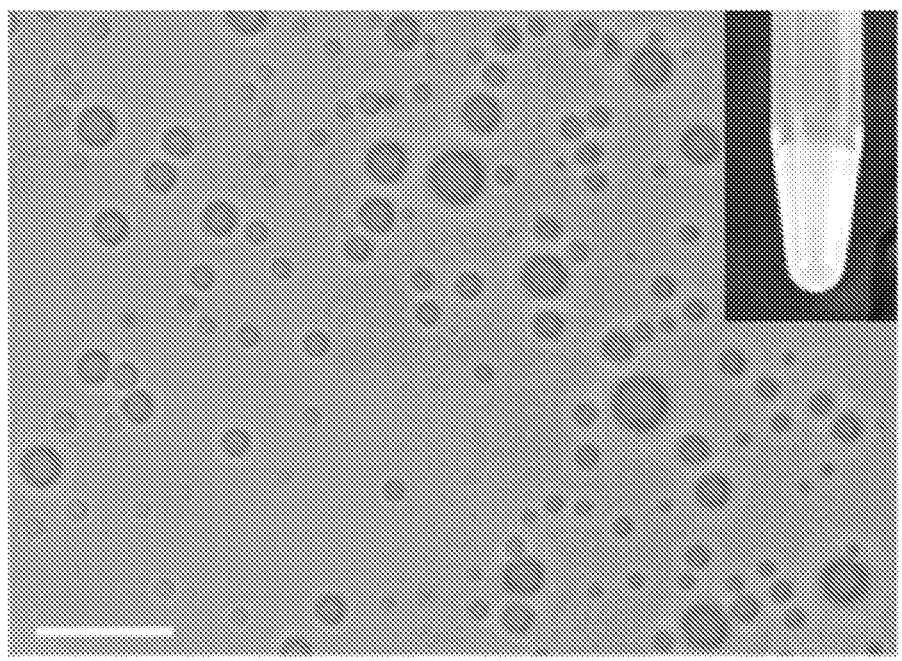
FIG. 12. Optical image of perfluoropentane droplets (scale bar: 10 µm). Inset of (FIG. 12) is a photograph of perfluoropentane-in-water fluid.
Figure 13:
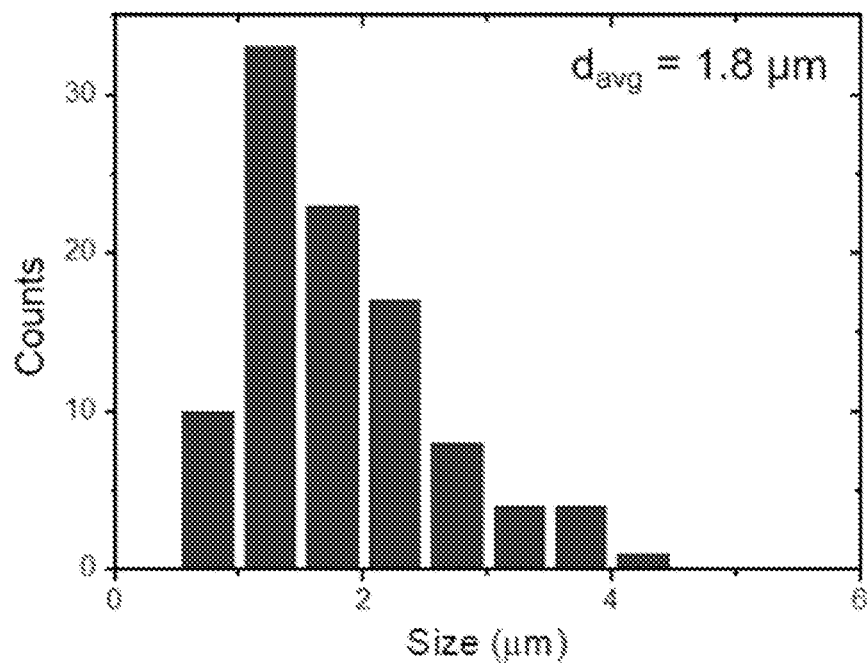
FIG. 13. Size distribution of perfluoropentane droplets with a total number n=100.

Description of bubble generation in the perfluoropentane-in-water system. A perfluoropentane-in-water emulsion was prepared by adding perfluoropentane into the aqueous medium under sonication. As a working buffer for protein, phosphate buffer saline (PBS) was used as the aqueous medium. The fluid system was comprised of microscale perfluoropentane droplets near the plasmonic substrate with an average size of 1.8 μm, which was estimated from optical microscopic images (FIG. 12, FIG. 13). The plasmonic substrate was comprised of arrays of gold nanoislands (Au NIs).

Figure 25:
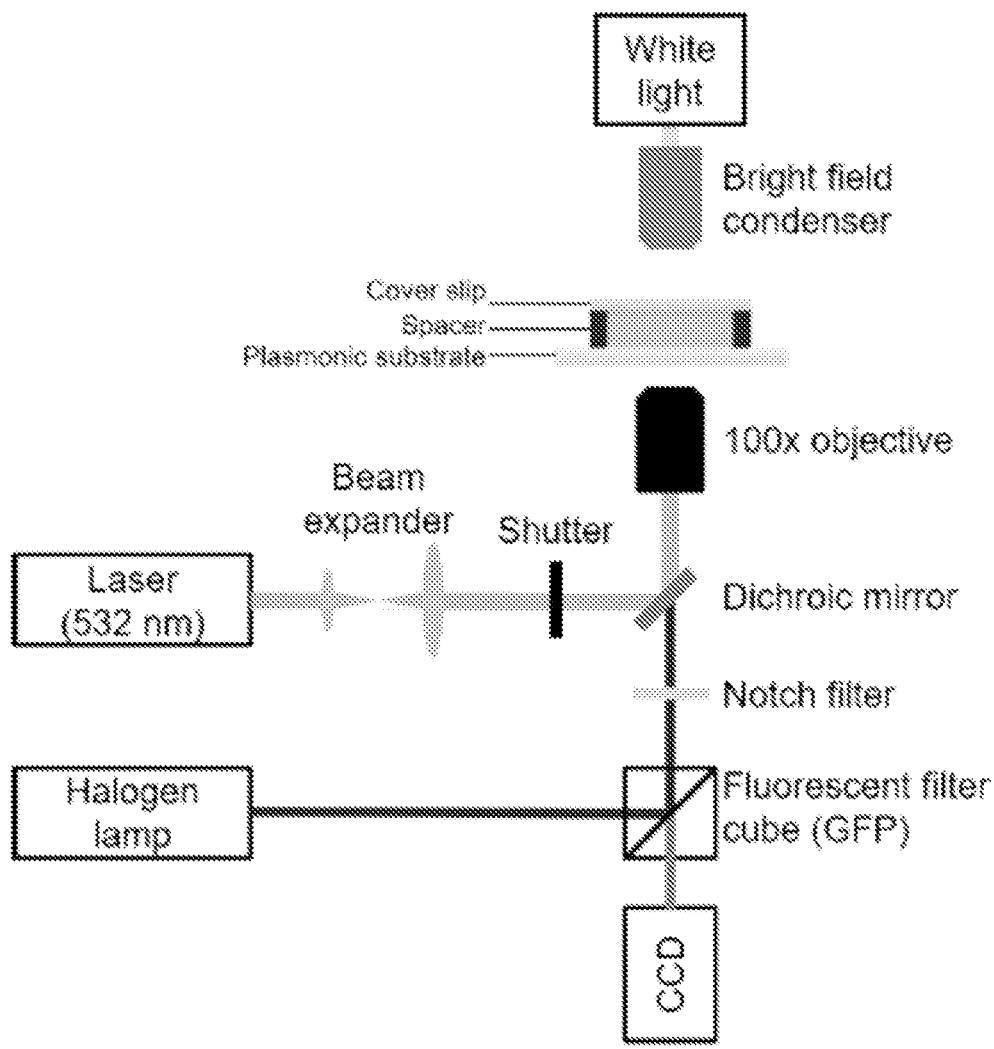
FIG. 25. Optical setup for optothermal bubble generation and optical/fluorescent microscopy.
Figure 26:
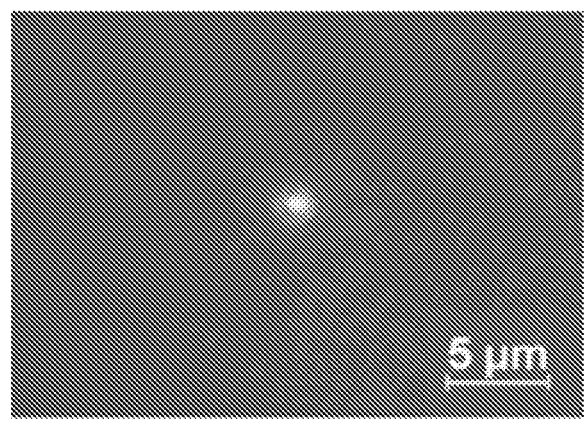
FIG. 26. Bubble generated in pure phosphate buffer saline. A 1.4 µm (in diameter) bubble was generated upon laser illumination (0.78 mW/µm$^2$). Accumulation of fluorescent proteins (FITC-anti rabbit Immunoglobulin G, 10 µg/mL in solution) was observed at this condition.
Figure 33:
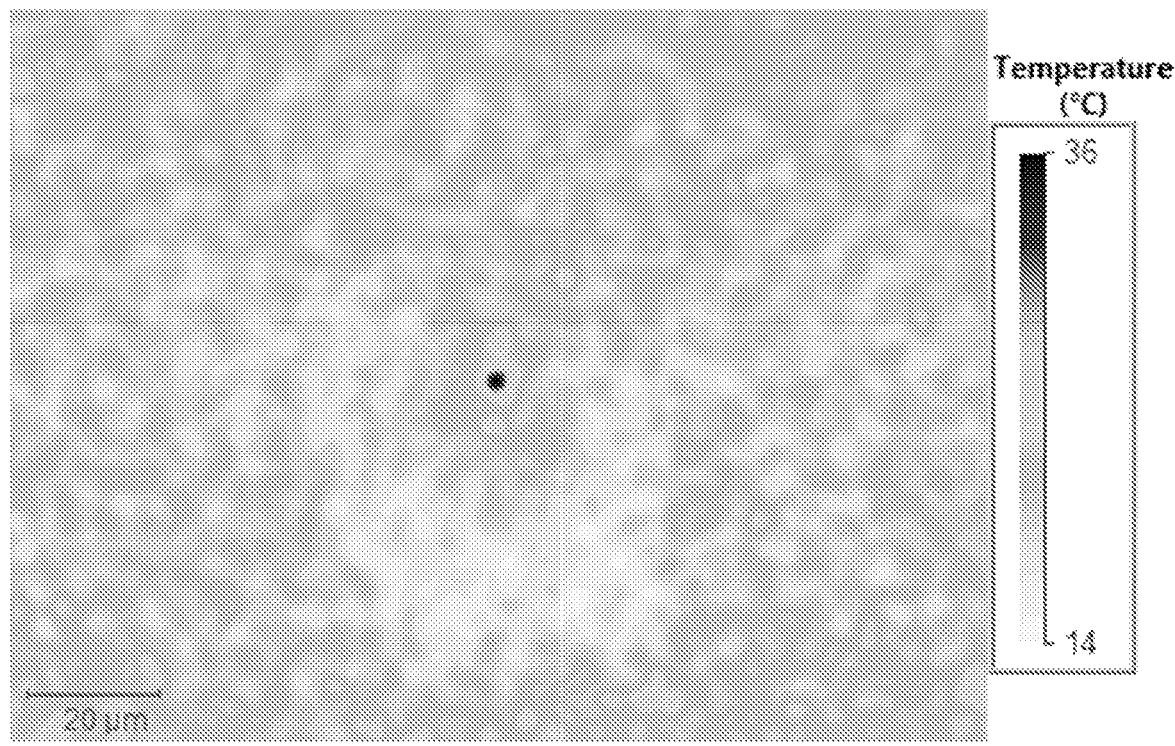
FIG. 33. Measured temperature profile of a plasmonic substrate under biphasic bubble-generating conditions.

Some of the droplet population was observed to be stationary on the substrate, termed as surface droplets. Other droplets were suspended in a colloidal state throughout the host medium. Surface droplets did not disappear or collapse throughout the duration of monitoring. i.e., around 30 minutes, implying that perfluoropentane droplets were stabilized by their high vapor pressure at room temperature (Riess J G. *Artif Cells, Blootx Substitutes, Biotechnol.* 2005, 33 (1), 47-63; Schutt E G et al. *Angew. Chemie—Int. Ed.* 2003, 42(28), 3218-3235) on the solid surface. A continuous wave laser beam (532 nm in wavelength) was focused on the substrate under the surface droplets to generate a microbubble in a setting of an inverted optical microscope (FIG. 25). The threshold of optical power for bubble generation was 0.26 mW/$\mu m^2$, which was one third of that in pure phosphate buffer saline (FIG. 26), at which the maximum temperature of the substrate reached 36° C. at the laser beam center (FIG. 33).

Figure 14:
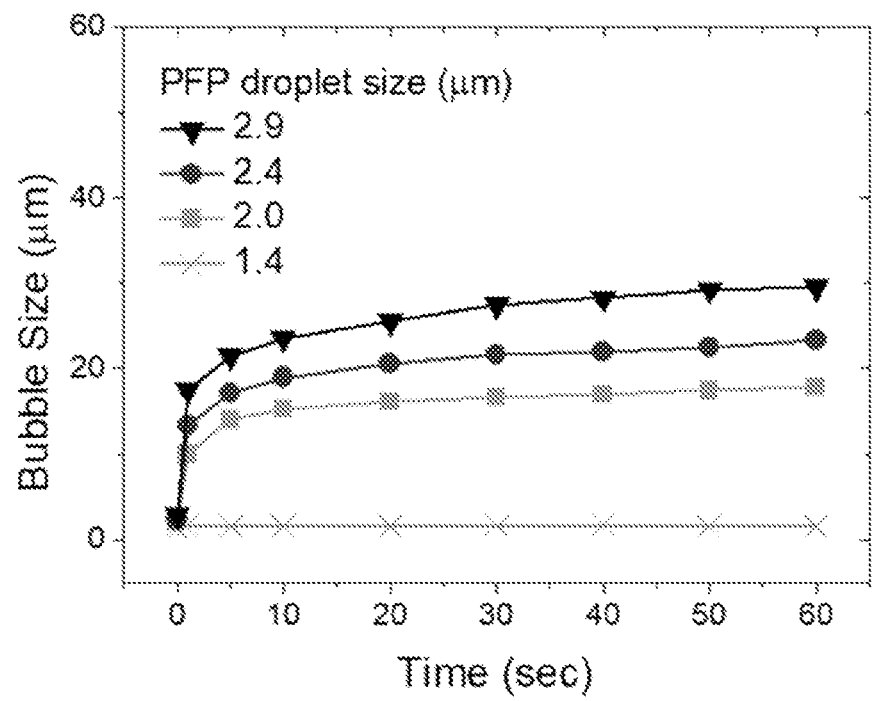
FIG. 14. Bubble generation and concentration of protein. Growth behavior of bubbles arising from perfluoropentane droplets with different diameters.
Figure 15:
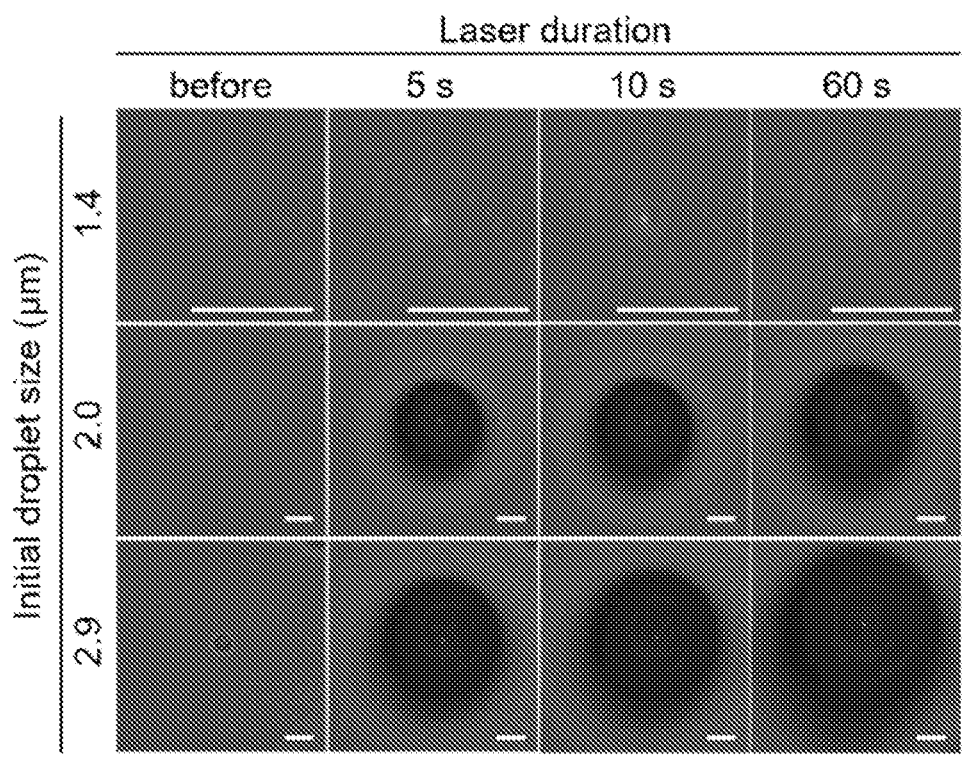
FIG. 15. A series of optical images showing the evolution of bubbles arising from perfluoropentane droplets with different diameters (scale bar: 5 µm).
Figure 27:
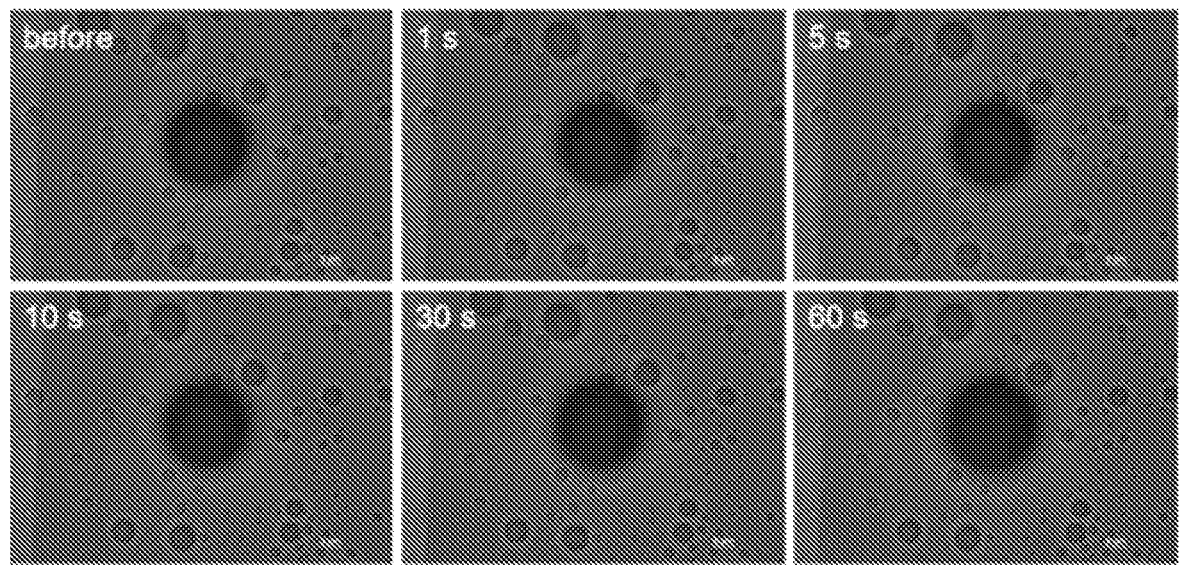
FIG. 27. Bubble behavior upon the switching-off of heating laser beam. A series of optical microscopic images of an optothermally generated bubble were obtained in the course of time after light-off.

As shown in FIG. 14 and FIG. 15, the growth behavior of bubbles under continuous light exposure has a dependence on the initial size of the perfluoropentane droplets. While a droplet of 1.4 μm does not evolve to a bubble, droplets larger than 2.0 μm quickly undergo bubble transformation, reaching more than 10 μm within a few seconds upon light irradiation. After the sharp rise in bubble size, a relative plateau regime was observed with a gradual increase. Similar growth kinetics were observed in droplets of different sizes: larger final bubbles from larger initial droplets. The bubbles do not collapse upon switching off the heating laser beam (FIG. 27).

This droplet-size-dependent bubble growth behavior can originate from intrinsic characteristics of perfluoropentane. In particular, perfluoropentane exhibits a lower thermal conductivity, a lower heat of vaporization, and a higher gas solubility than water (see Table 1 for physical properties of perfluoropentane and water). For bubbles smaller than the critical size, the limited contact area between a perfluoropentane droplet and a substrate would drive thermal energy created by the laser-irradiated substrate to be readily dissipated through the water continuum in contact. The laser beam diameter was around 1.0 μm, which is comparable to droplet sizes examined. Above the critical size of perfluoropentane droplets (around 2.0 μm) and concomitant critical contact area between perfluoropentane and substrate, sufficient heat could accumulate in the basal region of perfluoropentane droplets due to low thermal conductivity of perfluoropentane, resulting in the onset of vaporization. The initial explosive growth is attributable to high gas solubility and volatile nature of perfluoropentane. Assuming that the perfluoropentane droplets are air-saturated, the large amounts of air gas ($N_2$, $O_2$ and $CO_2$) dissolved in perfluoropentane would contribute to the large expansion of bubbles in addition to perfluoropentane vapor once vaporization begins. Moreover, the low heat of vaporization of perfluoropentane could accelerate the vaporization of residual liquid perfluoropentane within the growing bubble.

TABLE 1

Physical properties of perfluoropentane and water.

| | Thermal conductivity [mW/m/K] | Heat of vaporization [cal/g] | Oxygen solubility [ml/l] | Density [g/ml] |
|---|---|---|---|---|
| Perfluoropentane | 5 | 21 | 800 | 1.63 |
| Water | 600 | 540 | 6.3 | 1 |

The steady state afterwards can be reached by a balance between heat supply from the plasmonic substrate and heat loss through the bubble/liquid interface and by evaporation. Upon bubble formation, gas molecules in the aqueous phase can be directed toward the bubble-surface interface and taken up by the bubble as suggested in the cases of water (Wang Y et al. *ACS Nano* 2017, 11 (2), 2045-2051) and n-alkanes (Zaytsev M E et al. *J. Phys. Chem. C* 2018, 122 (49), 28375-28381). A critical bubble diameter exists above which the mass transfer of gas into the bubble exceeds that out of the bubble (Ward C A et al. *J Appl. Phys.* 1982, 53 (9), 6076-6084; Ward C A et al. *J. Appl. Phys.* 1984, 56 (2), 491-500). Stable bubbles that do not collapse and even slowly grow after the light is turned off can be ascribed to this gas influx.

Figure 16:
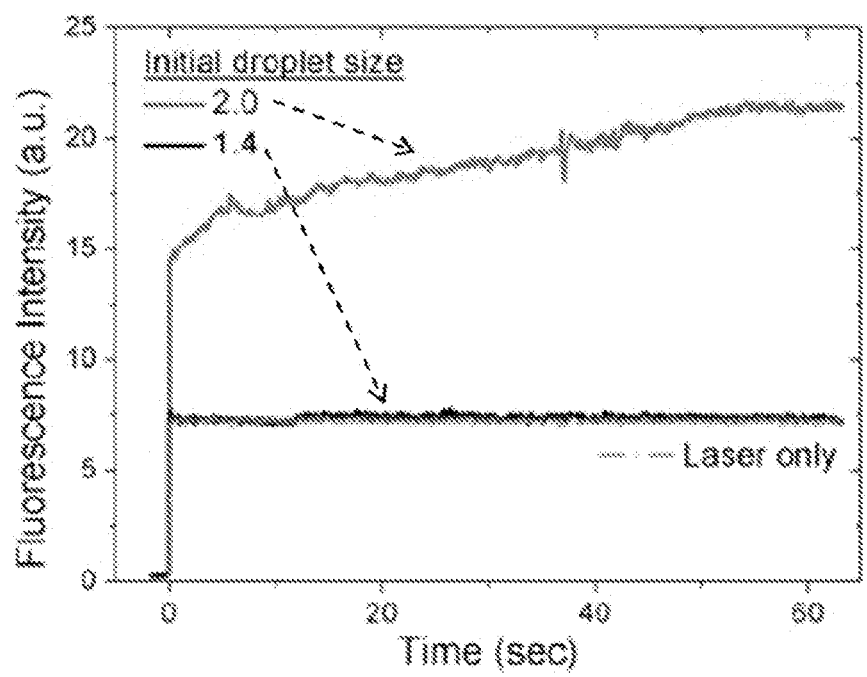
FIG. 16. Temporal evolution of fluorescence intensity (FITC-antirabbit Immunoglobulin G (IgG), 10 µg/mL in phosphate buffer saline) around the laser spot for two perfluoropentane droplets of different sizes. The zero time point indicates the light incident. Fluorescence intensity was measured from the defined region of interest around the laser spot.
Figure 17:
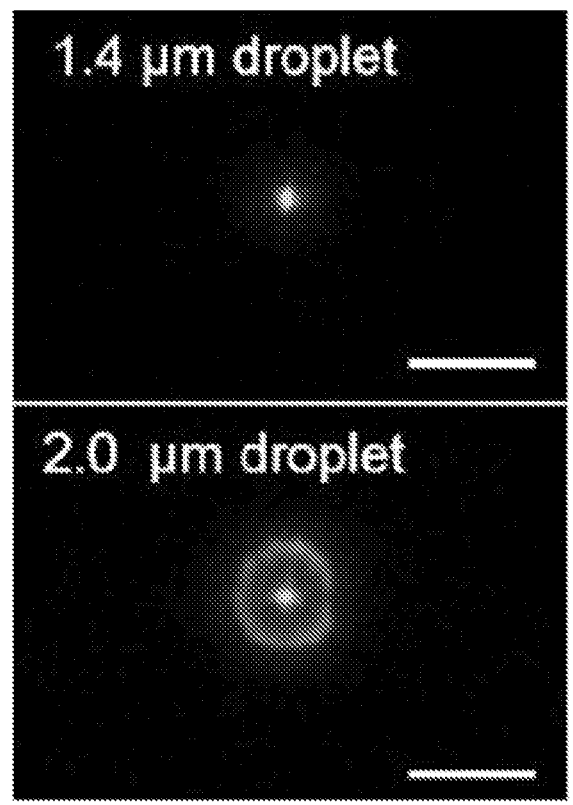
FIG. 17. Fluorescence intensity images (FITC-antirabbit Immunoglobulin G (IgG), 10 µg/mL in phosphate buffer saline) around the laser spot for two perfluoropentane droplets of different sizes (1.4 µm, top panel, and 2.0 µm, bottom panel) after 60 seconds of bubble duration (scale bar: 5 µm) corresponding to the data in FIG. 16.

Bubble-mediated accumulation of proteins at substrate surfaces. Bubble-mediated concentration of proteins was examined by the time-course measurement of fluorescence intensity near bubbles in perfluoropentane-in-water fluid wherein fluorescent proteins are dissolved in the aqueous phase. With a 1.4 μm perfluoropentane droplet, fluorescence intensity is indistinguishable from the laser-only signal (FIG. 16, FIG. 17). Since the droplet of this size does not generate a bubble, as seen in the previous section, the possibility of any nanobubble-related accumulation could be excluded. For a 2.0 μm perfluoropentane droplet, a sharp rise in the average fluorescence intensity was observed in the initial stage of bubble generation, followed by a gradual increase until 50 seconds of light exposure. These results indicate that the transport of proteins from the bulk solution to the substrate surface occurs quickly at the onset of bubble formation and continues gradually for the duration of the bubble formation/expansion.

Figure 18:
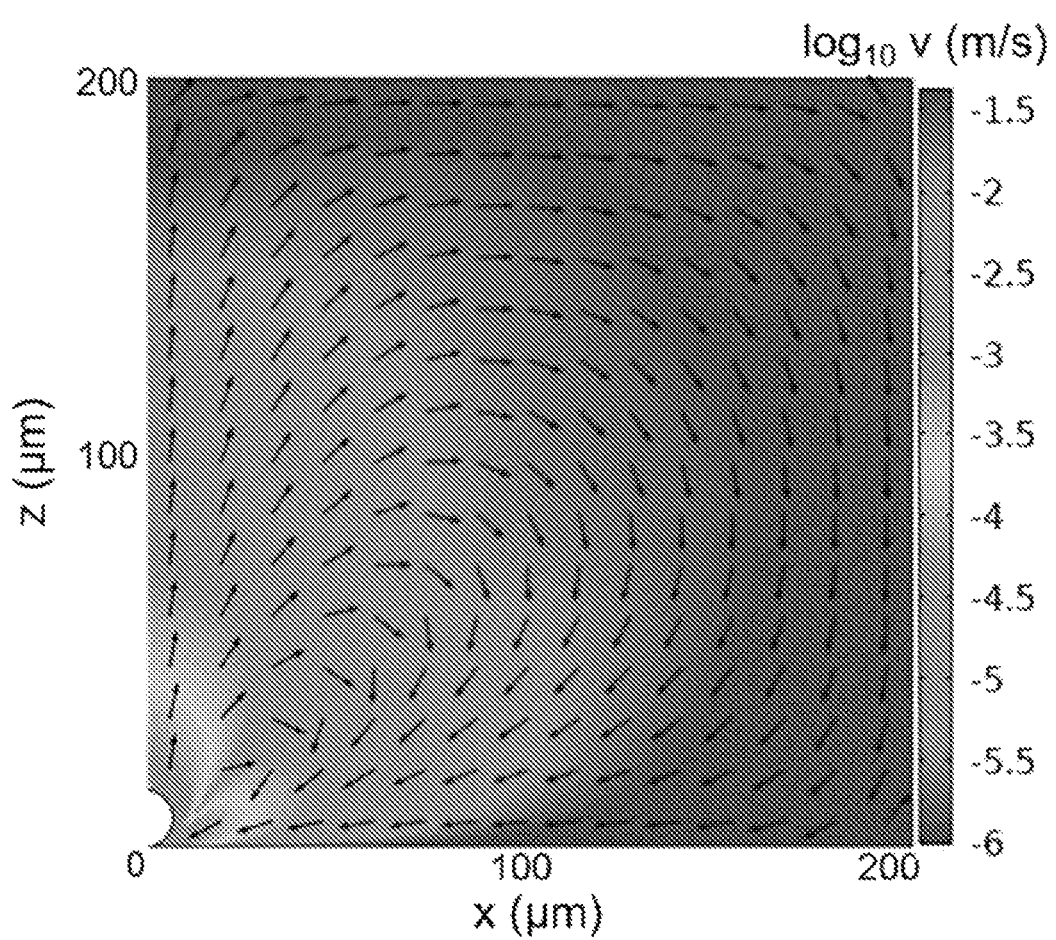
FIG. 18. Simulated velocity profile near the 15 µm bubble. Arrows indicate normalized velocity.

From the simulation shown in FIG. 18, a 15 μm bubble with a temperature difference of 4 K along the bubble-liquid interface is able to build up Marangoni flow with a maximum velocity of 0.04 m/s at the bubble/liquid/solid interfacial region. Although the maximum velocity is much lower than that in pure water (~0.3 m/s) with a 60 K temperature difference (Lin L et al. *Nano Lett.* 2016, 16 (1), 701-708: Kotnala A et al. *Nano Lett.* 2020, 20 (1), 768-779), this biphasic system was capable of delivering and confining proteins to the substrate surface region.

Surface modification to prevent bubble-driven printing of proteins on the substrates. Another issue in applying the concept of bubble concentration to immunosensing has been direct printing of proteins on the substrate at the three-phase contact line. This phenomenon known as bubble printing or bubble pen lithography was reported in the aqueous medium with micro- and nanoparticles (Lin L et al. *Nano Lett.* 2016, 16 (1), 701-708; Rajeeva B B et al. *Matter* 2019, 1 (6), 1606-1617). In an ideal case of bubble-enhanced protein-protein interaction, proteins should be concentrated near the substrate by the bubble without any subsequent printing of the proteins on the substrate that could contribute to the background signal. A surface antifouling coating was considered to overcome this challenge. Zwitterionic groups have been proposed as a good candidate for such a coating, in which the presence of positive and negative charges contribute to the formation of a rigid hydration shell and steric hindrance as well as their hydrophilic nature (He M et al. *Acta Biomater.* 2016, 40 (92), 142-152; Schlenoff J B et al. *Langmuir* 2014, 30 (32), 9625-9636).

Among the zwitterions, phosphatidylcholine (PC) as a major component of cell membranes was chosen for the system described herein. Zwitterionic moieties were introduced to the gold nanoisland substrates through a hybrid lipid bilayer membrane that comprises a supporting alkanethiol self-assembled monolayer (SAM) and a cover layer of phosphatidylcholine lipid (Plant A L. *Langmuir* 1993, 9 (11), 2764-2767: Plant A L et al. Anal. *Biochem.*

Figure 19:
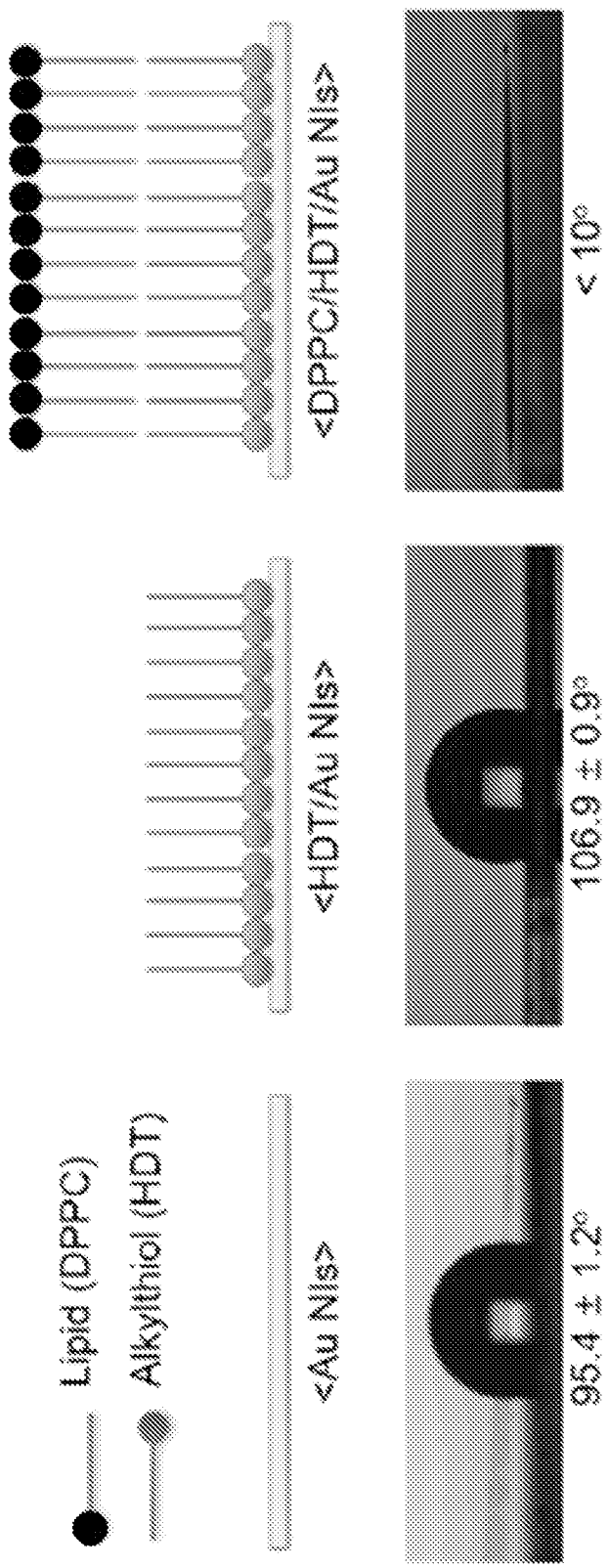
FIG. 19. Zwitterionic surface modification to reduce bubble printing of proteins. Schematic illustration of surface-modified gold nanoislands and their contact angle with a water droplet (3 µL) at each modification step.
Figure 20:
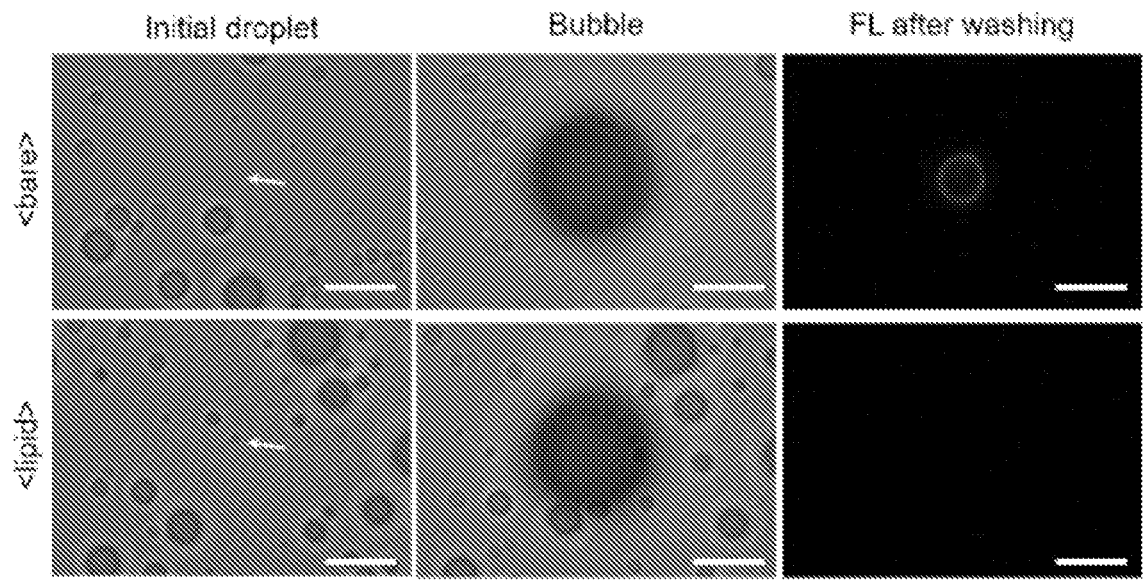
FIG. 20. Zwitterionic surface modification to reduce bubble printing of proteins. Optical images of initial droplets and generated bubbles, and fluorescence images of substrates after bubble concentration of fluorescent proteins (FITC-anti rabbit Immunoglobulin G, 10 µg/mL) for 1 min and subsequent washing (scale bars: 10 µm). Top row is for bare gold nanoisland substrate as indicated by <bare>. Bottom row is for the 1,2-dipalmitoyl-sn-glycero-3-phosphocholine-coated substrate as indicated by <lipid>.
Figure 28:
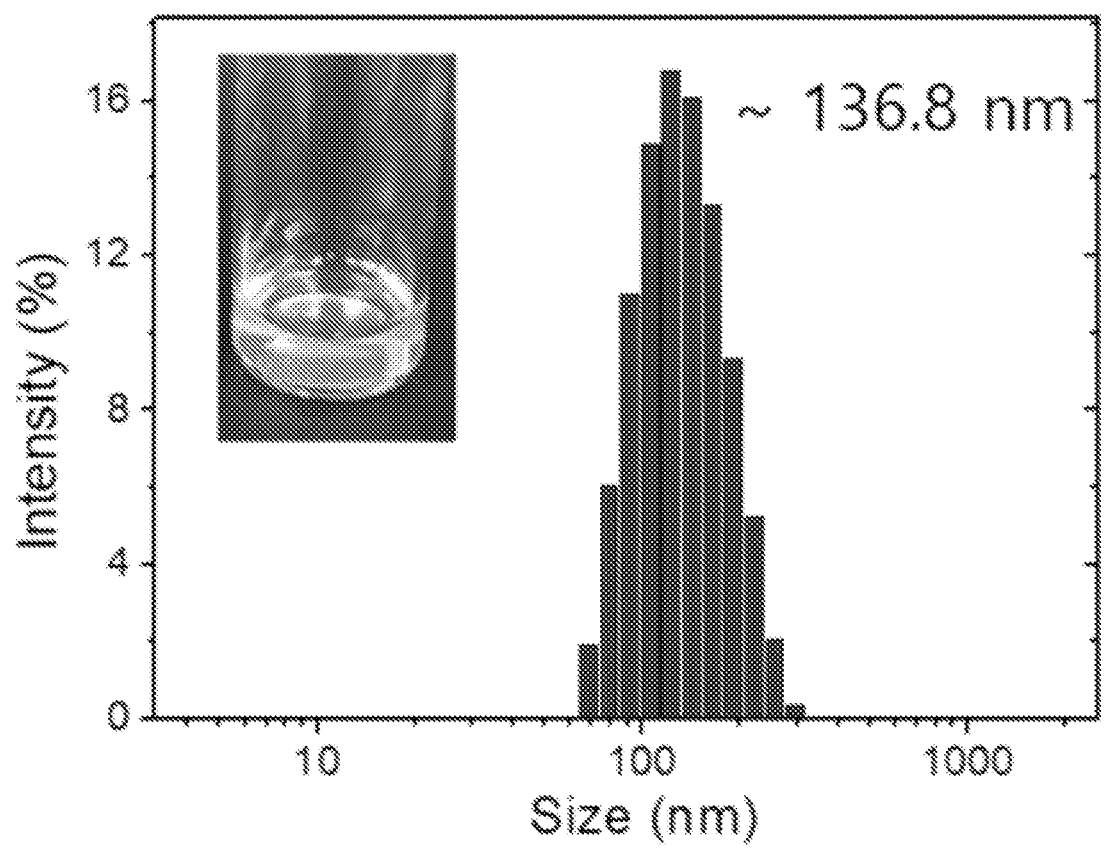
FIG. 28. Intensity-averaged size distribution of 1,2-dipalmitoyl-sn-glycero-3-phosphocholine liposomes recorded by dynamic light scattering. The average diameter of the liposomes is 136.8 nm. Inset is a photograph of liposomes.

1995, 226 (2), 342-348). This scheme was adopted because of the high structural integrity stemming from strong hydrophobic interaction between the two layers as well as strong thiol-gold interaction and minimal fluidity of membranes by highly crystalline self-assembled monolayer (Khan M S et al. *Int. J. Mol. Sci.* 2013, 14 (11), 21561-21597). FIG. 19 shows the schematic of surface modification and the measured contact angle of the gold nanoisland substrate with water at each step to verify the modification process. The modification with alkanethiol (hexadecanethiol. HDT) makes the substrate more hydrophobic, increasing the contact angle from 95.4° to 106.9°. After incubation of this substrate with unilamellar liposomes (FIG. 28) made of 1,2-dipalmitoyl-sn-glycero-3-phosphocholine (DPPC) and subsequent washing, extremely high hydrophilic surface was obtained, characterized by almost perfect wetting of water. As shown in FIG. 20, the amount of fluorescent proteins that remained on the substrate after bubble concentration and washing was significantly reduced in the 1,2-dipalmitoyl-sn-glycero-3-phosphocholine coated substrate, compared to the unmodified substrate.

Figure 21:
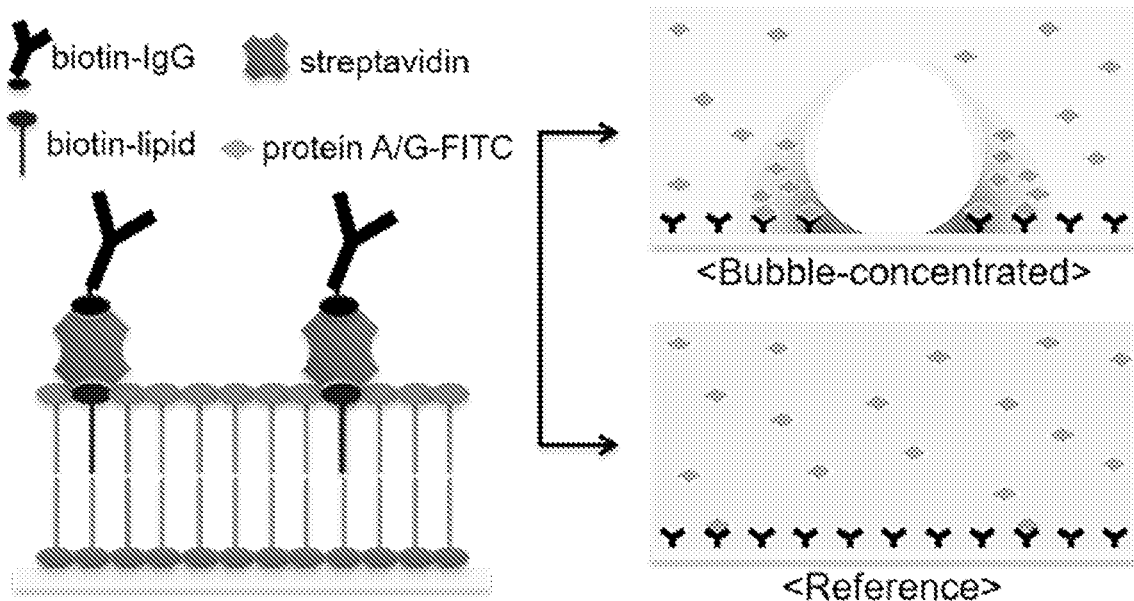
FIG. 21. Bubble-enhanced surface capture of proteins. Schematic diagrams of surface immobilization of capture protein and two assay models: (i) bubble-concentrated and (ii) diffusion-limited incubation as reference.

Bubble-enhanced surface capture of protein. As a model to investigate the effects of bubble on surface capturing of proteins, a scheme of direct analyte capture with a single protein pair was adopted. Immunoglobulin G (IgG), a capture protein, was confined within the lipid layer using biotin-streptavidin conjugation, and FITC-labeled protein A/G was used as a target protein for its high affinity to Immunoglobulin G and for visualizing the degree of surface binding events (FIG. 21). A concentration range of the target was predetermined based on a linear concentration profile after 30 min incubation of the substrate in the solution and subsequent washing, which was considered as a reference. During the preparation of the protein solution, it was found that proteins were localized at the perfluoropentane-droplet-water interface, resulting in less availability of free-standing proteins in the solution. This phenomenon was ascribed to the hydrophobicity of proteins.

Figure 29:
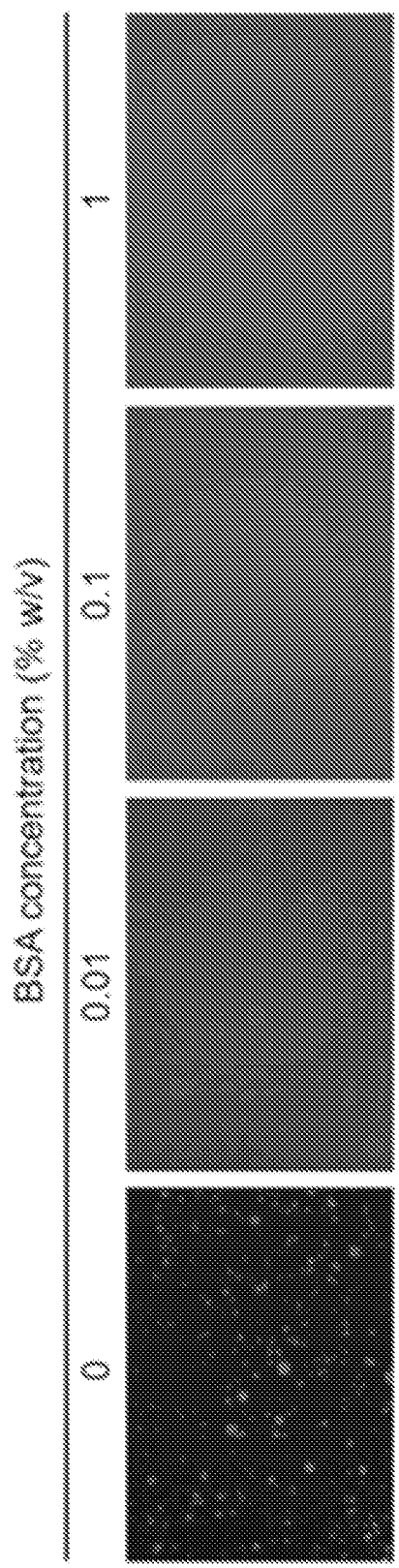
FIG. 29. Fluorescence images of perfluoropentane droplets in water containing FITC-protein A/G (5 µg/mL) with varying concentration of bovine serum albumin.
Figure 31:
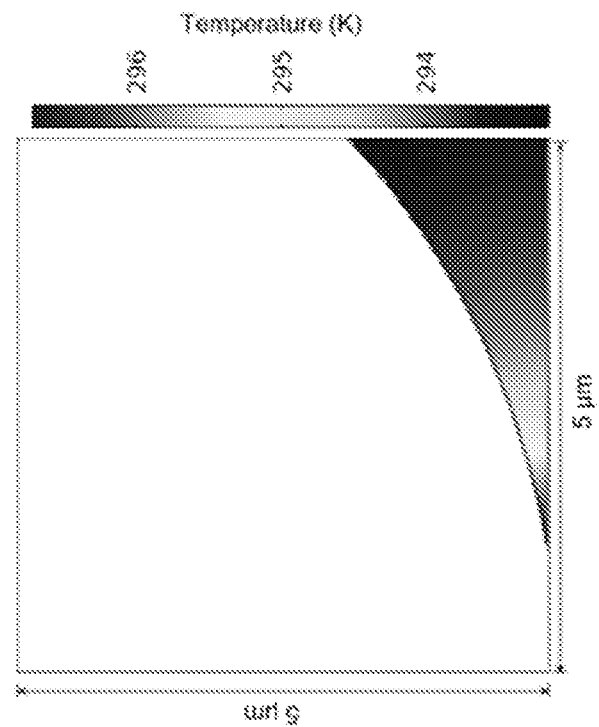
FIG. 30-FIG. 31. Geometry and temperature distribution in fluid dynamics simulation.
Figure 30:
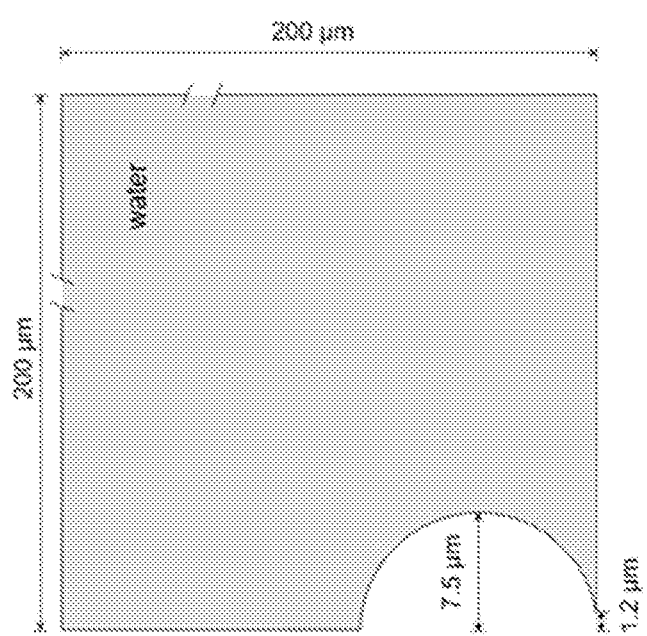

Thus, the final formulation was modified to include bovine serum albumin (BSA), one of the common blocking agents used in immunoassay for reducing nonspecific surface binding. In the presence of bovine serum albumin with increased concentration, fluorescence intensity from the bulk phase was increased while that from the interface-confined fraction of the droplets was reduced, implying bovine serum albumin occupancy on the droplet surfaces (FIG. 29).

For the bubble-enhanced model, bubbles were optothermally generated from perfluoropentane droplets (~2.0 μm) at the substrate surface and sustained for 1 minute, followed by repeated washing of the substrate with phosphate buffer saline. As demonstrated in FIG. 22 and FIG. 23, the bubble-concentrated system has a concentration profile that is about nine times steeper than the profile of the diffusion-limited reference system. It was observed that the enhancement factor was almost similar at each protein A/G concentration examined, maintaining the linearity of the concentration profiles for both systems. Furthermore, this bubble-concentrated system has a time-efficient feature where it takes one minute to obtain the enhanced signal in comparison to 30 minutes of incubation in the reference.

This result indicates that the local concentration near the surface is effectively amplified by bubbles through which the propensity of target-capture collision is increased, eventually leading to the enhanced surface capture as well as reduction in incubation time. In addition to the concentration-driven enhancement of surface capture, there can be a partial contribution from the enhanced protein-protein binding reaction by elevated temperature near the bubble.

CONCLUSIONS. A proof-of-concept study on a low-power bubble-generating system and its application as an in-situ concentrator for enhancing surface capture of proteins has been demonstrated. The formulation of volatile and water-immiscible liquid phase into the aqueous host medium was found to effectively reduce the optical power threshold for bubble generation, enabling the bulk-to-substrate accumulation of proteins with minimal thermal deterioration of protein activity. The bubble growth behavior could be explained in terms of intrinsic properties of perfluoropentane. Together with zwitterionic surface modification, the low-power bubble generation was able to improve the capture efficiency of proteins by one order of magnitude in sensitivity and by 30-fold reduction in time, compared to a diffusion-limited setting.

One of the merits of the bubble-based approach, composed of fluid formulation and an optothermal add-on, resides in its compatibility with conventional surface-based assay platforms. Given the working mode of this concept, the same method can be sequentially applied to multiple steps of solution-to-surface conjugation as in sandwich-type ELISA, e.g., capture antibody/antigen, antigen/probe antibody, probe antibody/secondary antibody, and enzyme/substrate. Collective improvement of its performance in sensitivity and throughput can be expected from enhancements in binding events at each step. The present study can find a wider range of scientific and clinical applications when combined with rational designs of sensor configuration, as well as suggesting a way toward improving the performances of sensors and spectroscopies.

Methods

Materials. Perfluoropentane (PFP, 99.0%) was purchased from FluoroMed, L.P. Phosphate buffer saline (PBS), (+)-Biotin N-hydroxysuccinimide ester (NHS-biotin, ≥98%), rabbit immunoglobulin G (IgG), and fluorescein isothiocyanate (FITC)-conjugated anti-rabbit Immunoglobulin G (produced in goat, in solution containing 1% bovine serum albumin) were purchased from Sigma Aldrich. FITC-conjugated protein A/G (FITC-protein A/G) was purchased from BioVision, 1,2-dipalmitoyl-sn-glycero-3-phosphocholine (DPPC) and 1,2-dioleoyl-sn-glycero-3-phosphoethanolamine-N-(Cap-Biotinyl) (biotin-PE) were obtained from Avanti Polar Lipids, Inc, 1-hexadecanethiol (HDT, 90%) was obtained from Acros Organics and streptavidin (biotechnology grade) from VWR International. All the reagents were used as received.

Characterizations. The hydrodynamic size of liposomes was recorded by dynamic light scattering (DLS) at 25° C. (Zetasizer Nano ZS, Malvern Instruments). Contact angle measurements were conducted with a drop size analyzer (DSA100, KRÜSS GmbH).

Optical setup. An inverted microscope (Nikon Ti-E) with a 100× oil objective (NA 1.3, Nikon) was used. A 532 nm laser (Genesis MX STM-1 W, Coherent) beam was expanded by a 5× beam expander (GBE05-A, Thorlabs) and focused onto the substrate stage. Images were obtained through a color charge-coupled device (CCD, Nikon). A notch filter (533 nm) was placed between the objective and CCD to block the incident laser beam. White light was directed from the top of the stage for bright-field imaging. A halogen lamp was applied through the objective with a GFP filter cube (457487/502-538 nm for excitation/emission) for fluorescence imaging. The notch filter was removed in fluorescence imaging. Fluid sample was loaded onto the plasmonic substrate with a circular spacer (800 μm in height), which was covered by a cover slip to minimize the evaporation of solvent during experiments (FIG. 25 for the details of optical setup).

Perfluoropentane-in-water emulsion preparation. Perfluoropentane was added to phosphate buffer saline (1:10, v/v) followed by sonication for ten second to prepare perfluoropentane-in-phosphate buffer saline emulsion. Target protein solution in phosphate buffer saline was mixed with freshly prepared perfluoropentane/phosphate buffer saline emulsion. The sample was diluted with phosphate buffer saline to obtain the final perfluoropentane content of 0.5% v/v.

Liposome preparation. Liposome was prepared by a film hydration method, 50 µl of 1,2-dipalmitoyl-sn-glycero-3-phosphocholine solution (25 mg/mL) in chloroform/methanol (4:1) was placed in a glass tube and solvent was rotary-evaporated. Any residual amount of solvent was removed by keeping the sample in a vacuum oven overnight. A thin film of the lipid was hydrated with 1 ml of phosphate buffer saline for 10 min at 65° C. by sonication. The sample was further stabilized for 30 min at 65° C. The extrusion of liposomes was conducted by passage through a 0.1 µm polycarbonate filter twenty times. For the protein-immobilized case, the formulation of the liposomes was modified with additional 10 wt % of biotin-PE.

Biotinylation of Immunoglobulin G. NHS-biotin solution (1 µL, 40 mg/mL in DMSO) was added to Immunoglobulin G solution (1 mL, 1 mg/mL in phosphate buffer saline). The mixture was stirred for 3 hours at room temperature. Biotin-Immunoglobulin G was purified and collected by ultrafiltration (Amicon Ultra-0.5 Centrifugal Unit, 10K Da).

Substrate preparation. The gold nanoisland (Au NI) substrate was prepared by annealing 4.5 nm gold thin film (550° C./2 hours) thermally deposited on a glass slide (bar pressure: $1 \times 10^{15}$ Torr) as reported earlier (Lin L et al. *Nat. Photonics* 2018, 12 (4), 195-201). Lipid coating of substrate was done by adopting the alkanethiol/lipid hybrid system. First, the substrate was placed in 1 mM ethanolic solution of hexadecanethiol overnight and washed with ethanol to obtain self-assembled monolayer of hexadecanethiol on the gold nanoislands (HDT/Au Nis). The hexadecanethiol modified gold nanoisland substrate was then incubated in a 1,2-dipalmitoyl-sn-glycero-3-phosphocholine liposome dispersion (0.125 mg/mL) for 2 hours at 65° C. and overnight at room temperature. After washing with phosphate buffer saline, the substrate was stored in phosphate buffer saline for further use. Immunoglobulin G was immobilized on the substrate via streptavidin/biotin conjugation. The lipid-coated substrate was incubated in a streptavidin solution (10 µg/mL in phosphate buffer saline) and a biotin-Immunoglobulin G solution (10 µg/mL in phosphate buffer saline) sequentially. Unbound proteins were washed away by phosphate buffer saline after each incubation.

Numerical simulation. A finite-element solver (COMSOL Multiphysics) was used to simulate a flow profile. Cross-sectional geometry was constructed with a bubble (7.5 µm in radius) in a 200 µm×200 µm water domain, enclosed with solid boundaries on all sides. Temperature distribution in the entire domain was obtained by modelling optical input as a Gaussian heat influx ($\sim\exp[-2x^2/\omega^2]$) that was coupled to heat transfer in water. The heat transfer module and the laminar modules were coupled to model Marangoni and Rayleigh Bernard convection in the fluid domain. Marangoni flow in the simulation domain was induced by implementing a surface tension gradient along the bubble-water interface as a function of temperature (modeled as a slip interior wall) while nonslip walls were used for the other boundaries. The function of surface tension with respect to temperature was formulated to contain a linear dependence term and a vapor pressure term The surface tension of water is known to be affected by the presence of perfluoropentane vapor with the following relationship (Chemyshev V S et al. *Soft Matter* 2014, 10 (12), 1937-1943):

$$\gamma = \gamma_0 - 0.25[PFP]_v \quad (1)$$

where $[PFP]_v$ is vapor concentration in mol m$^{-3}$.

The relationship of vapor pressure of perfluoropentane with temperature is given as:

$$\log_{10} P = A - \frac{B}{T+C} \quad (2)$$

where A=4.2063, B=1103.454, and C=−39.77 (Barber E J et al. *J. Phys. Chem.* 1956, 60 (4), 504-505).

A vapor term, derived from Equation 1 and Equation 2 along with the ideal gas law, was added to the classical linear-dependence term to obtain the final temperature-dependent surface tension as:

$$\gamma(T) = \gamma_0 - K\Delta T - \frac{0.25}{RT} 10^{\left[A - \frac{B}{T+C}\right]} \quad (3)$$

where K is the temperature coefficient of surface tension and R is the gas constant.

Example 2

Described herein is a biphasic liquid system for low-power photothermal bubble generation and sensitive immunoassay.

Figure 32:
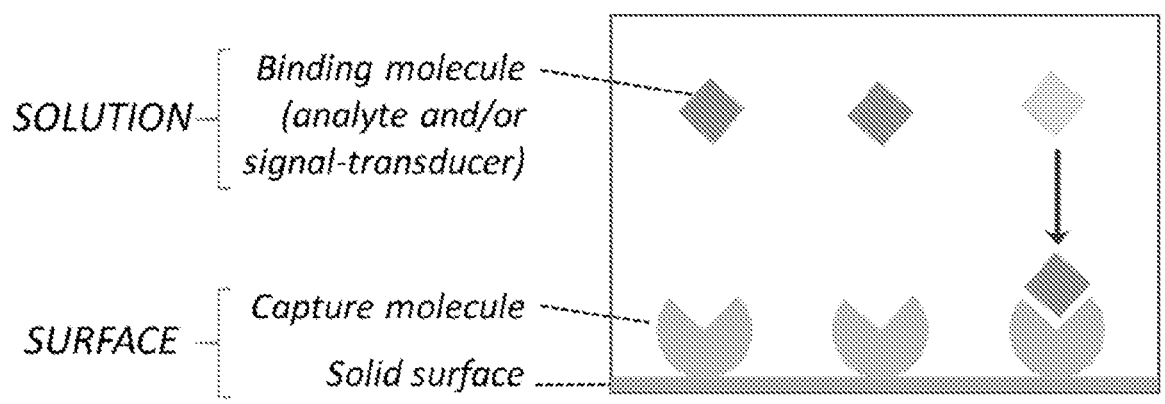
FIG. 32. Schematic illustration of surface-based biosensing.

Surface-based biosensing is shown schematically in FIG. 32, where capture molecules are disposed on a solid surface which are in contact with a solution in which a binding molecule (e.g., analyte and/or signal transducer) is dispersed. This type of surface-based biosensing can allow for facile separation of the analyte/signal transducer from the solution. This type of surface-based biosensing further allows for surface-confine readout. Molecular binding events are proportional to the sensing performance in these systems, which can be affected by/limited by diffusional transport and binding reactions. Diffusional transport can be improved by mixing the solution and/or increasing the surface concentration. The binding reactions can be improved using molecular designs for high affinity.

Photothermal bubbles can be generated by directing light onto a plasmonic substrate which is in thermal contact with a liquid/aqueous sample; a local photothermal effect can then lead to local evaporation of the liquid/aqueous sample to provide surface microbubble generation (Lin et al. *Nano Lett*, 2016, 16, 701-708; Rajeeva et al. *Matter*, 2019, 1, 1-12). Marangoni convection at the bubble-liquid interface can trap colloidal matter (e.g., matter on the micro- and/or nano-size scale) and accumulate ions (e.g., for nanocrystal synthesis) (Lin et al. *Nano Lett*, 2016, 16, 701-708; Rajeeva et al. *Matter*, 2019, 1, 1-12). Photothermal bubbles have potential as in-situ analyte concentrations in biosensing. However, the application of a photothermal bubble-generating scheme to protein-based sensing imposes a major challenge stemming from the high temperatures (>100° C.) needed to generate a bubble in an aqueous system.

To overcome this limitation, it was hypothesized that a bubble could be optothermally generated at a lower optical power and temperature if volatile liquid droplets suspended in an aqueous medium, e.g., a biphasic liquid system, are present on a plasmonic substrate. Accordingly, criteria for selection of such liquids for the biphasic component include low boiling point, water immiscibility, and bio-inertness. Bubble generation from a surface droplet of such a biphasic component and subsequent enhancement in biosensing at the substrate driven by bubble-mediated improvement in local concentration is shown schematically in FIG. 10 and FIG. 11.

Perfluoropentane ($C_5F_{12}$, PFP) was chosen for its low boiling temperature (~30° C.) as a bubble-generating component. The fluid system was comprised of microscale perfluoropentane droplets near the plasmonic substrate (FIG. 12). Threshold optical power for bubble generation was reduced to 33% of that in a pure aqueous medium. Bubble growth kinetics showed a burst of bubble growth at the beginning followed by a more gradual increase in bubble size (FIG. 15).

FIG. 24 shows the effect of optical power on immuno-binding affinity, where minimal degradation of the protein's binding affinity was found at optical powers sufficient for bubble generation in the biphasic system.

Bubble-mediated concentration of proteins was measured. Bubble-mediated protein accumulation was visualized by fluorescence (FIG. 16 and FIG. 17). Simulations indicated there high fluid velocity near the bubble (FIG. 18).

Surface modification of the substrate was used to prevent direct bubble printing of proteins on the substrate. More specifically, the surface was modified to include an antifouling coating comprising a lipid assembly on the gold substrate which effectively prevented direct bubble printing of proteins on the substrate (FIG. 19 and FIG. 20).

Figure 22:
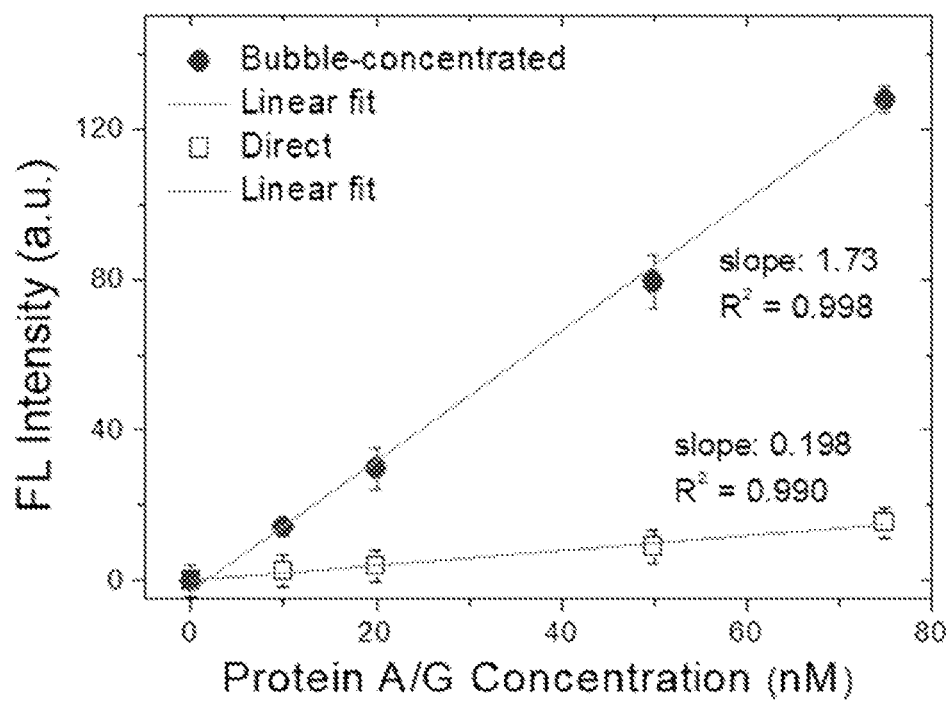
FIG. 22. Surface binding profile of FITC-protein A/G in the bubble-concentrated model (bubble concentration for 1 min) in comparison to the reference (incubation for 30 min). Fluorescence intensity in the bubble-concentrated model is the average of peak intensity at the ring patterns (n=3, individual bubble generation).

Surface capture of proteins by bubble generation was tested with a single pair of capture and binding proteins. Surface capture of the tested proteins were enhanced in the bubble-mediated system compared to a reference 30 minute diffusion based system (FIG. 21) as indicated by the amplification of the fluorescence signal with shortened incubation time compared to the reference system (FIG. 22, FIG. 23).

The optical power for bubble generation was effectively reduced in a biphasic liquid system. Bubble-mediated accumulation of proteins was observed. Surface capture of proteins was improved in terms of both magnitude and time. This system paves a path towards advanced sensors and spectroscopies.

Example 3

Described herein are systems and methods for high-performance detection and analysis of biomolecules for enhanced viral and other infectious disease diagnostics using temperature-tunable optothermal bubbles in a biphasic liquid. For example, described herein are systems and methods for rapid detection and analysis of biomolecules for efficient diagnostics of COVID-19 infection and other infectious and chronic diseases using temperature-tunable optothermal bubbles in a biphasic liquid.

A microbubble-generating biphasic system is demonstrated herein that can enhance molecular binding and reaction of biomolecules for high-performance disease diagnosis. The system includes (i) a biphasic fluid formulation that can control the working temperature of bubble formation and (ii) optothermal bubble generation through which biomolecules can be concentrated near the bubble, enhancing their binding and reaction. The microbubble-generating system can be incorporated into biosensing platforms as a rapid, strong amplifier for the purpose of improving sensitivity and throughput.

One biosensing platform that can readily incorporate the bubble system is for the identification of patients with COVID-19 infection. It has proven challenging to efficiently detect evidence of present and past infection due to limitations of classic testing methods for viral infection and antibodies generated against the SARS-CoV-2 virus. A diagnostic device that can measure molecules at high sensitivity, specificity, and throughput can be great value for patients, primary practitioners, and specialists to identify which patients have had COVID-19 exposure and are at risk of complications. This system can also be of major value for clinical trials where therapeutics and vaccines will be tested in patients to determine if the therapeutic or vaccine is effective to reduce complications of COVID-19 and to protect people. This can also be an advantage for identifying those patients for general use and epidemiological testing for COVID-19 and other viral or other infectious organisms.

This technique uses a biphasic fluid formulation that enables temperature control for bubble generation and concentration-driven enhancement of molecular binding and reaction. As a demonstration, perfluorocarbon liquid with varying boiling points (e.g., ~ 30° C. and 60° C. for perfluoropentane and perfluorohexane, respectively), as a bio-inert and water-immiscible component, is emulsified into an aqueous host. Perfluorocarbon droplets on the substrate undergo a microbubble transition upon light incident. For example, in protein-based sensing, perfluoropentane is used to reduce temperature near the bubble to the extent that minimizes thermal degradation of proteins. In a single protein-protein interaction model, surface binding of dispersed proteins to capture proteins is enhanced by one order of magnitude within one minute in the bubble-concentrated system, compared to that obtained from uncontrolled incubation for 30 min.

In conventional diffusion-based biosensing, molecular binding and/or reaction is limited by diffusional transport of interacting molecules, especially when the concentration is extremely low at an initial phase, resulting in time-consuming or sensitivity-limited false-negative readout. Besides diffusion-based sensing, preconcentration-assisted sensing including thermophoretic, electrophoretic, and microbubble-concentrated approaches have been demonstrated, but the type of target analytes is restricted by working conditions. In the systems and methods described herein, by having a biphasic liquid system, the range of working temperature and target analytes (from small molecules to nucleic acid and proteins) can be broadened in addition to concentration-based enhancement of molecular binding and reaction.

Biomolecular binding and reaction in conventional sensing systems is governed by passive diffusional transport of interacting molecules. For example, in typical sandwich-type enzyme-linked immunosorbent assay (ELISA), each surface binding step takes 30 minutes to an hour, indicating the diffusion-driven incubation process as a time-limiting step. In a gene amplification scheme for nucleic acid detection of viral infectious diseases, the low concentration of virus nucleic acid in clinical samples from patients at incubation period or early onset of symptoms contributes to large number of false negatives and thus community-acquired infection. In this case, the reaction rate at an early phase of gene amplification is intrinsically limited by the low concentration of reactants, leading to long amplification time and low throughput. The techniques described herein can overcome the diffusion limit by rapidly concentrating biomolecules, enhancing molecular binding and reaction. In comparison to bubble concentration in monophasic aqueous media where the working temperature is fixed at above 100° C., the biphasic configuration of fluid enables fine control over working temperature during bubble generation. Therefore, on-demand fluid formulation is possible with respect to desirable temperature required for each target application.

Herein, a perfluorocarbon-in-water biphasic system is developed, which is capable of generating microbubbles at a wide range of working temperatures (e.g., 30°–100° C.), thus broadening the range of target applications based on concentration-driven improvements in sensitivity and throughout. By formulating perfluorocarbon as a volatile, water-immiscible liquid component in the aqueous host, the threshold optical power and working temperature is modulated. Antifouling surface modification is performed to prevent unwanted printing of biomolecules during bubble generation. The microbubble-generating system is incorporated into biosensing platforms as a rapid, strong amplifier for the purpose of improving sensitivity and throughput. The systems and methods described herein exhibited enhancement in surface capture of proteins by one order of magnitude along with 30-fold reduction in incubation time (in a single protein-protein interaction model). The systems and methods described herein are workable for small-quantity analytes and for low concentration of biomolecules for early disease diagnosis.

The technique described herein, composed of fluid formulation and an optothermal add-on to control concentration and temperature, has compatibility with conventional biosensing platforms that include molecular probes and sensor configuration. Much quicker and more sensitive sensing of biomolecules is enabled with the systems and methods described herein. Fluid formulation can be modulated to meet temperature requirements of target systems (e.g., optimal temperature for specific protein-protein interaction, and 50-95° C. for polymerase-based gene amplification).

In the systems and methods described herein, bubbles are generated from surface droplets. Nonuniformity in droplet size and substrate distribution might limit the reliability of the system for practical applications. Uniform droplet size can be acquired by using surfactant and uniform patterning of droplets on the substrate by surface modification.

Beside disease diagnosis, biomolecular detection using the systems and methods described herein can be also applied to cell biology and pharmaceutics. Given the rapid and strong nature of the bubble concentrator, low-abundant biomarkers during metabolic events can be imaged with high resolution. High-throughput and high sensitivity of the detection system can serve as an efficient tool for screening biomarkers for drug discovery and evaluating therapeutic outcomes. As such, the systems and methods described herein can be of interest to hospitals, clinics, doctors, patients, medical companies, etc.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

The methods of the appended claims are not limited in scope by the specific methods described herein, which are intended as illustrations of a few aspects of the claims and any methods that are functionally equivalent are intended to fall within the scope of the claims. Various modifications of the methods in addition to those shown and described herein are intended to fall within the scope of the appended claims. Further, while only certain representative method steps disclosed herein are specifically described, other combinations of the method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

What is claimed is:

1. A method comprising:
illuminating a first location of an optothermal substrate with electromagnetic radiation;
   wherein the optothermal substrate converts at least a portion of the electromagnetic radiation into thermal energy;
   wherein the optothermal substrate is in thermal contact with a biphasic liquid sample comprising an aqueous solution and one or more droplets comprising a water-immiscible liquid dispersed in the aqueous solution, and wherein the aqueous solution comprises water and a plurality of analytes;
   wherein the aqueous solution has a boiling point and the water-immiscible liquid has a boiling point, and the boiling point of the water-immiscible liquid is less than the boiling point of the aqueous solution;
   wherein before illumination, the biphasic liquid sample has a first temperature and the first temperature is less than the boiling point of the water-immiscible liquid;
   wherein at least one of the droplets comprising the water-immiscible liquid is disposed on the optothermal substrate proximate the first location, the at least one droplet comprising the water-immiscible liquid disposed on the optothermal substrate being a surface droplet;
   wherein the thermal energy provided by the optothermal substrate increases the temperature of the biphasic liquid sample proximate the first location to a second temperature, wherein the second temperature is greater than or equal to the boiling point of the water-immiscible liquid and less than the boiling point of the aqueous solution;
thereby:
   generating a bubble at a location in the biphasic liquid sample proximate to the first location of the optothermal substrate via vaporization of the surface droplet via optothermal effects, the bubble having a gas-liquid interface with the aqueous solution and a gas-solid interface with the optothermal substrate;
   trapping at least a portion of the plurality of analytes at the gas-liquid interface of the bubble and the aqueous solution, said portion of the plurality of analytes trapped at the gas-liquid interface being a trapped portion of the plurality of analytes; and
   depositing at least a portion of the trapped portion of the plurality of analytes on the optothermal substrate proximate to the gas-solid interface of the bubble and the optothermal substrate, said portion of the trapped portion of the plurality of analytes deposited on the optothermal substrate being a deposited portion of the plurality of analytes.

2. The method of claim 1, wherein:
the optothermal substrate comprises a plasmonic substrate and the plasmonic substrate comprises a plurality of plasmonic particles, and the plurality of plasmonic particles comprise a metal selected from the group consisting of Au, Ag, Pd, Cu, Cr, Al, and combinations thereof;
the optothermal substrate comprises a metal film comprising a metal selected from the group consisting of Al, Ti, Cr, Mn, Fe, Co, Ni, Cu, Mo, Pd, Ag, Cd, Pt, Au, and combinations thereof;
or a combination thereof.

3. The method of claim 1, wherein the optothermal substrate comprises a plasmonic substrate and the electromagnetic radiation comprises a wavelength that overlaps with at least a portion of the plasmon resonance energy of the plasmonic substrate, and the bubble is generated by plasmon-enhanced photothermal effects.

4. The method of claim 1, wherein the optothermal substrate further comprises an antifouling layer.

5. The method of claim 1, wherein the aqueous solution comprises a phosphate buffer saline solution, a bodily fluid, or a combination thereof.

6. The method of claim 1, wherein the plurality of analytes comprise a biomolecule, a macromolecule, a pathogen, an enzyme, a protein, a pathogen, an antibody, or a combination thereof.

7. The method of claim 1, wherein the plurality of analytes have a concentration of from 0.01 femtomolar (fM) to 100 nanomolar (nM) in the aqueous solution.

8. The method of claim 1, wherein the biphasic liquid sample has a volume from 1 nanoliter (nL) to 1 milliliter (mL).

9. The method of claim 1, wherein the water-immiscible liquid comprises a perfluorocarbon.

10. The method of claim 1, wherein the trapped portion of the plurality of analytes are not damaged during the trapping, wherein the deposited portion of the plurality of analytes are not damaged during the deposition, or a combination thereof.

11. The method of claim 1, wherein the method further comprises capturing an electromagnetic signal from at least a portion of the deposited portion of the plurality of analytes, at least a portion of the optothermal substrate proximate the first location, or a combination thereof; and processing the electromagnetic signal to determine a property of the biphasic liquid sample.

12. The method of claim 11, wherein the property of the biphasic liquid sample comprises the presence of the surface droplet, the presence of the bubble, the presence of the deposited portion of the plurality of analytes, or a combination thereof.

13. The method of claim 11, wherein the property of the biphasic liquid sample comprises the presence of the deposited portion of the plurality of analytes and the method further comprises diagnosing and/or monitoring a disease in a subject based thereon.

14. The method of claim 13, wherein the disease comprises:
a respiratory infection;
a viral infection with an influenza virus, a coronavirus, or a combination thereof;
or a combination thereof.

15. The method of claim 11, wherein the time elapsed from illuminating the first location of the optothermal substrate to determining the property of the biphasic liquid sample is from 1 millisecond to 30 minutes.

16. The method of claim 1, further comprising:
illuminating a second location of the optothermal substrate with the electromagnetic radiation;
wherein a second droplet comprising the water-immiscible liquid is disposed on the optothermal substrate proximate the second location, the second droplet comprising the water-immiscible liquid disposed on the optothermal substrate being a second surface droplet;
wherein the optothermal substrate converts at least a portion of the electromagnetic radiation into thermal energy, and the thermal energy increases the temperature of the biphasic liquid sample proximate the second location to a third temperature, wherein the third temperature is greater than or equal to the boiling point of the water-immiscible liquid;
thereby:
generating a second bubble at a location in the biphasic liquid sample proximate to the second location of the optothermal substrate via vaporization of the second surface droplet via optothermal effects, the second bubble having a gas-liquid interface with the aqueous solution and a gas-solid interface with the optothermal substrate;
trapping at least a second portion of the plurality of analytes at the gas-liquid interface of the second bubble and the aqueous solution, said portion of the plurality of analytes trapped at the gas-liquid interface of the second bubble and the aqueous solution being a second trapped portion of the plurality of analytes; and
depositing at least a portion of the second trapped portion of the plurality of analytes on the optothermal substrate proximate to the gas-solid interface of the second bubble and the optothermal substrate, said portion of the second trapped portion of the plurality of analytes deposited on the optothermal substrate being a second deposited portion of the plurality of analytes.

17. The method of claim 16, wherein the method further comprises:
capturing a second electromagnetic signal from at least a portion of the second deposited portion of the plurality of analytes, at least a portion of the optothermal substrate proximate the second location, or a combination thereof; and
processing the second electromagnetic signal to determine a second property of the biphasic liquid sample;
wherein the second property of the biphasic liquid sample comprises the presence of the second surface droplet, the presence of the second bubble, the presence of the second deposited portion of the plurality of analytes, or a combination thereof.

18. The method of claim 1, further comprising washing the optothermal substrate to substantially remove the deposited portion of the plurality of analytes and, if present, the second deposited portion of the plurality of analytes.

19. The method of claim 18, wherein the washed optothermal substrate is used as the optothermal substrate.

20. A system comprising:
an optothermal substrate;
a biphasic liquid sample comprising:
- an aqueous solution and one or more droplets comprising a water-immiscible liquid dispersed in the aqueous solution;
- wherein the aqueous solution comprises water and a plurality of analytes; and
- wherein the water-immiscible liquid has a boiling point;

wherein the biphasic liquid sample is in thermal contact with the optothermal substrate; and
a light source is configured to illuminate a first location of the optothermal substrate with electromagnetic radiation;
- wherein the optothermal substrate converts at least a portion of the electromagnetic radiation into thermal energy;
- wherein before illumination, the biphasic liquid sample has a first temperature and the first temperature is less than the boiling point of the water-immiscible liquid;
- wherein at least one of the droplets comprising the water-immiscible liquid is disposed on the optothermal substrate proximate the first location, the at least one droplet comprising the water-immiscible liquid disposed on the optothermal substrate being a surface droplet;
- wherein the thermal energy provided by the optothermal substrate increases the temperature of the biphasic liquid sample proximate the first location to a second temperature, wherein the second temperature is greater than or equal to the boiling point of the water-immiscible liquid;

thereby:
- generating a bubble at a location in the biphasic liquid sample proximate to the first location of the optothermal substrate via vaporization of the surface droplet via optothermal effects, the bubble having a gas-liquid interface with the aqueous solution and a gas-solid interface with the optothermal substrate;
- trapping at least a portion of the plurality of analytes at the gas-liquid interface of the bubble and the aqueous solution, said portion of the plurality of analytes trapped at the gas-liquid interface being a trapped portion of the plurality of analytes; and
- depositing at least a portion of the trapped portion of the plurality of analytes on the optothermal substrate proximate to the gas-solid interface of the bubble and the optothermal substrate, said portion of the trapped portion of the plurality of analytes deposited on the optothermal substrate being a deposited portion of the plurality of analytes.

* * * * *